(12) United States Patent
Thelen et al.

(10) Patent No.: US 7,485,119 B2
(45) Date of Patent: Feb. 3, 2009

(54) METHOD AND APPARATUS FOR REDUCING FEMORAL FRACTURES

(75) Inventors: Sarah L. Thelen, North Manchester, IN (US); Antony J. Lozier, Warsaw, IN (US); Nicolas J. Pacelli, Culver, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 11/250,927

(22) Filed: Oct. 14, 2005

(65) Prior Publication Data
US 2006/0064164 A1    Mar. 23, 2006

Related U.S. Application Data

(63) Continuation-in-part of application No. 11/061,898, filed on Feb. 18, 2005, which is a continuation-in-part of application No. 10/358,009, filed on Feb. 4, 2003, now abandoned, which is a continuation-in-part of application No. 10/266,319, filed on Oct. 8, 2002, which is a continuation-in-part of application No. 10/155,683, filed on May 23, 2002, which is a continuation-in-part of application No. 09/520,351, filed on Mar. 7, 2000, now Pat. No. 6,447,514.

(60) Provisional application No. 60/654,481, filed on Feb. 18, 2005, provisional application No. 60/621,487, filed on Oct. 22, 2004.

(51) Int. Cl.
*A61B 17/56* (2006.01)
*A61F 2/30* (2006.01)

(52) U.S. Cl. ........................................ 606/63

(58) Field of Classification Search ............... 606/53, 606/60, 62, 63
See application file for complete search history.

(56) References Cited

U.S. PATENT DOCUMENTS

| | | | |
|---|---|---|---|
| 3,128,768 A | | 4/1964 | Mikelis |
| 3,991,600 A | | 11/1976 | Del Fabro |
| 4,274,163 A | | 6/1981 | Malcom et al. |
| 4,285,618 A | | 8/1981 | Shanley |
| 4,313,434 A | | 2/1982 | Segal |
| 4,399,814 A | | 8/1983 | Pratt, Jr. et al. |
| 4,438,762 A | | 3/1984 | Kyle |
| 4,466,435 A | * | 8/1984 | Murray .................. 606/94 |
| 4,576,152 A | | 3/1986 | Muller et al. |
| 4,625,722 A | | 12/1986 | Murray |
| 4,627,434 A | * | 12/1986 | Murray .................. 606/63 |

(Continued)

FOREIGN PATENT DOCUMENTS

AU        200128554        6/2001

(Continued)

*Primary Examiner*—Anu Ramana
(74) *Attorney, Agent, or Firm*—Bakers & Daniels LLP

(57) ABSTRACT

A method and apparatus for reducing a hip fracture utilizing a minimally invasive procedure. A femoral implant achieves intramedullary fixation as well as fixation into the femoral head. To optimally position the femoral implant, a minimally invasive incision is aligned with the greater trochanter and the wound is developed to expose the greater trochanter. Various reamers are utilized to prepare a cavity in the femur extending from the greater trochanter into the femoral head and further extending from the greater trochanter into the intramedullary canal of the femur.

15 Claims, 60 Drawing Sheets

U.S. PATENT DOCUMENTS

| | | | |
|---|---|---|---|
| 4,662,887 A | 5/1987 | Turner et al. | |
| 4,714,478 A | 12/1987 | Fischer | |
| 4,769,008 A | 9/1988 | Hessel | |
| 4,776,330 A | 10/1988 | Chapman et al. | |
| 4,777,942 A | 10/1988 | Frey et al. | |
| 4,808,184 A | 2/1989 | Tepic | |
| 4,815,454 A | 3/1989 | Dozier, Jr. | |
| 4,915,693 A | 4/1990 | Hessel | |
| 4,969,888 A | 11/1990 | Scholten et al. | |
| 4,994,065 A | 2/1991 | Gibbs et al. | |
| 5,011,477 A | 4/1991 | Winchell et al. | |
| 5,061,243 A | 10/1991 | Winchell et al. | |
| 5,080,652 A | 1/1992 | Sancoff et al. | |
| 5,102,413 A | 4/1992 | Poddar | |
| 5,105,983 A | 4/1992 | Sancoff et al. | |
| 5,108,404 A | 4/1992 | Scholten et al. | |
| 5,284,481 A | 2/1994 | Soika et al. | |
| 5,303,718 A | 4/1994 | Krajicek | |
| 5,306,277 A | 4/1994 | Bryant et al. | |
| 5,312,408 A | 5/1994 | Brown | |
| 5,342,363 A | 8/1994 | Richelsoph | |
| 5,346,495 A * | 9/1994 | Vargas, III | 606/92 |
| 5,350,379 A | 9/1994 | Spievack | |
| 5,376,123 A | 12/1994 | Klaue et al. | |
| 5,403,320 A | 4/1995 | Luman et al. | |
| 5,423,850 A | 6/1995 | Berger | |
| 5,462,547 A | 10/1995 | Weigum | |
| 5,480,400 A | 1/1996 | Berger | |
| 5,514,137 A | 5/1996 | Coutts | |
| 5,527,316 A | 6/1996 | Stone et al. | |
| 5,540,694 A | 7/1996 | DeCarlo, Jr. et al. | |
| 5,549,679 A | 8/1996 | Kuslich | |
| 5,558,134 A | 9/1996 | Miyazaki | |
| 5,571,189 A | 11/1996 | Kuslich | |
| 5,578,035 A | 11/1996 | Lin | |
| 5,591,168 A | 1/1997 | Judet et al. | |
| 5,645,597 A | 7/1997 | Krapiva | |
| 5,649,930 A | 7/1997 | Kertzner | |
| 5,658,310 A | 8/1997 | Berger | |
| 5,681,289 A | 10/1997 | Wilcox et al. | |
| 5,690,671 A | 11/1997 | McGurk et al. | |
| 5,693,099 A | 12/1997 | Harle | |
| 5,695,518 A | 12/1997 | Laerum | |
| 5,772,662 A | 6/1998 | Chapman et al. | |
| 5,824,087 A | 10/1998 | Aspden et al. | |
| 5,827,289 A | 10/1998 | Reiley et al. | |
| 5,951,160 A | 9/1999 | Ronk | |
| 5,976,139 A | 11/1999 | Bramlet | |
| 5,997,582 A | 12/1999 | Weiss | |
| 6,024,724 A | 2/2000 | Lee | |
| 6,042,380 A * | 3/2000 | De Rowe | 433/173 |
| 6,053,922 A | 4/2000 | Krause | |
| 6,066,154 A | 5/2000 | Reiley et al. | |
| 6,096,042 A | 8/2000 | Herbert | |
| 6,110,211 A | 8/2000 | Weiss | |
| 6,132,214 A | 10/2000 | Suhonen et al. | |
| 6,132,468 A | 10/2000 | Mansmann | |
| 6,156,069 A | 12/2000 | Amstutz | |
| 6,228,091 B1 | 5/2001 | Lombardo et al. | |
| 6,228,092 B1 | 5/2001 | Mikhail | |
| 6,231,615 B1 | 5/2001 | Preissman | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,261,289 B1 | 7/2001 | Levy | |
| 6,306,177 B1 * | 10/2001 | Felt et al. | 623/23.6 |
| 6,355,019 B1 | 3/2002 | Kriesel et al. | |
| 6,358,251 B1 | 3/2002 | Mirza | |
| 6,413,239 B1 | 7/2002 | Burns et al. | |
| 6,425,923 B1 | 7/2002 | Stalcup et al. | |
| 6,488,684 B2 | 12/2002 | Sterghos et al. | |
| 6,613,054 B2 | 9/2003 | Scribner et al. | |
| 6,695,844 B2 | 2/2004 | Bramlet et al. | |
| 6,736,818 B2 | 5/2004 | Perren et al. | |
| 6,755,862 B2 | 6/2004 | Keynan | |
| 6,755,865 B2 | 6/2004 | Tarabishy | |
| 2001/0034526 A1 | 10/2001 | Kuslich et al. | |
| 2002/0010472 A1 | 1/2002 | Kuslich et al. | |
| 2002/0022847 A1 | 2/2002 | Ray et al. | |
| 2002/0193799 A1 | 12/2002 | Chappuis et al. | |
| 2005/0113836 A1 | 5/2005 | Lozier | |
| 2006/0052788 A1 | 3/2006 | Thelen et al. | |

FOREIGN PATENT DOCUMENTS

| | | |
|---|---|---|
| EP | 0496636 | 1/1992 |
| EP | 0617927 | 10/1994 |
| EP | 1 132 051 | 9/2001 |
| EP | 1132053 | 9/2001 |
| EP | 1149562 | 10/2001 |
| EP | 1201191 | 5/2002 |
| EP | 1 348 384 | 10/2003 |
| FR | 2671006 | 7/1992 |
| FR | 2802080 | 6/2001 |
| NL | 9001858 | 8/1990 |
| WO | WO9820939 | 5/1998 |
| WO | WO 02/051319 A | 7/2002 |

* cited by examiner

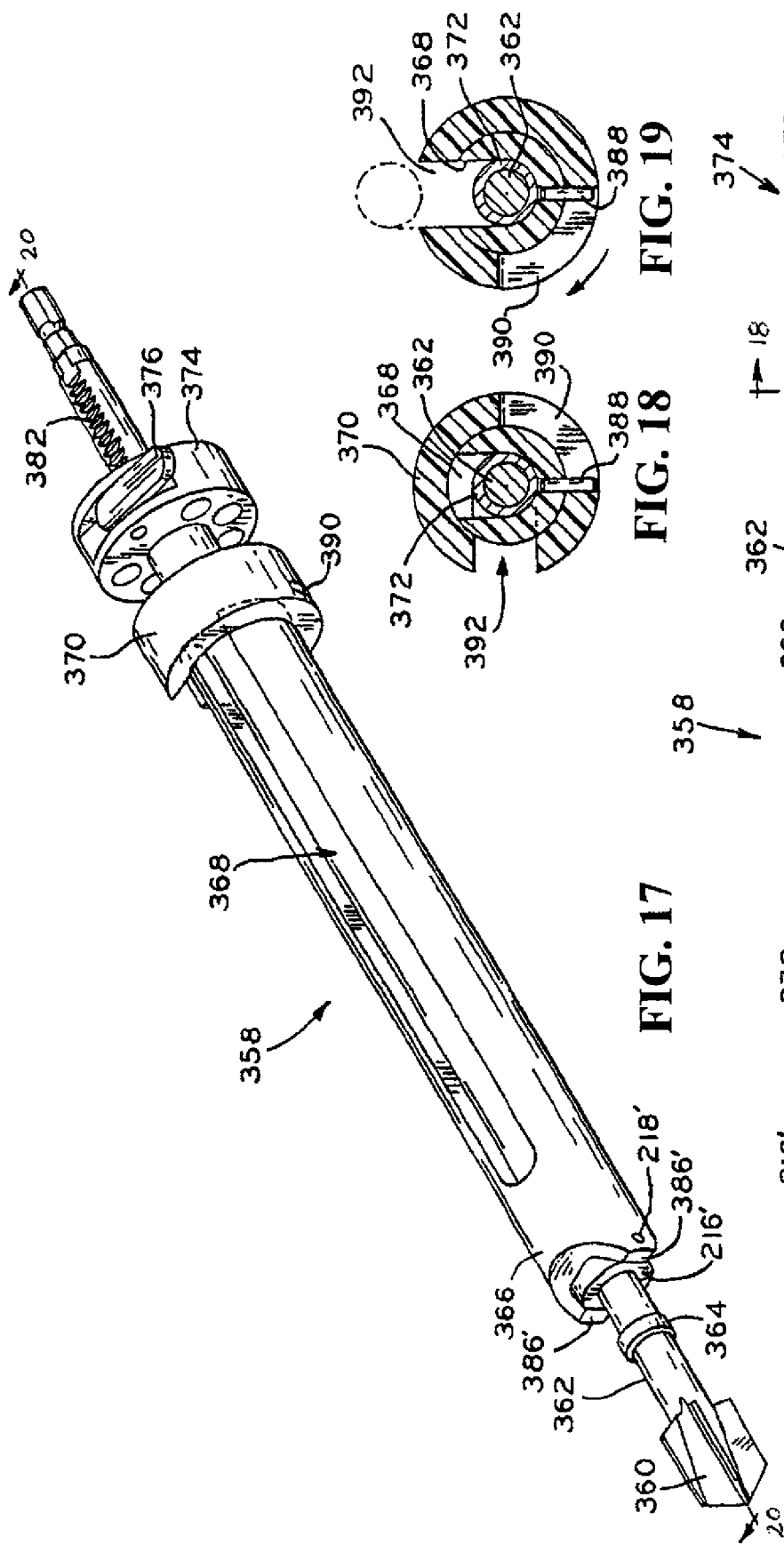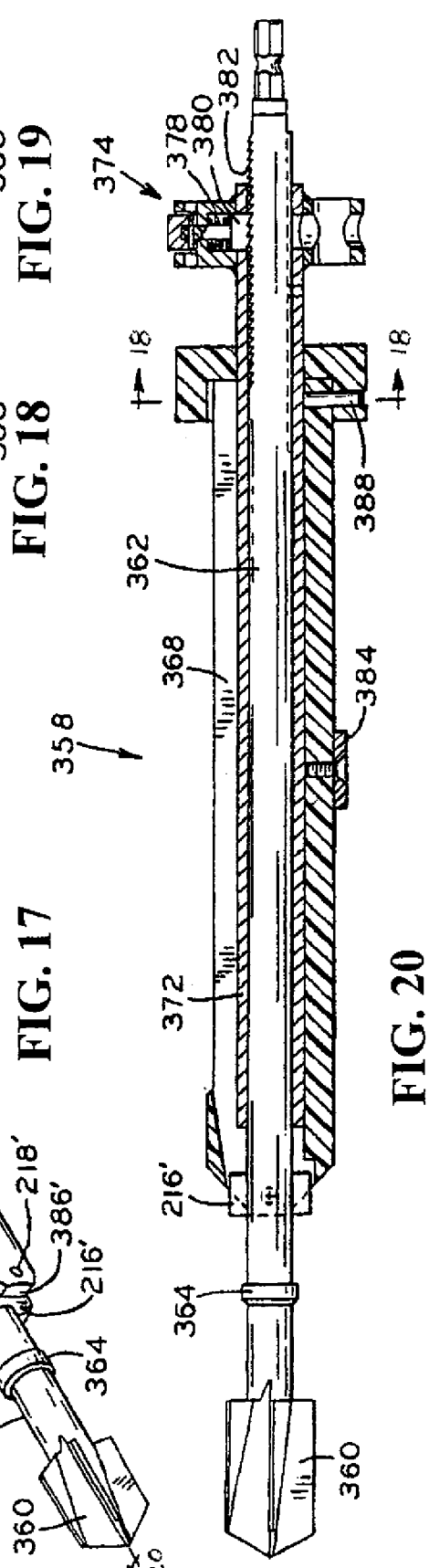

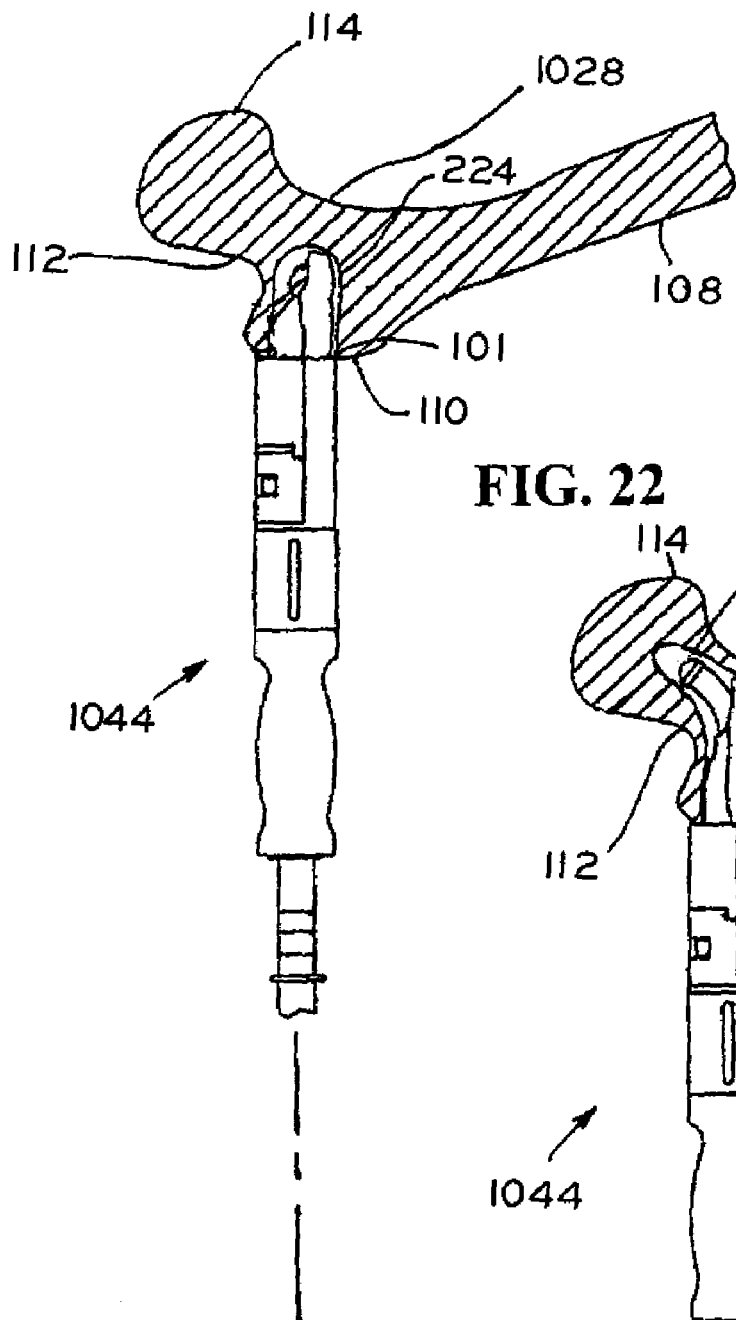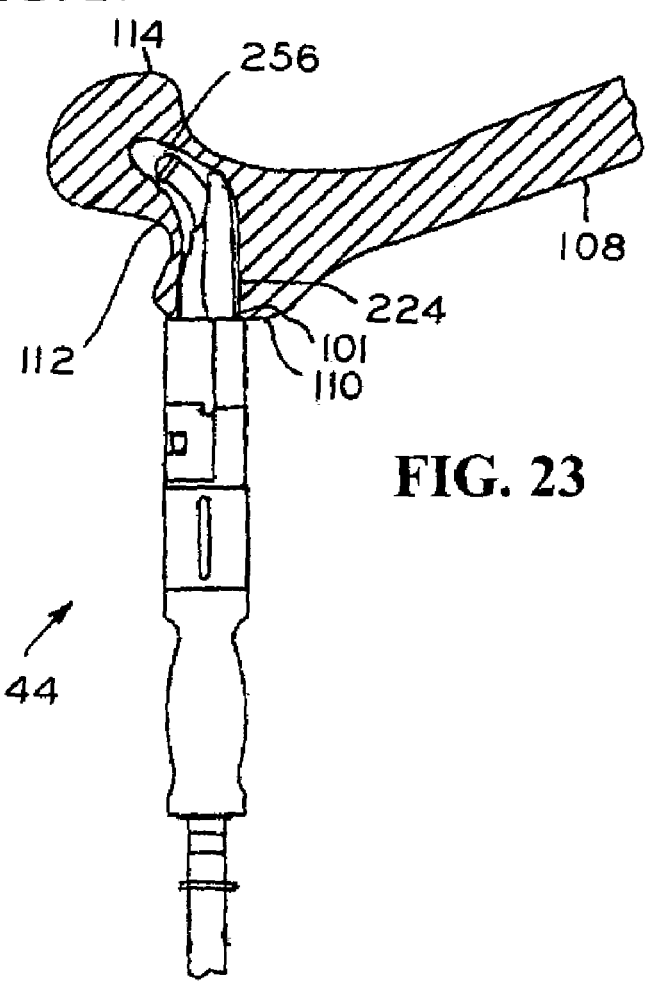
FIG. 22
FIG. 23

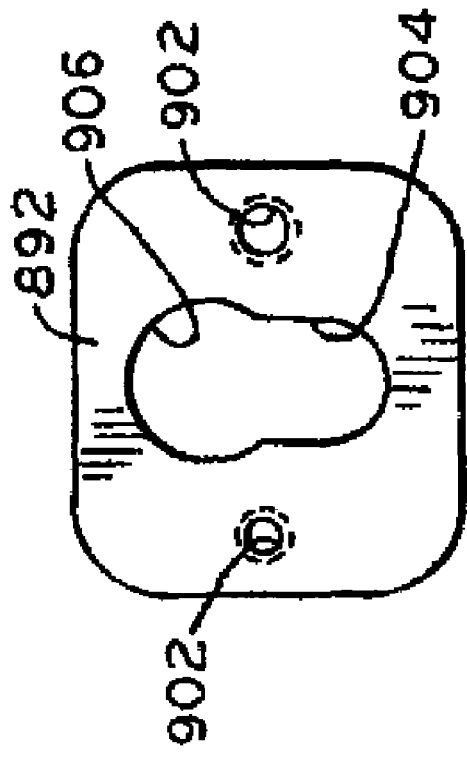
FIG. 35
FIG. 36
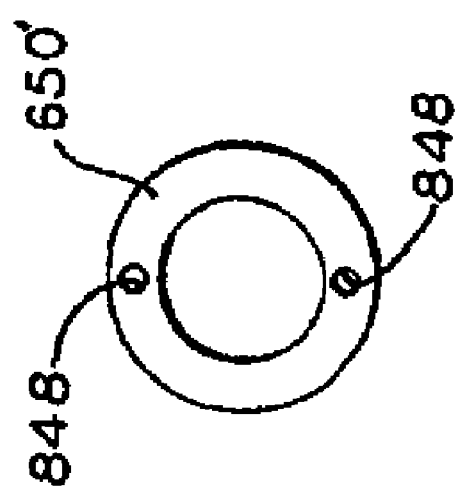
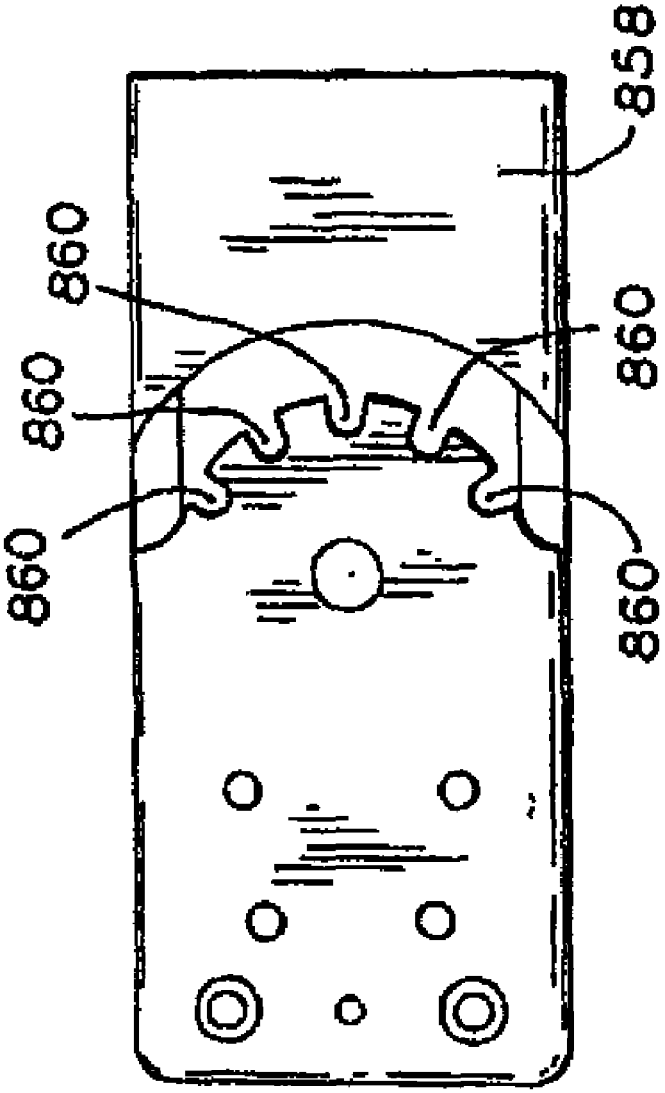
FIG. 37

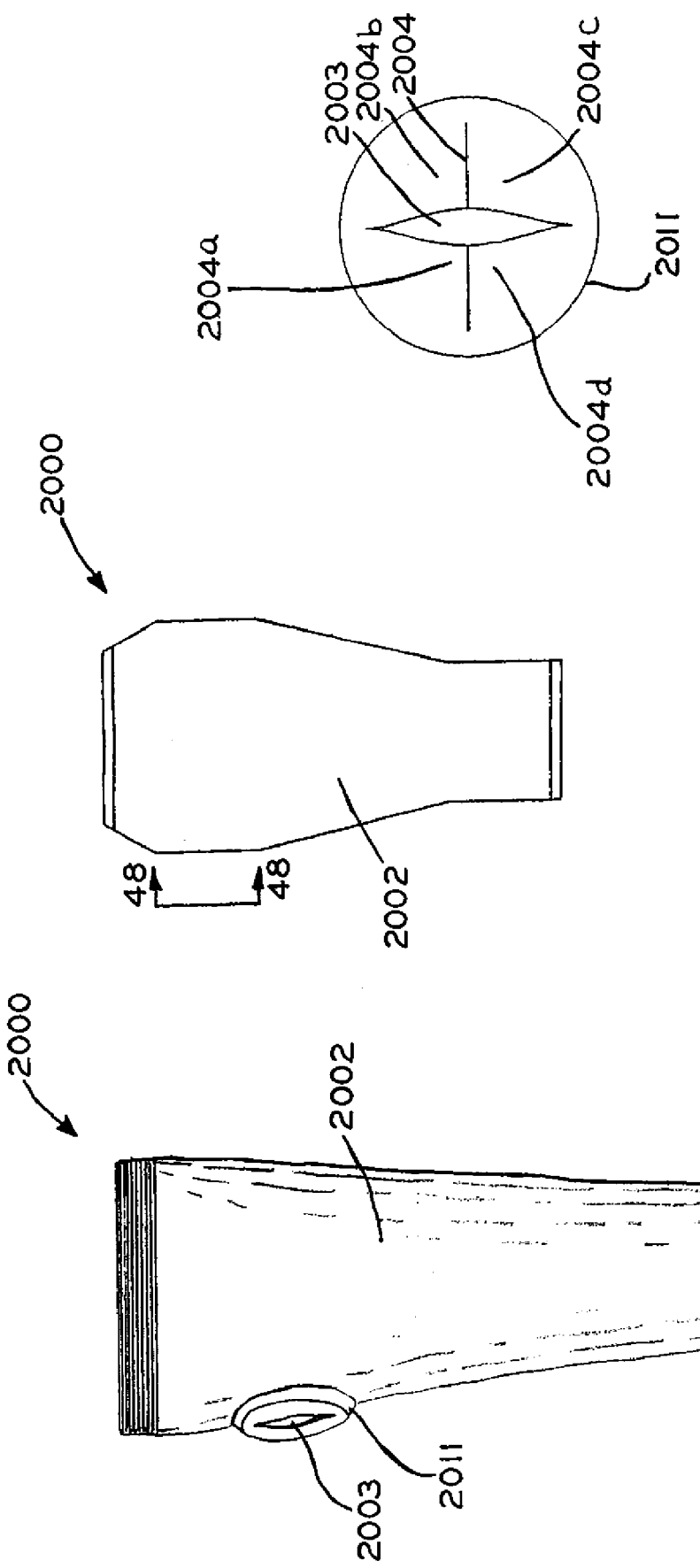

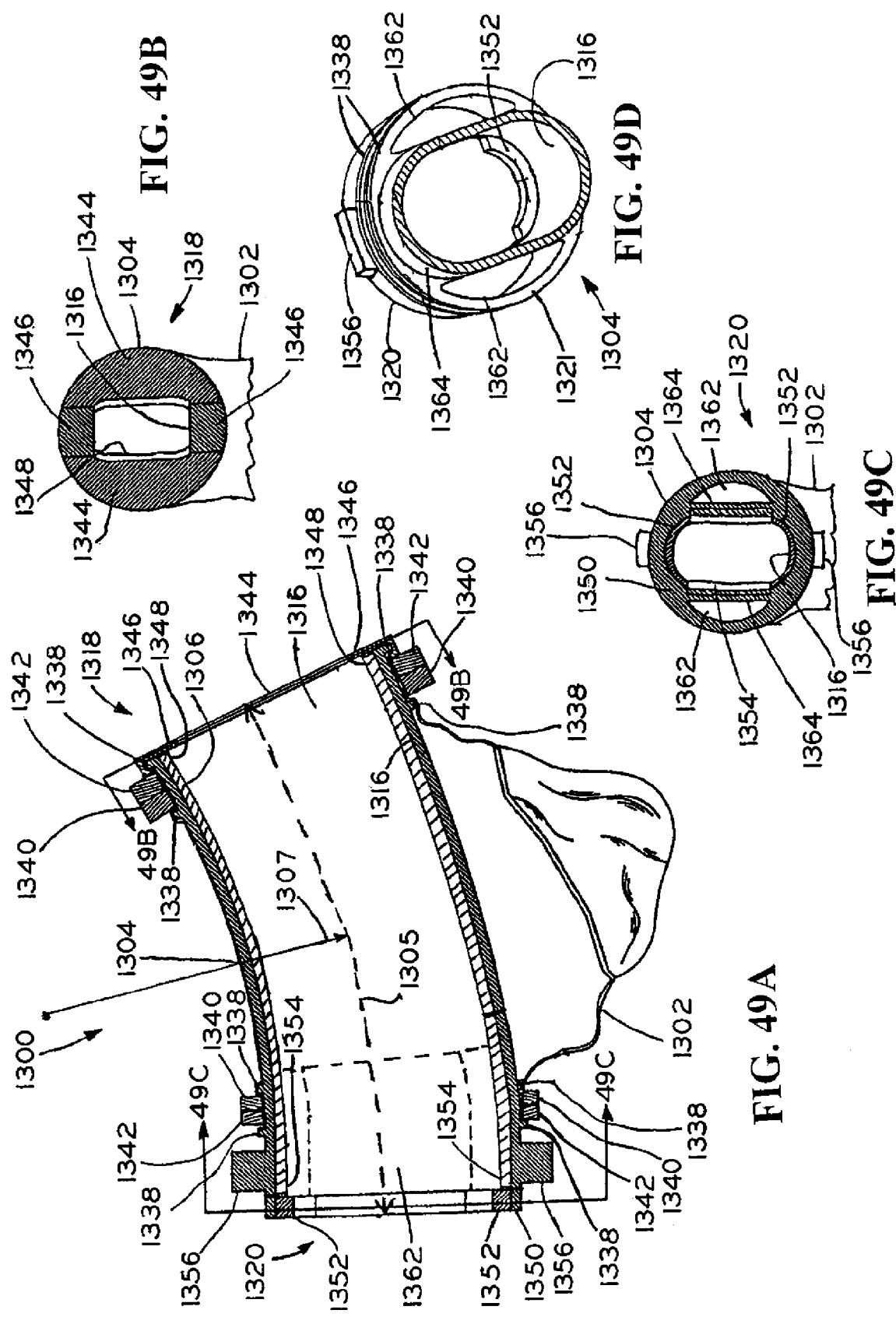

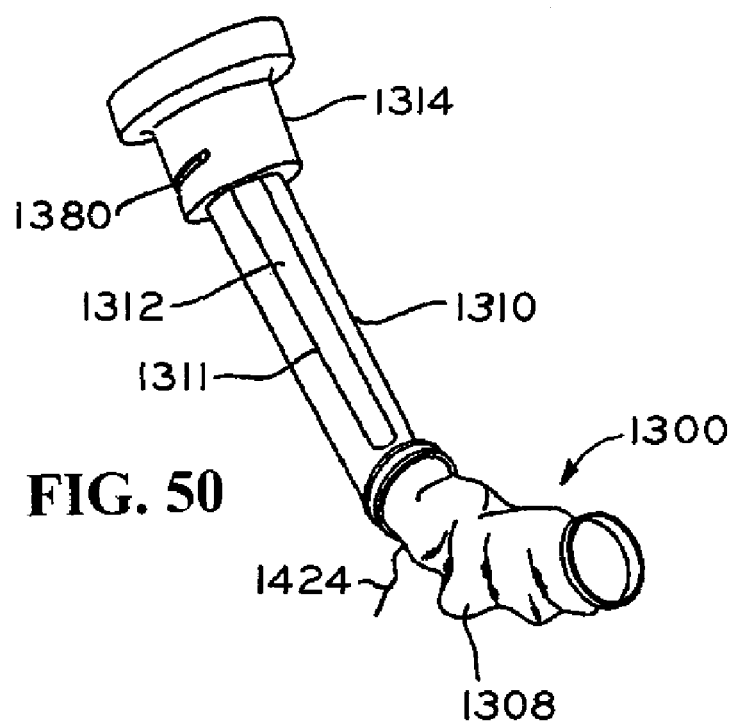
FIG. 50
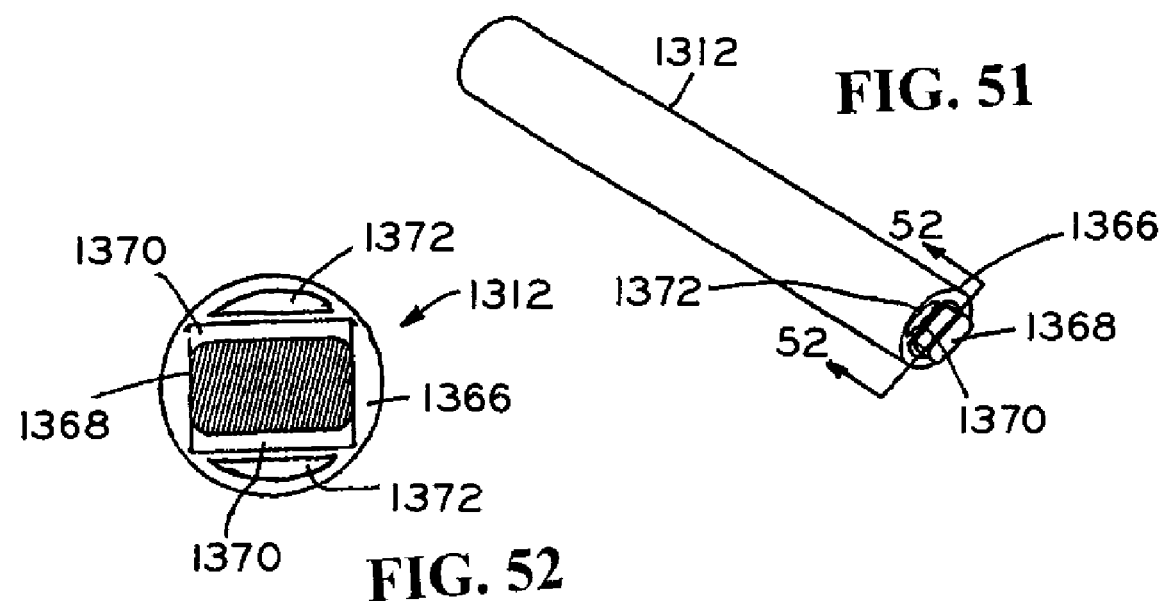
FIG. 51
FIG. 52

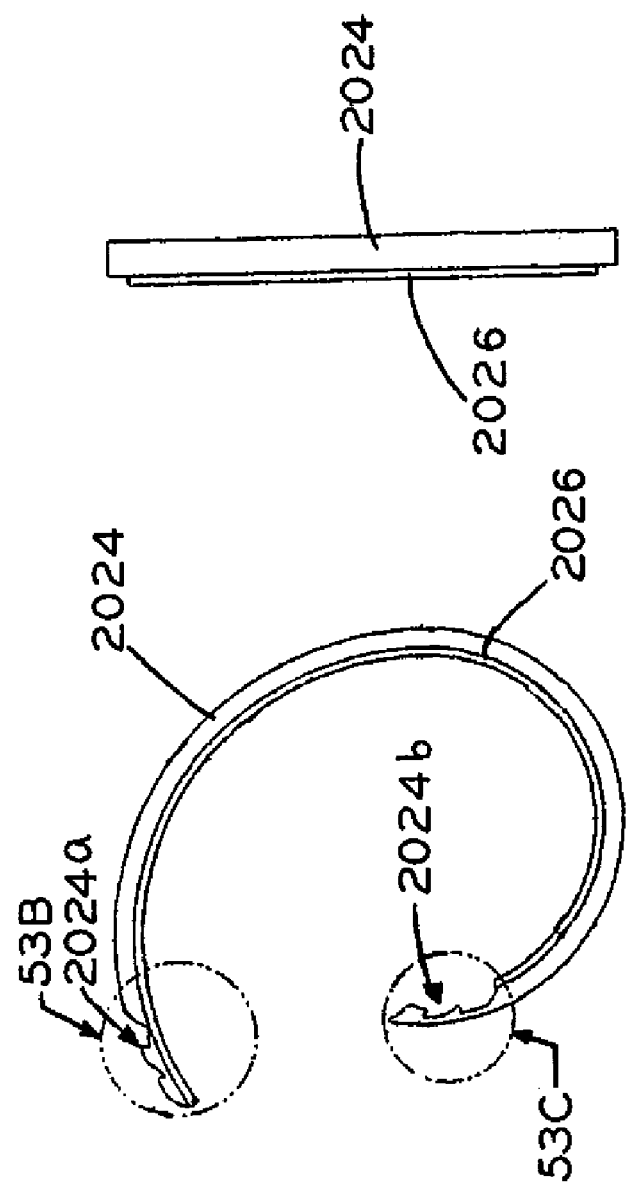
FIG. 53D
FIG. 53A
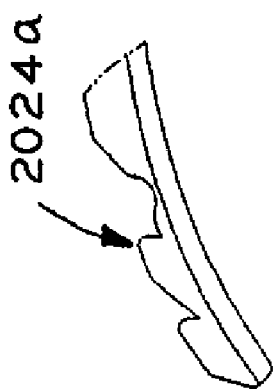
FIG. 53B
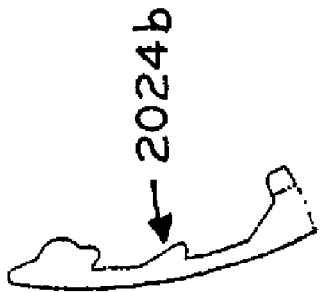
FIG. 53C

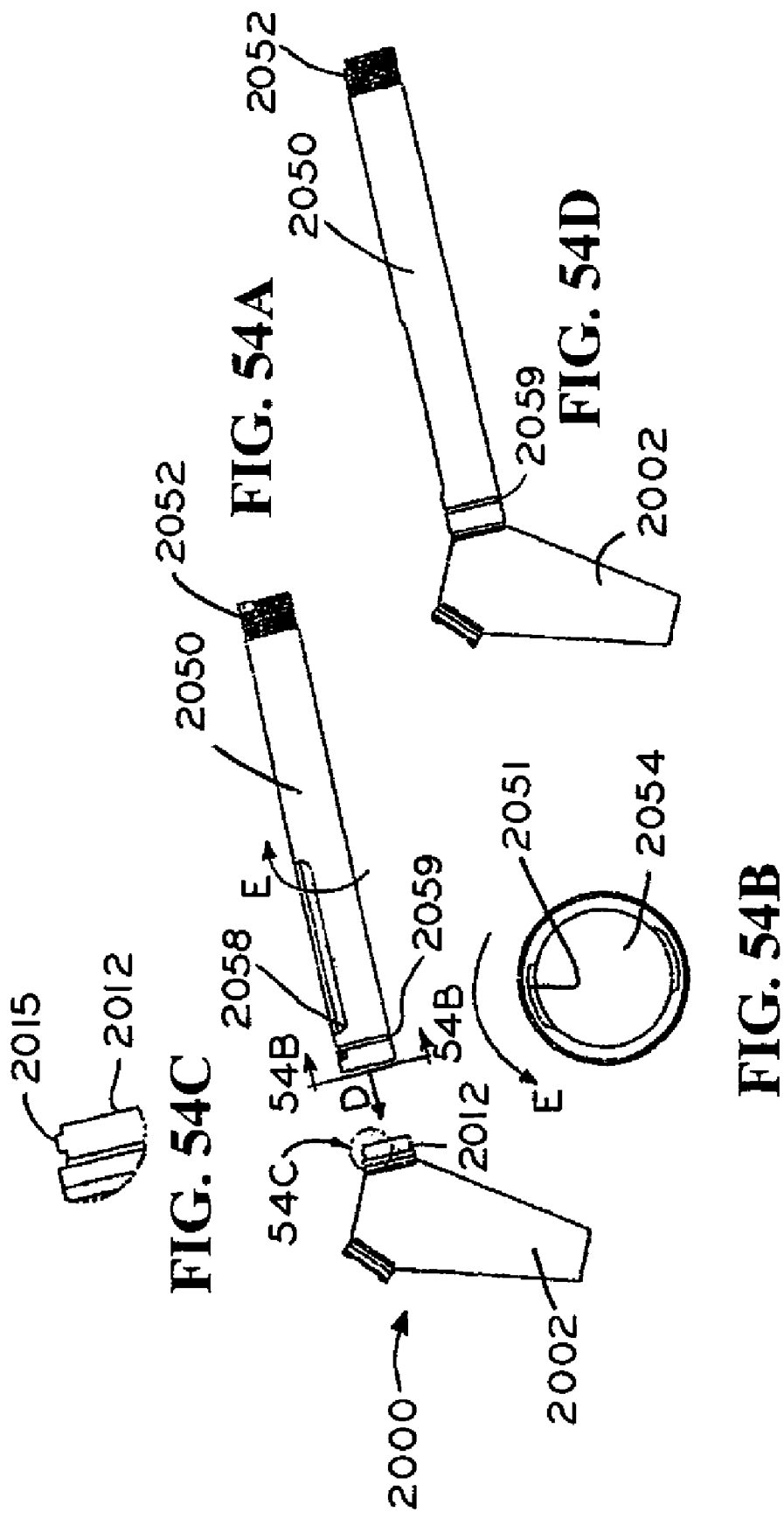

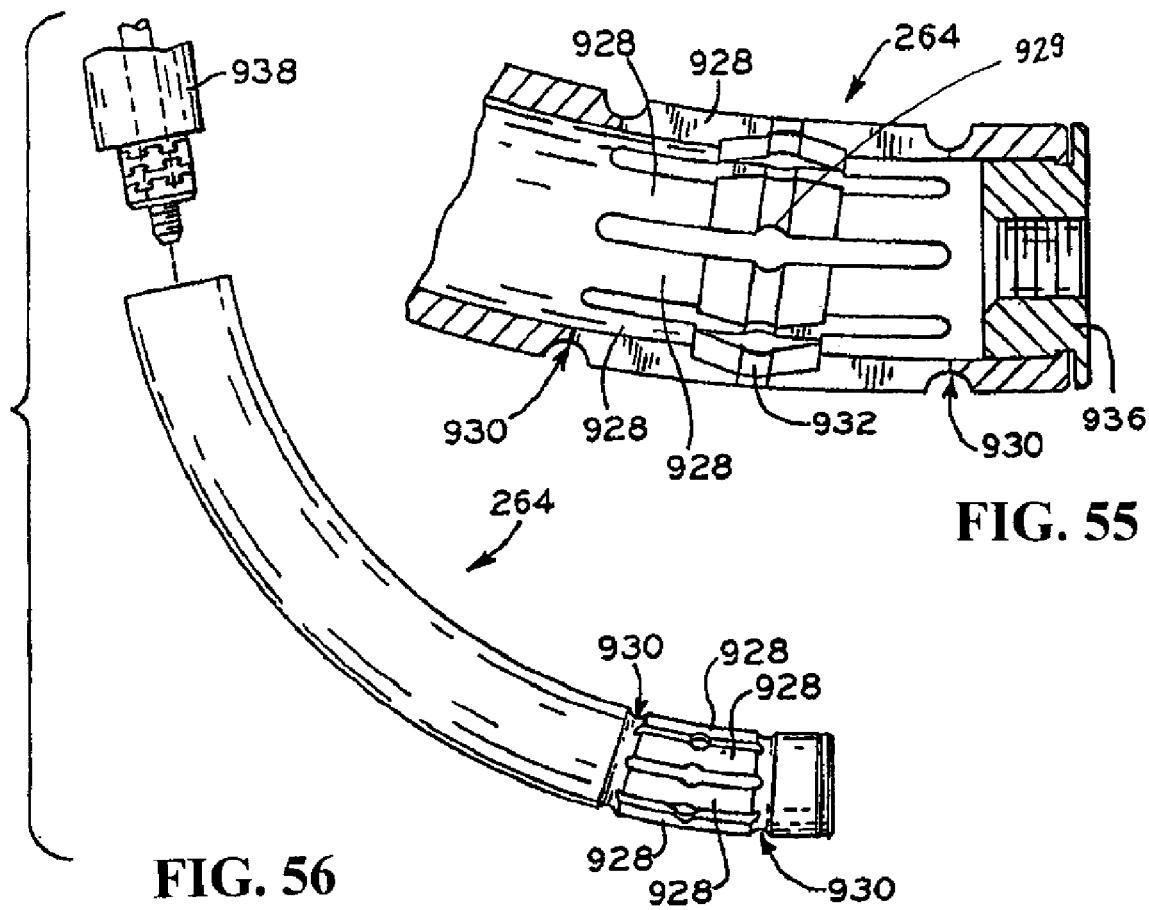
FIG. 55
FIG. 56
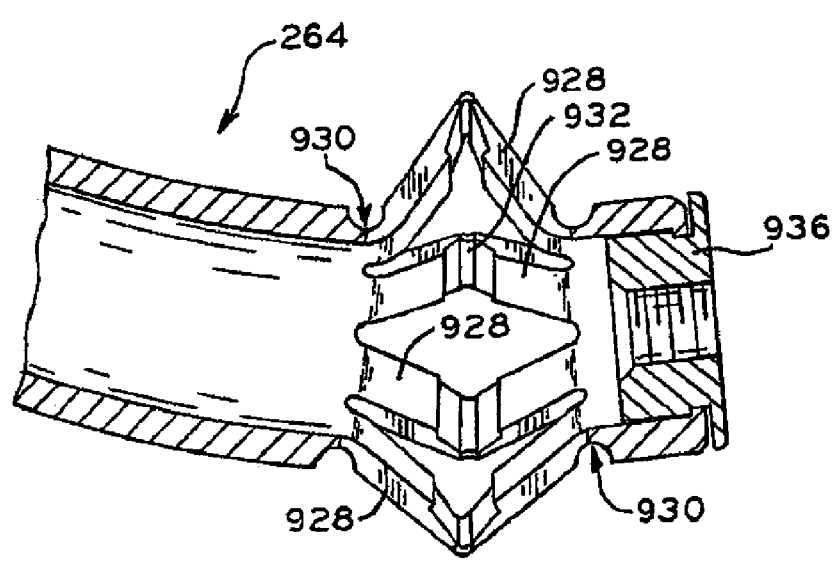
FIG. 57

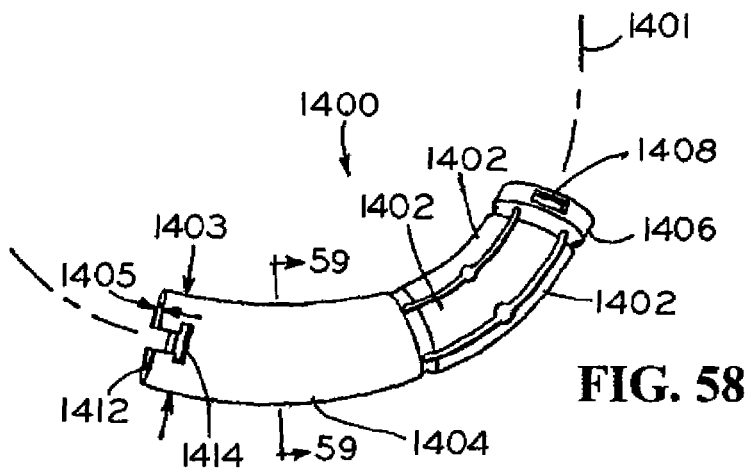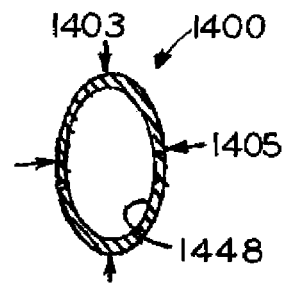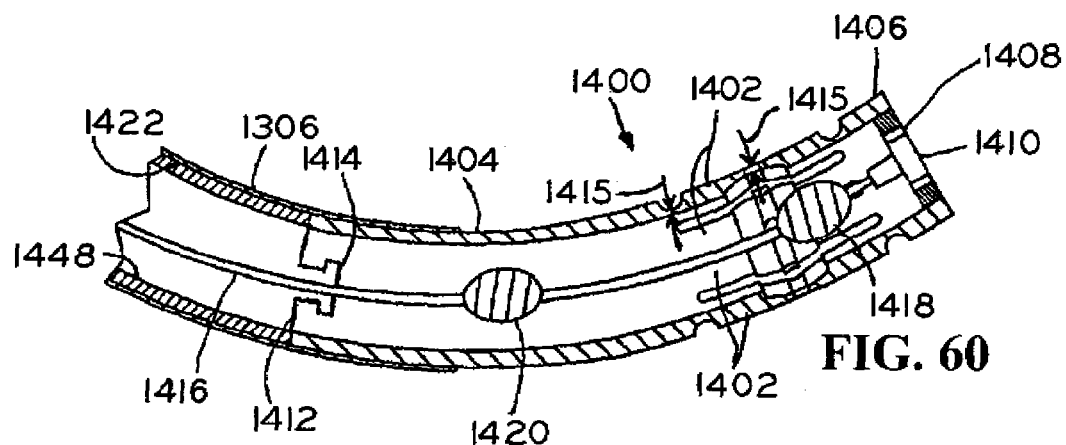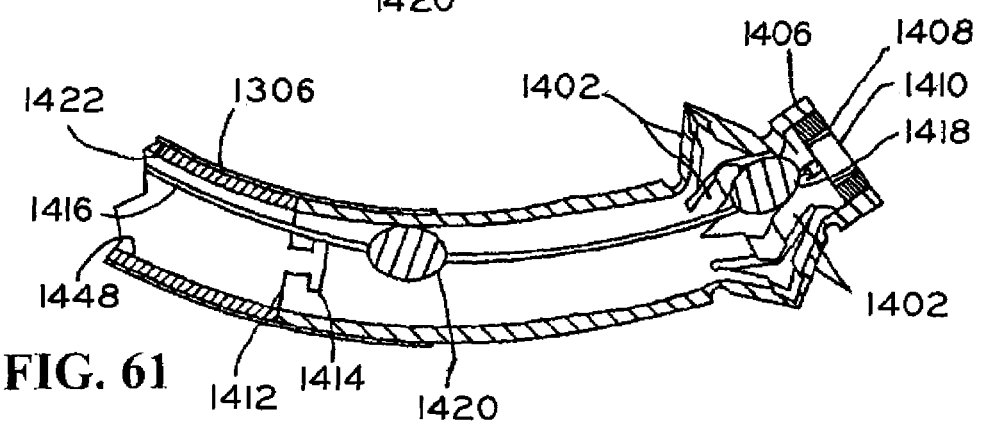
FIG. 58  FIG. 59
FIG. 60
FIG. 61

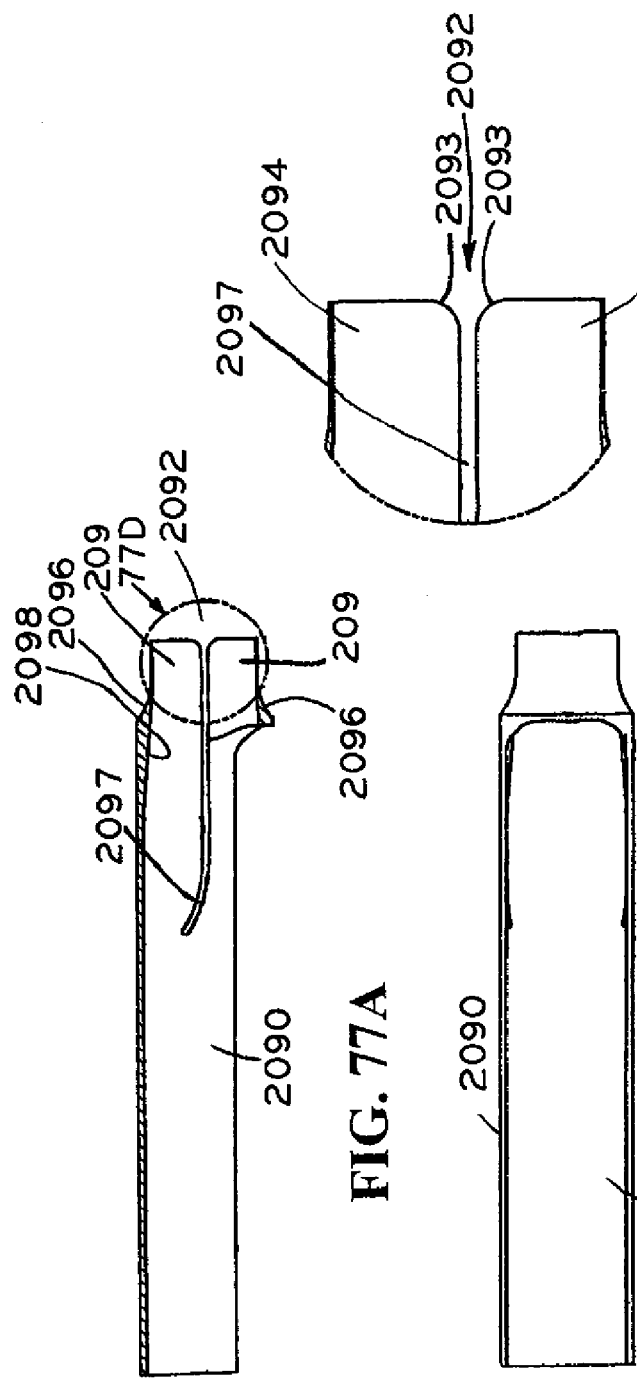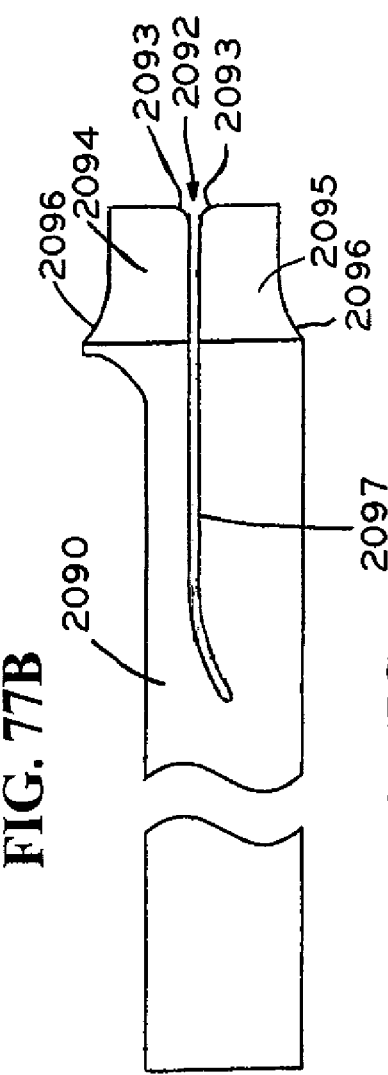
FIG. 77A
FIG. 77B
FIG. 77C
FIG. 77D

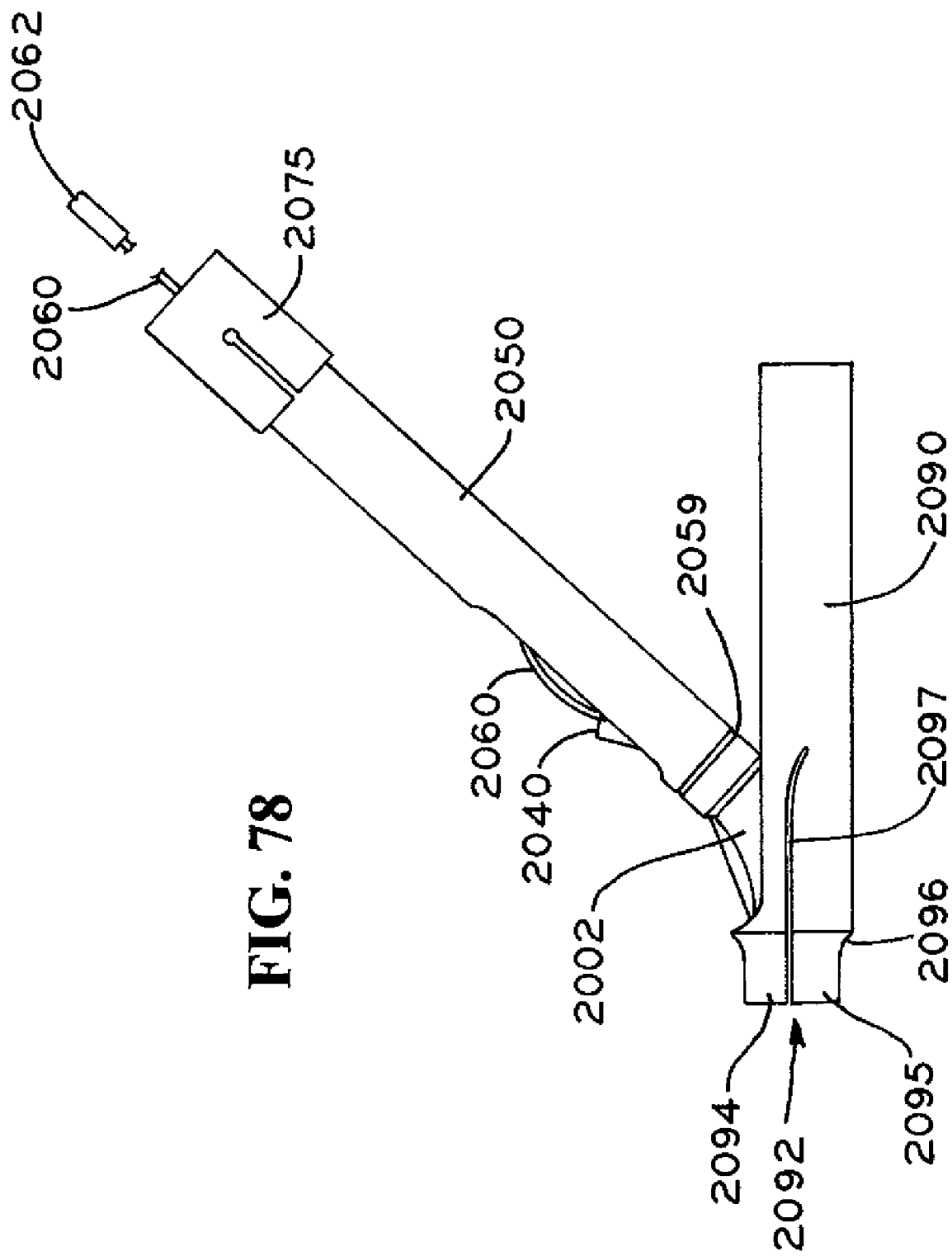

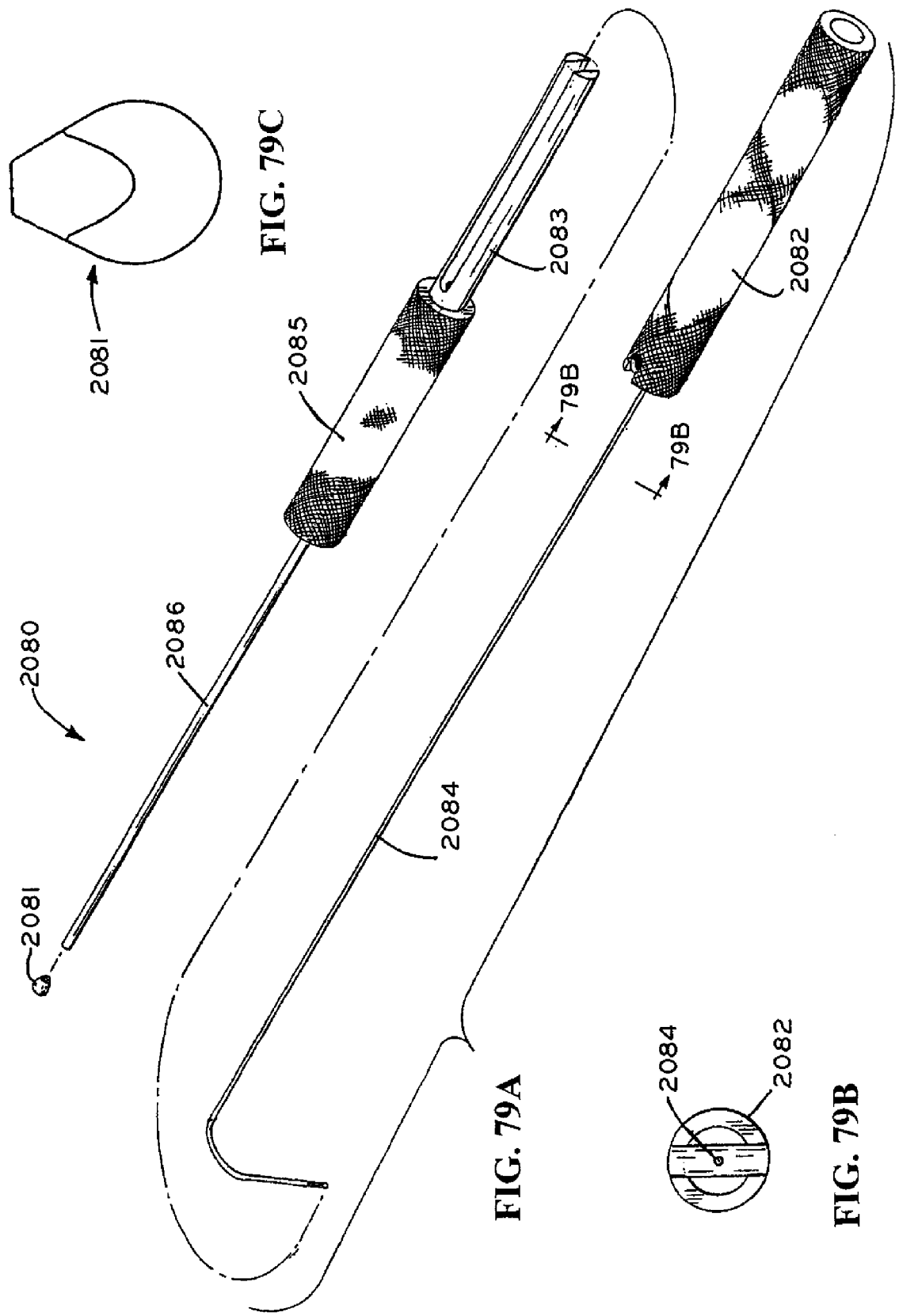

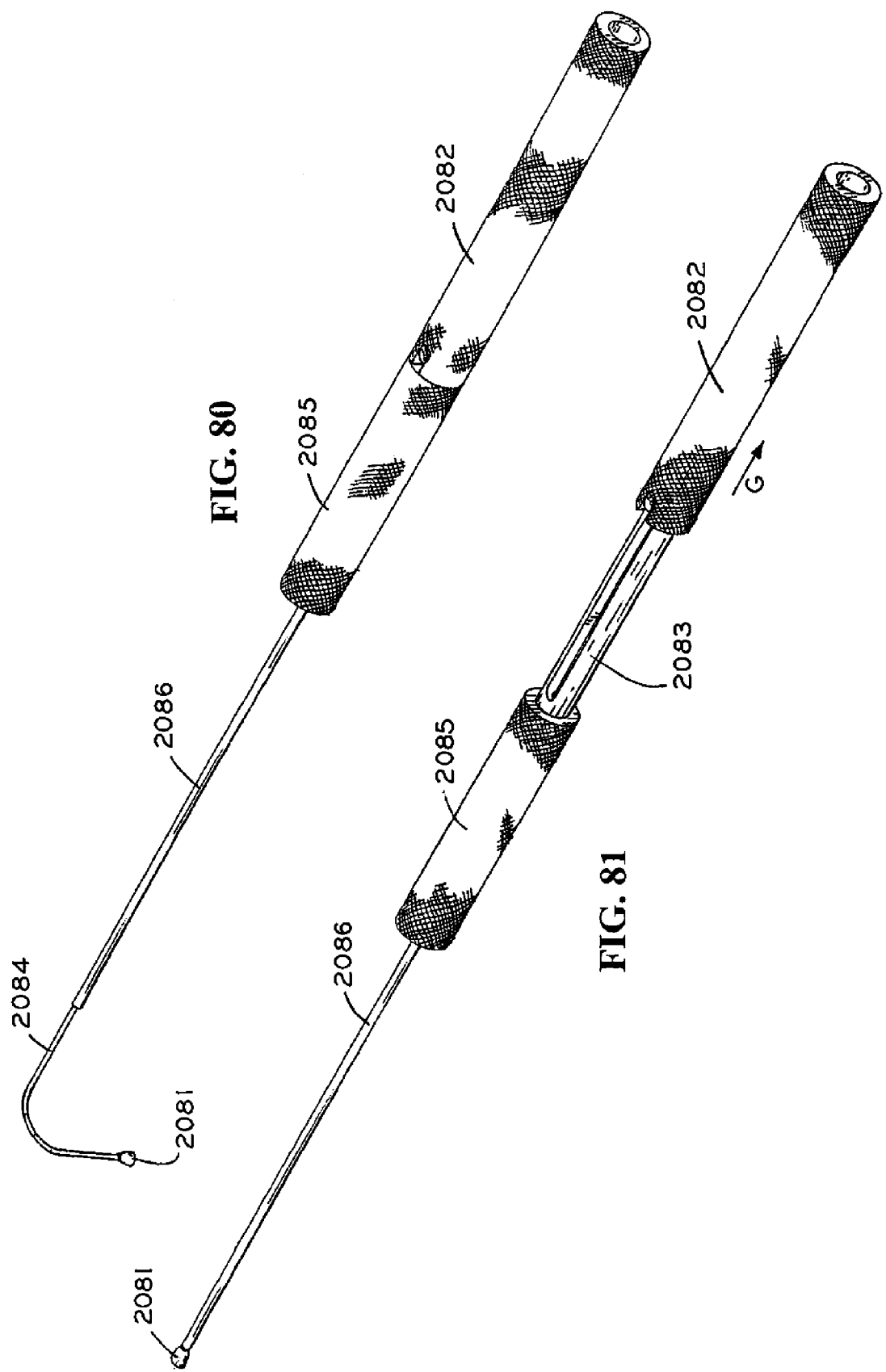

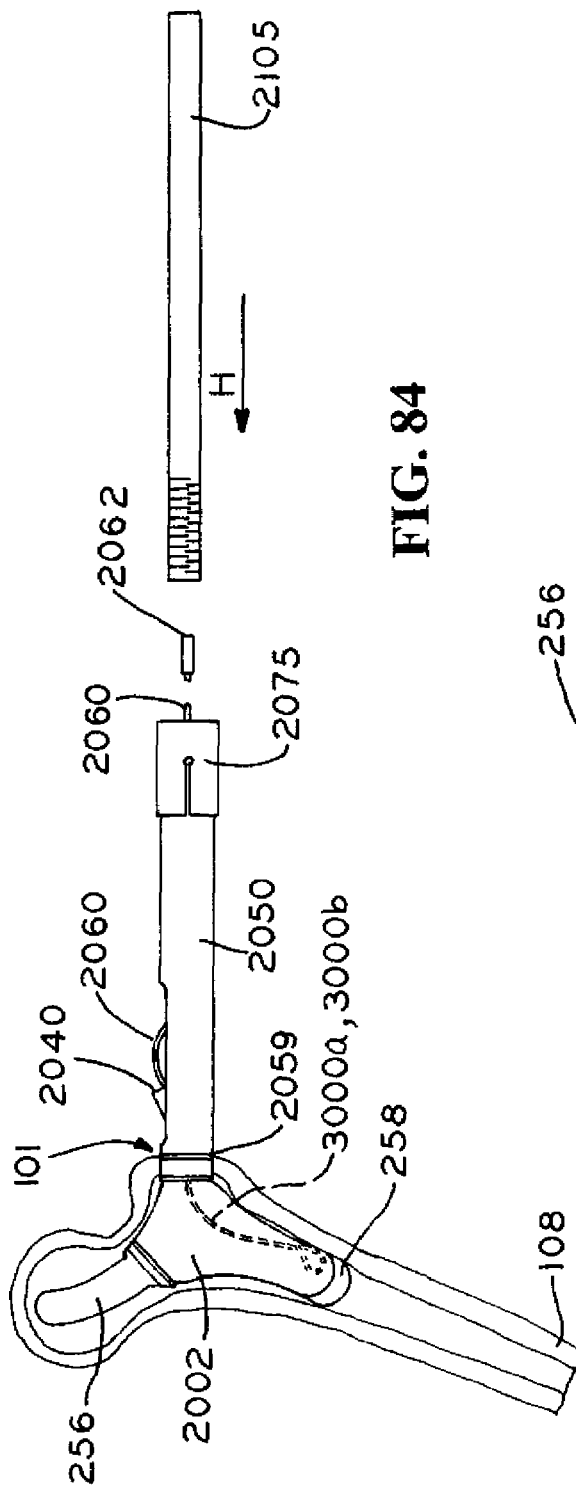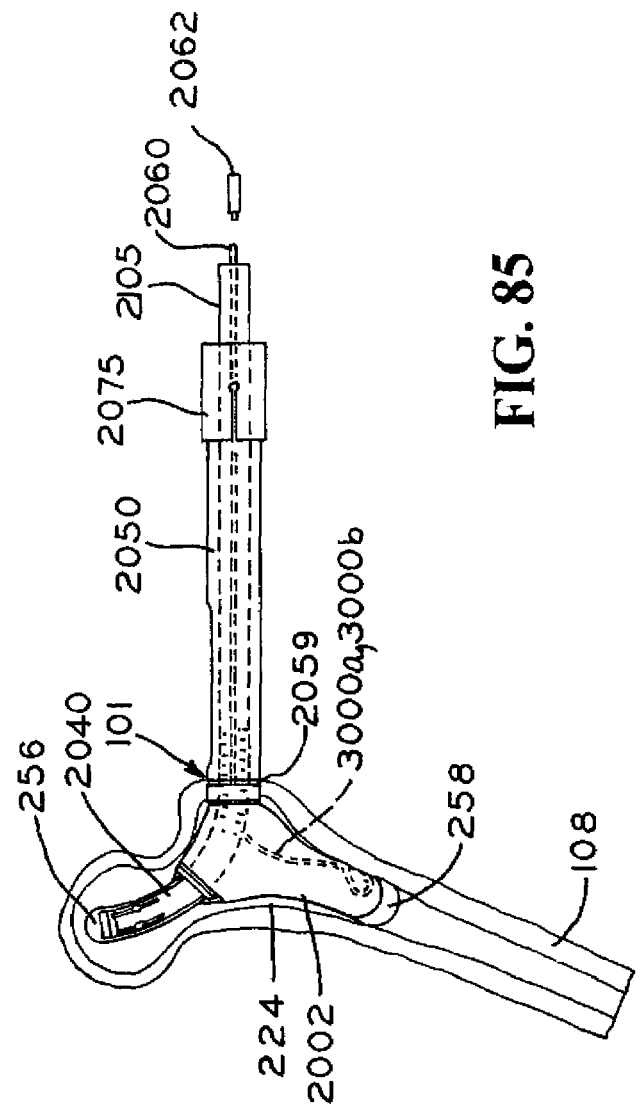
FIG. 84
FIG. 85

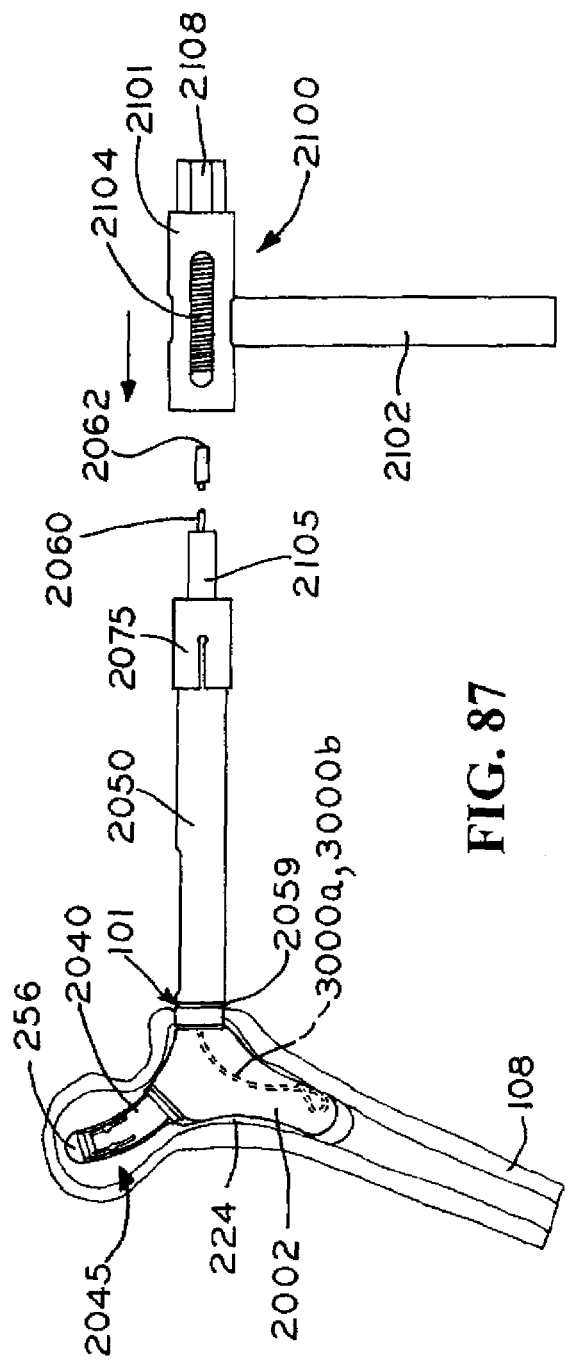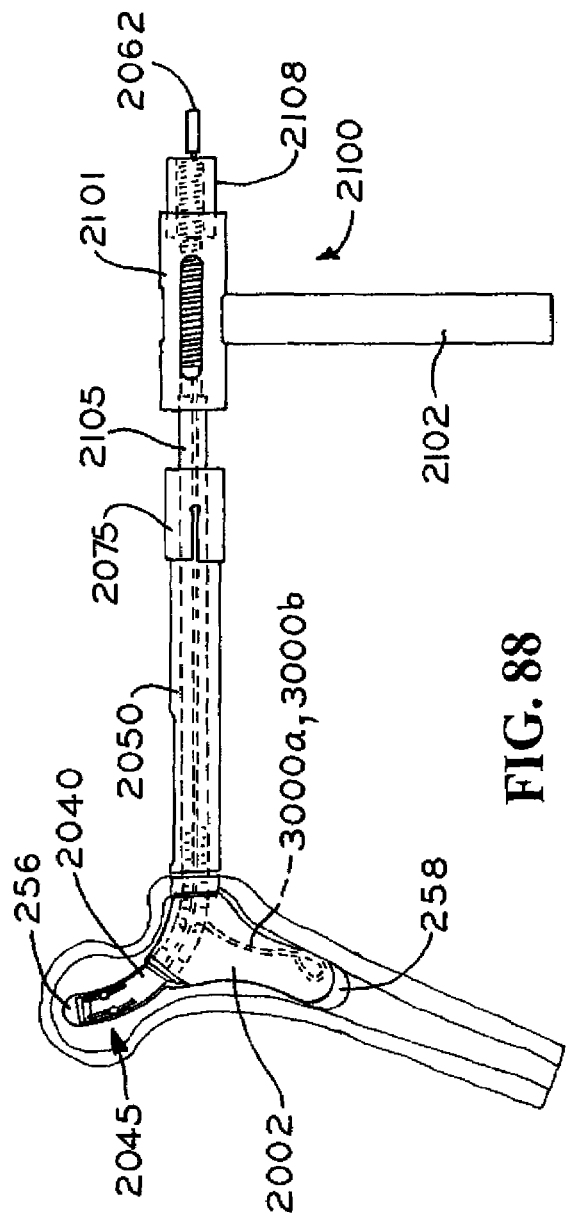

METHOD AND APPARATUS FOR REDUCING FEMORAL FRACTURES

CROSS REFERENCE TO RELATED APPLICATIONS

This application claims the benefit under Title 35, U.S.C. § 119(e) of U.S. Provisional Patent Application Ser. No. 60/621,487, entitled Transformation Technology Hip Fracture Fixation Device and Method for the Treatment of Hip Fractures, filed Oct. 22, 2004, and U.S. Provisional Patent Application Ser. No. 60/654,481, entitled Method and Apparatus for Reducing Femoral Fractures, filed Feb. 18, 2005.

This application is a continuation-in-part of prior U.S. patent application Ser. No. 11/061,898, filed Feb. 18, 2005, which is a continuation-in-part of prior U.S. patent application Ser. No. 10/358,009, filed Feb. 4, 2003, which is a continuation-in-part of prior U.S. patent application Ser. No. 10/266,319, filed Oct. 8, 2002, which is a continuation-in-part of prior U.S. patent application Ser. No. 10/155,683, filed May 23, 2002, which is a continuation-in-part of prior U.S. patent application Ser. No. 09/520,351, filed Mar. 7, 2000, now U.S. Pat. No. 6,447,514.

This application hereby expressly incorporates by reference herein the entire disclosures of U.S. Provisional Patent Application Ser. No. 60/654,481, filed Feb. 18, 2005; U.S. Provisional Patent Application Ser. No. 60/621,487, filed Oct. 22, 2004; U.S. patent application Ser. No. 11/061,898, filed Feb. 18, 2005; U.S. patent application Ser. No. 10/358,009, filed Feb. 4, 2003; U.S. patent application Ser. No. 10/266,319, filed Oct. 8, 2002; U.S. patent application Ser. No. 10/155,683, filed May 23, 2002; U.S. patent application Ser. No. 09/520,351, filed Mar. 7, 2000, now U.S. Pat. No. 6,447,514; and the Zimmer® MIS™ Hip Fixation Device Surgical Technique brochure, ©2004.

BACKGROUND

1. Field of the Invention

The present invention relates to a method and apparatus for treating hip fractures, and, more particularly, to a method and apparatus for reducing femoral fractures utilizing a minimally invasive procedure.

2. Description of the Prior Art

Current procedures utilized to reduce hip fractures generally utilize a side plate and hip screw combination, i.e., a bone plate affixed to a lateral aspect of the femur and having a hip screw operably connected thereto, with the hip screw extending into the femoral head. To properly implant the bone plate and hip screw, a surgeon must dissect an amount of muscle to expose the femur and operably attach the bone plate to the femur. In particular, the bone plate and hip screw combination surgery typically requires an incision of about 10-12 cm through the skin and muscle, for example, the quadriceps, to expose the femur. While this approach provides surgeons with an excellent view of the femoral bone surface, a more minimally invasive procedure is desired.

SUMMARY

The present invention provides an improved method and apparatus for reducing a hip fracture utilizing a minimally invasive procedure. A femoral implant in accordance with the present invention achieves intramedullary fixation as well as fixation into the femoral head. To optimally position the femoral implant, a minimally invasive incision is aligned with the greater trochanter and the wound is developed to expose the greater trochanter. Various reamers in accordance with the present invention are utilized to prepare a cavity in the femur extending from the greater trochanter into the femoral head and further extending from the greater trochanter into the intramedullary canal of the femur.

In one form thereof, the present invention provides an orthopedic implant for implantation into a cavity formed within an anatomical structure including a bag including a fill access providing access to an interior of the bag; and a structural support disposed at least partially within the bag.

In another form thereof, the present invention provides an orthopedic implant assembly for implanting an orthopedic implant into a cavity formed within an anatomical structure including an orthopedic implant, the orthopedic implant including a bag including a fill access providing access to an interior of the bag; and a structural support disposed at least partially within the bag, the structural support including first engagement structure; and an implant insertion tool including second engagement structure engageable with the first engagement structure, the implant insertion tool including at least one passage which is placed in fluid communication with the fill access of the bag upon engagement of the first engagement structure with the second engagement structure.

BRIEF DESCRIPTION OF THE DRAWINGS

The above mentioned and other features and objects of this invention, and the manner of attaining them, will become more apparent and the invention itself will be better understood by reference to the following description of exemplary embodiments of the invention taken in conjunction with the accompanying drawings, wherein:

FIG. 17 is a perspective view of a combination reamer;

FIG. 18 is a cross-sectional view of the combination reamer of FIG. 20, taken along line 18-18 of FIG. 20, further illustrating the reaming selector in a swivel reaming prevention position;

FIG. 19 is a cross-sectional view of the combination reamer of FIG. 20, taken along line 18-18 of FIG. 20, further illustrating the reaming selector in a swivel reaming allowance position;

FIG. 20 is a cross-sectional view of the combination reamer of FIG. 17, taken along line 20-20 of FIG. 17;

FIG. 22 is a partial sectional view of a telescoping reamer, further illustrating the telescoping reamer inserted in the femur of the patient of FIG. 1;

FIG. 23 is a partial sectional view of the telescoping reamer of FIG. 22, further illustrating use of the telescoping reamer to form the femoral head arm;

FIG. 35 is a plan view of a portion of the flexible guide shaft of the flexible reamer of FIG. 30;

FIG. 36 is a plan view of a lock plate of the flexible reamer of FIG. 30;

FIG. 37 is a plan view the main body housing of the flexible reamer of FIG. 30;

FIG. 47 is a perspective view of an implant bag according to an alternative embodiment;

FIG. 47A is a perspective view of the implant bag of FIG. 47;

FIG. 48 is a sectional view of the implant bag of FIG. 47, taken along line 48-48 of FIG. 47;

FIG. 49A is a cross-sectional view of a portion of the implant of FIG. 45;

FIG. 49B is a cross-sectional view of the implant of FIG. 49A, taken along line 49B-49B of FIG. 49A;

FIG. 49C is a cross-sectional view of the implant of FIG. 49A, taken along line 49C-49C of FIG. 49A;

FIG. 49D is an end perspective view of the implant of FIG. 49A;

FIG. 50 is a perspective view of the implant of FIG. 45 coupled together with an insertion instrument including an injection tube;

FIG. 51 is a perspective view of the injection tube of FIG. 50;

FIG. 52 is an end view of the distal end of the injection tube of FIG. 51, taken along line 52-52 of FIG. 51;

FIG. 53A is a plan view of a clip of the present invention;

FIG. 53B is a fragmentary view of a portion of the clip of FIG. 53A;

FIG. 53C is a fragmentary view of a portion of the clip of FIG. 53A;

FIG. 53D is a side view of the clip of FIG. 53A;

FIG. 54A is a plan view of an alternative embodiment implant, further illustrating an implant utility tube associated therewith;

FIG. 54B is an end view of the distal end of the implant utility tube of FIG. 54A, taken along line 54B-54B of FIG. 54A;

FIG. 54C is a fragmentary view of a portion of the implant of FIG. 54A;

FIG. 54D is a plan view of the implant of FIG. 54A coupled with the implant utility tube;

FIG. 55 is a partial cross-sectional view of a portion of a lag according to one embodiment;

FIG. 56 is a perspective view of the lag of FIG. 55, further illustrating an actuation mechanism;

FIG. 57 is a partial cross-sectional view of the portion of the lag of FIG. 55, further illustrating the fingers of the lag at least partially deployed;

FIG. 58 is a perspective view of a lag according to an alternative embodiment;

FIG. 59 is a cross-sectional view of a portion of the lag of FIG. 58, taken along line 59-59 of FIG. 58;

FIG. 60 is a cross-sectional view of the lag of FIG. 58;

FIG. 61 is a cross-sectional view of the lag of FIG. 58, further illustrating the fingers of the lag at least partially deployed;

FIG. 77A is a partial sectional view of the insertion sleeve, further illustrating the tapered interior;

FIG. 77B is a plan view of the insertion sleeve of FIG. 77A;

FIG. 77C is a plan view of the insertion sleeve of FIG. 77A;

FIG. 77D is a fragmentary view of a portion of the insertion sleeve of FIG. 77A;

FIG. 78 is a plan view of the assembly of FIG. 75 inserted within the insertion sleeve of FIG. 77A;

FIG. 79A is an exploded perspective view of a deployment instrument;

FIG. 79B is a cross-sectional view of a portion of the deployment instrument of FIG. 79A, taken along line 79B-79B of FIG. 79A;

FIG. 79C is a plan view of the deployment end of the deployment instrument of FIG. 79A;

FIG. 80 is an assembled perspective view of the deployment instrument of FIG. 79A, further illustrating the deployment wire extended from the deployment wire guide;

FIG. 81 is an assembled perspective view of the deployment instrument of FIG. 79A, further illustrating the deployment wire retracted within the deployment wire guide;

FIG. 84 is a plan view of a flexible lag cable, further illustrating the insertion of the flexible lag cable into the implant utility tube, spring guide, and collet nut combination;

FIG. 85 is a plan view of the assembly of FIG. 84, further illustrating the complete insertion of the flexible lag cable of FIG. 84 into the implant utility tube;

FIG. 87 is a perspective view of a lag actuator according to an alternative embodiment, further illustrating the relationship to the implant utility tube assembly and the femur;

FIG. 88 is a perspective view of the lag actuator of FIG. 87, further illustrating the lag actuator coupled to the actuation cable;

Figure 1:
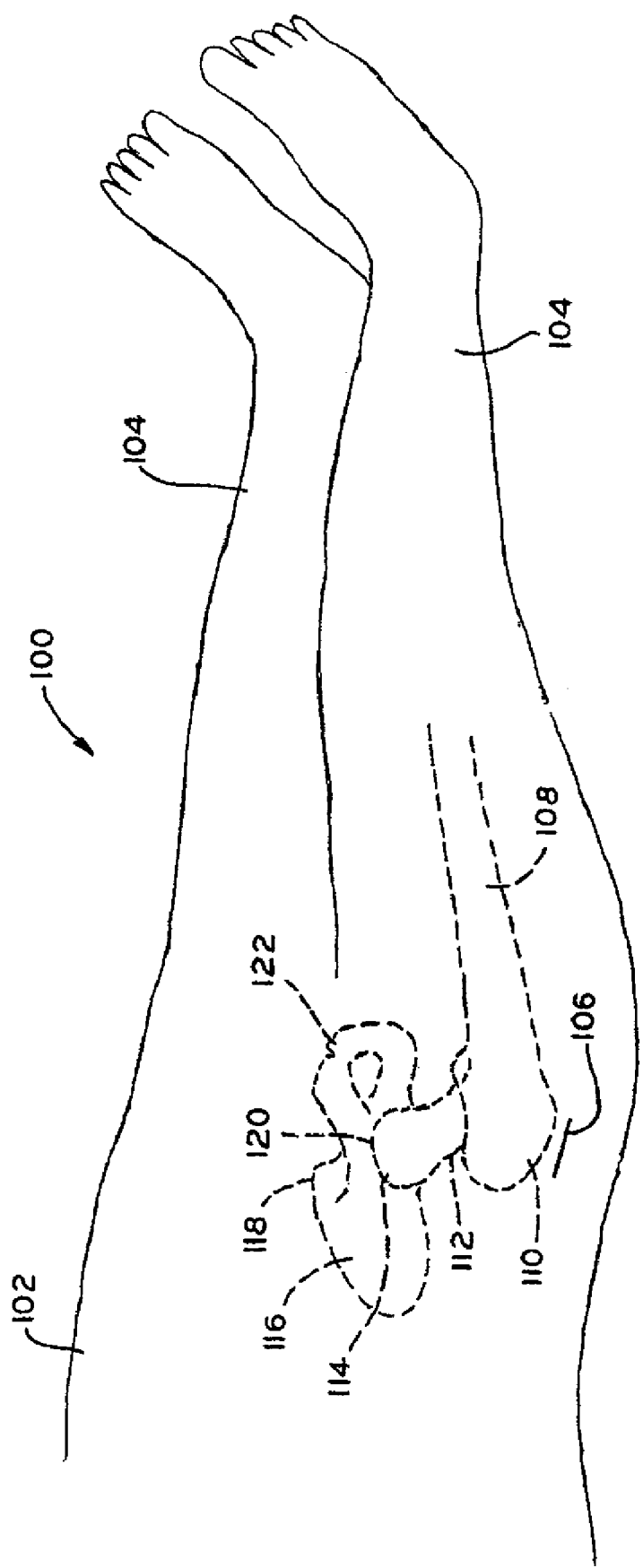
FIG. 1 is a perspective view of a hip joint area of a human patient showing the femur and a portion of the pelvis in dashed lines.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention, and such exemplifications are not to be construed as limiting the scope of the invention in any manner.

DETAILED DESCRIPTION

The embodiments disclosed below are not intended to be exhaustive or limit the invention to the precise forms disclosed in the following detailed description. Rather, the embodiments are chosen and described so that others skilled in the art may utilize their teachings.

The description below may include reference to the following terms: anterior (at or near the front of the body, as opposed to the back of the body); posterior (at or near the back of the body, as opposed to the front of the body); lateral (at or near the left or right side of the body, farther from the midsagittal plane, as opposed to medial); medial (in the middle, at or near the midsagittal plane, as opposed to lateral); proximal (nearest the surgeon, as opposed to distal); and distal (further from the surgeon, as opposed to proximal).

I. Introduction

The present invention provides an improved method, devices, and surgical instruments for reducing a hip fracture utilizing a minimally invasive procedure. A femoral implant in accordance with the present invention achieves intramedullary fixation as well as fixation into the femoral head. To optimally position the femoral implant, a minimally invasive incision is aligned with the greater trochanter and the wound is developed to expose the greater trochanter. Various reamers in accordance with the present invention are utilized to prepare a cavity in the femur extending from the greater trochanter into the femoral head and further extending from the greater trochanter into the intramedullary canal of the femur.

II. Surgical Technique

A. Patient Positioning and Fracture Reduction

After anesthesia is administered, patient 100 is placed in a supine position, shown in FIG. 1, on an operating table (not shown). The affected hip may be elevated to gain exposure and access to greater trochanter 110 by using a roll or bump (not shown). Fracture and traction tables may be used to assist with patient positioning and alignment of the fracture site. It is important to reduce the fracture before proceeding with creation of the cavity and placement of the implant, as described below. Reduction instrumentation (not shown), i.e., reduction forceps, etc., should be positioned away from the hip area to allow access for exposure. Additional provisional stabilization with Kirschner Wires (not shown) may be required for some fractures. Fluoroscopy may be used to confirm reduction, as described below.

FIG. 1 generally illustrates torso 102 and legs 104 of patient 100. FIG. 1 further illustrates the general bone structures comprising the hip joint including pubis 122, anterior superior iliac spine 118, ilium 116, acetabulum 120, and femur 108. Femur 108 includes, inter alia, greater trochanter 110, femoral neck 112, and femoral head 114.

Figure 2:
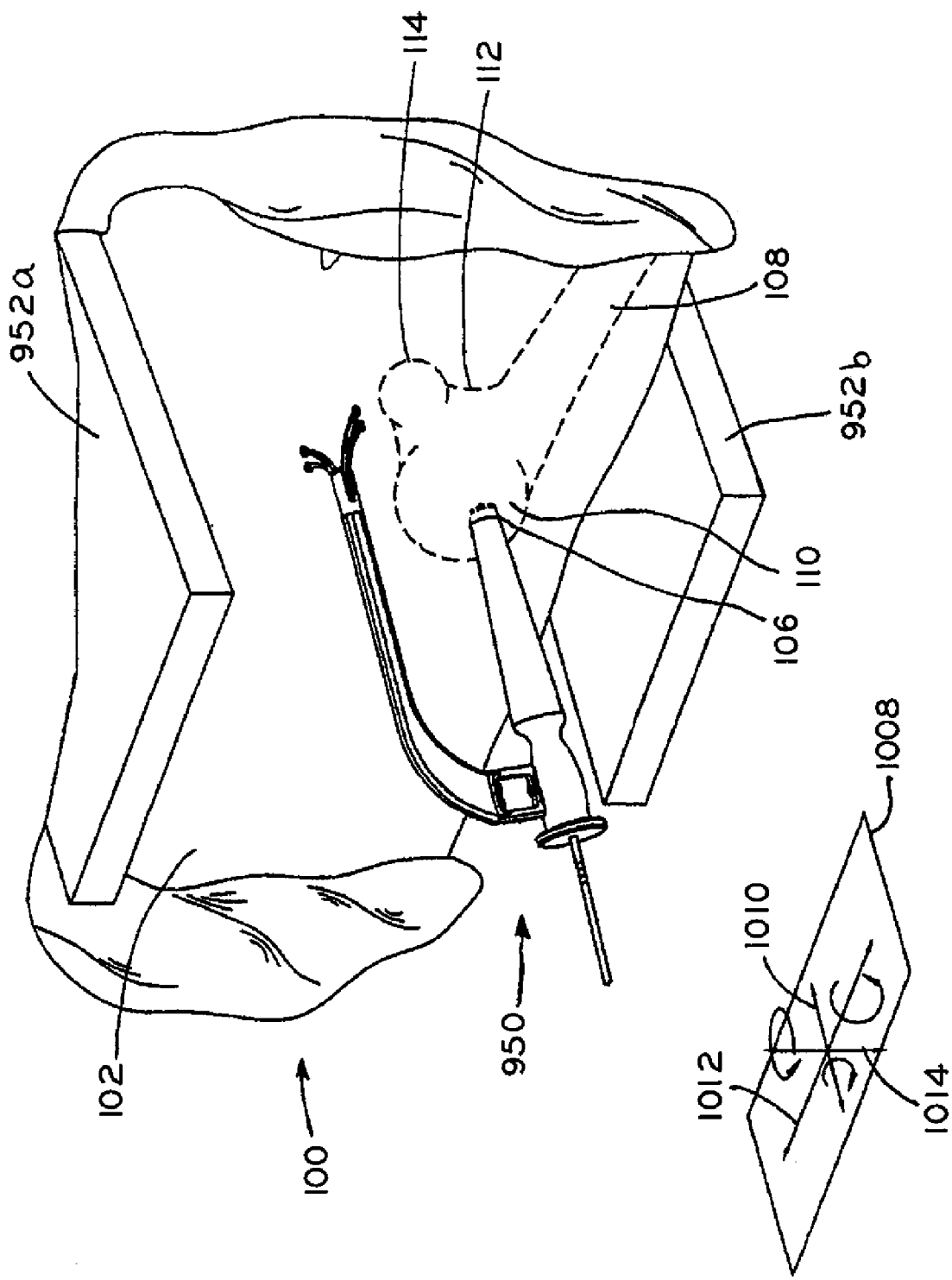
FIG. 2 is a perspective view of a hip joint area of the human patient of FIG. 1, further illustrating the use of an alignment guide and fluoroscope.

Referring now to FIG. 2, torso 102 of patient 100 is positioned between upper fluoroscopic component 952*a* and lower fluoroscopic component 952*b* of a C-arm fluoroscope or other device suitable for imaging femur 108. Fluoroscopic components 952*a* and 952*b* are positioned parallel to coronal femoral plane 1008 in order to provide imagery that aids in the proper positioning of instruments herein described. Specifically, coronal femoral plane 1008 is defined as the plane which centrally intersects greater trochanter 110 and the intramedullary shaft of femur 108. Coronal femoral plane 1008 is selected as the reference plane for fluoroscopic imagery because the below-described implant cavity in femur 108 is, in part, oriented relative to coronal femoral plane 1008, and the below-described instruments include radiopaque features designed for tracking by a fluoroscopic imagery device which is oriented parallel to coronal femoral plane 1008. Although described throughout as using fluoroscopic imagery, other imagery methods may be utilized such as computed tomography (CT) scanning or magnetic resonance imaging (MRI).

B. Incision and Exposure

Figure 3:
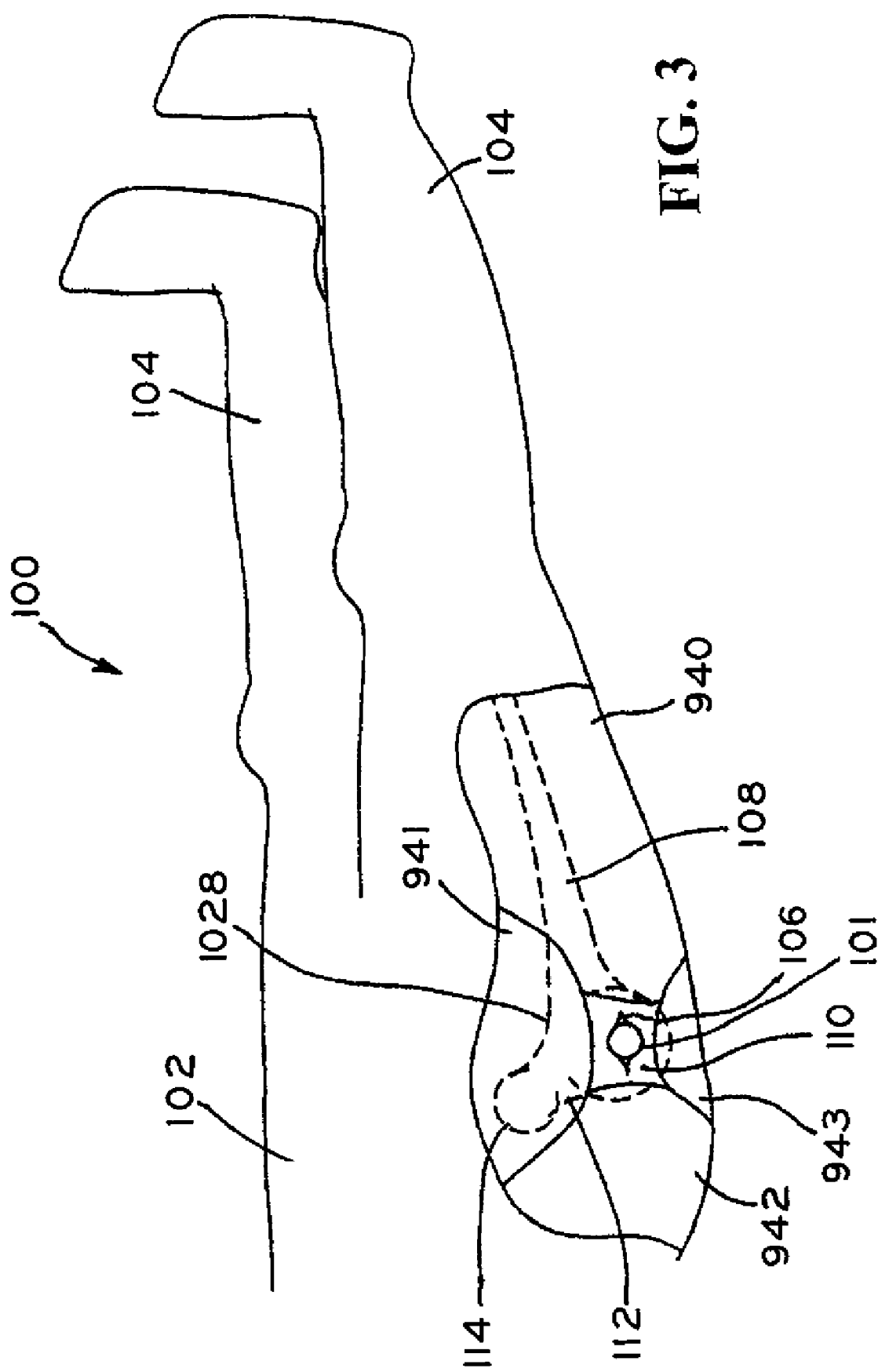
FIG. 3 is a perspective view of a hip joint area of the human patient of FIG. 1, further illustrating the underlying muscles and the greater trochanter access.

Referring now to FIGS. 1 and 3, incision 106 may be generally aligned with greater trochanter 110. Incision 106 generally measures about 2-5 centimeters (0.8-2 inches) and is made directly lateral and perpendicular to the face of greater trochanter 110. Incision 106 should extend from the tip of greater trochanter 110 distally along its length and should extend through the skin, fat and fascia to the bone surface of greater trochanter 110. Incision 106 is preferably located generally on a plane that runs through the center of greater trochanter 110, femoral head 114 and the intramedullary shaft of femur 108. Retractors (not shown) may be used to visualize the greater trochanter area. Incision 106 may be located over a central, substantially planar portion of greater trochanter 110 that is not covered by muscle or which is covered by muscle that is not attached to the central portion of greater trochanter 110. Therefore, tissues such as quadriceps 940, iliotibial band 941, adductor 942, and gluteus 943 can be easily retracted without substantial tissue damage, shown in FIG. 3.

C. Alignment Guide and Pin Insertion

Referring again to FIG. 2, after forming incision 106, a portion of alignment guide 950 may be positioned through incision 106 and down to the bone surface of greater trochanter 110. Alignment guide 950 is generally used to provide the surgeon with a guide for forming access 101 (FIG. 3). Components of alignment guide 950 provide radiopaque features for orienting alignment guide 950 relative to coronal femoral plane 1008 and other aspects of femur 108. The structure and operation of alignment guide 950 are fully described in U.S. patent application Ser. No. 11/061,898, filed Feb. 18, 2005, the disclosure of which is incorporated herein by reference. Alternatively, an alignment device (not shown) may be used to provide guidance for the formation of access 101, such as alignment device 156, the structure and operation of which are fully described in U.S. patent application Ser. No. 10/155,683, filed May 23, 2002, the disclosure of which is incorporated herein by reference.

D. Creating the Entry Portal

Figure 4:
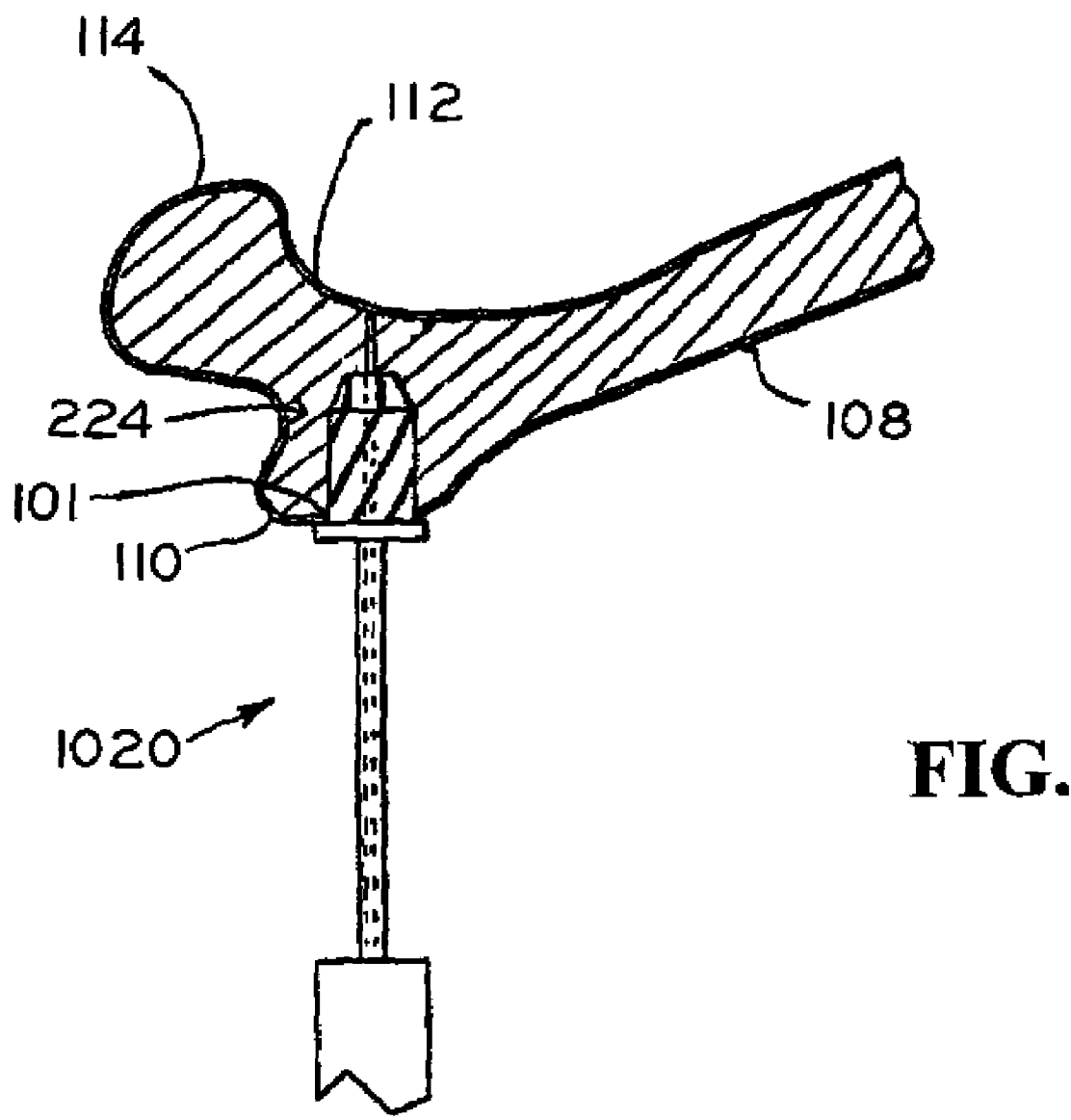
FIG. 4 is a perspective view of a plunge reamer inserted into the femur of the human patient of FIG. 1.
Figure 5:
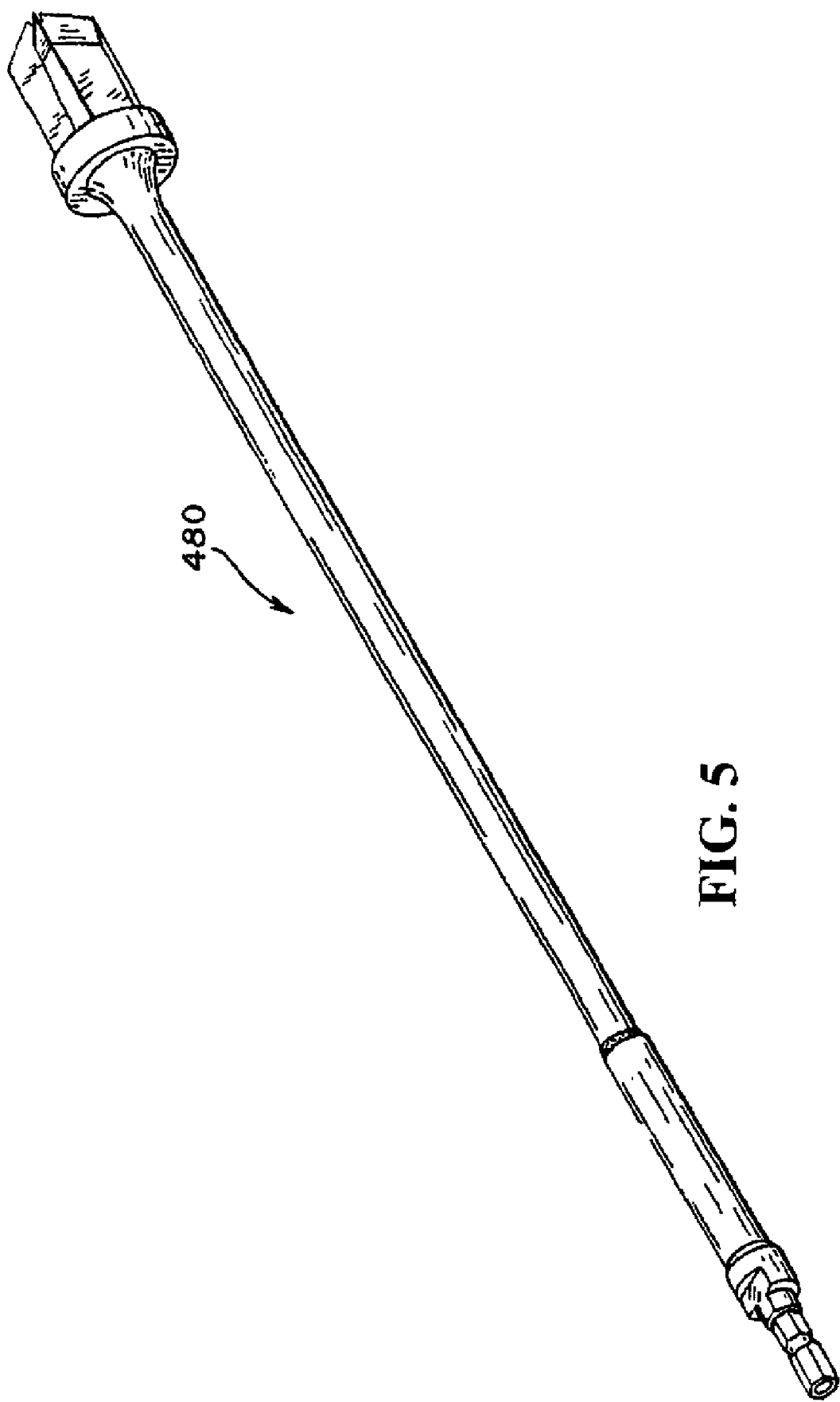
FIG. 5 is a perspective view of a plunge reamer according to an alternative embodiment.
Figure 6:
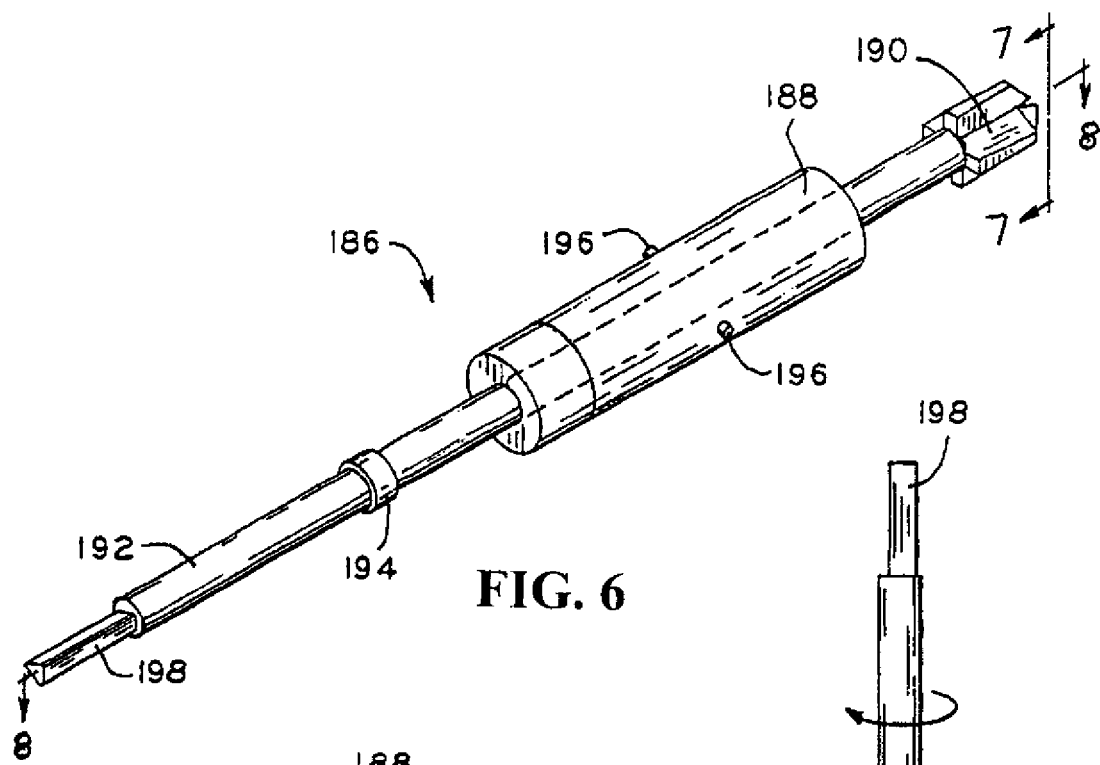
FIG. 6 is a perspective view of a straight reamer.
Figure 7:
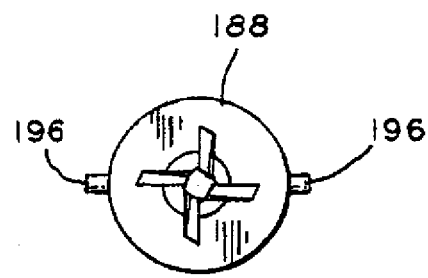
FIG. 7 is an end view of the distal end of the straight reamer of FIG. 6, taken along line 7-7 of FIG. 6.
Figure 8:
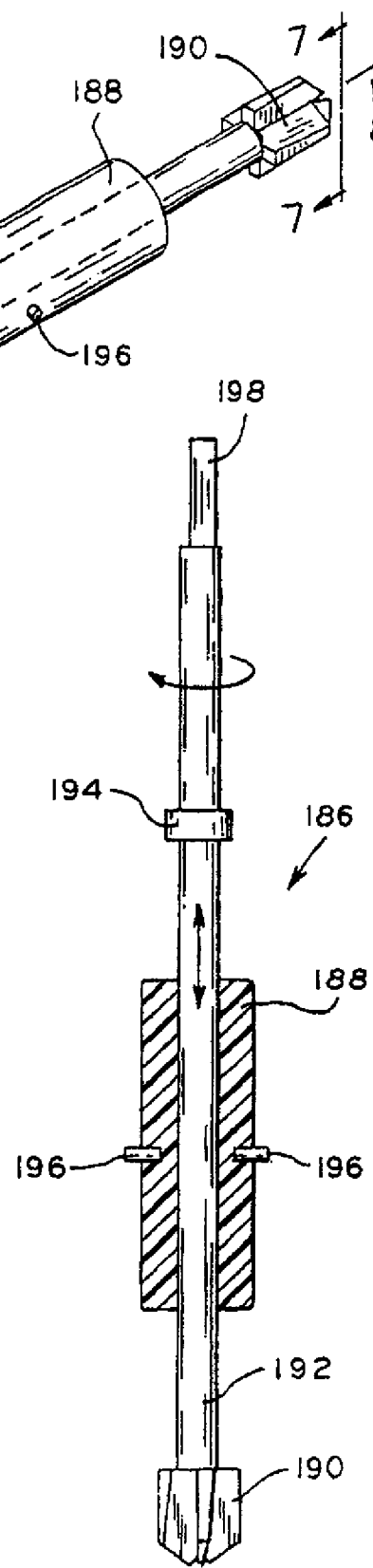
FIG. 8 is a partial sectional view through the straight reamer of FIG. 6, taken along line 8-8 of FIG. 6.

Referring now to FIG. 4, plunge reamer 1020 may be utilized to form access 101 and cavity 224 in femur 108. In general, access 101 forms a cylindrical access hole extending from greater trochanter 110 into femur 108 and cavity 224 is a substantially conical and diverging-type opening which extends access 101 further into femur 108. The structure and operation of plunge reamer 1020 are fully described in U.S. patent application Ser. No. 11/061,898, filed Feb. 18, 2005, the disclosure of which is incorporated herein by reference. In an alternative embodiment shown in FIG. 5, plunge reamer 480 may be used to form access 101 and cavity 224. The structure and operation of plunge reamer 480 are fully described in U.S. patent application Ser. No. 10/155,683, filed May 23, 2002, the disclosure of which is incorporated herein by reference. Reamers 1020 and 480 may be used to provide the initial entry point, i.e., access 101, for the femoral implant, as described below.

Figure 9:
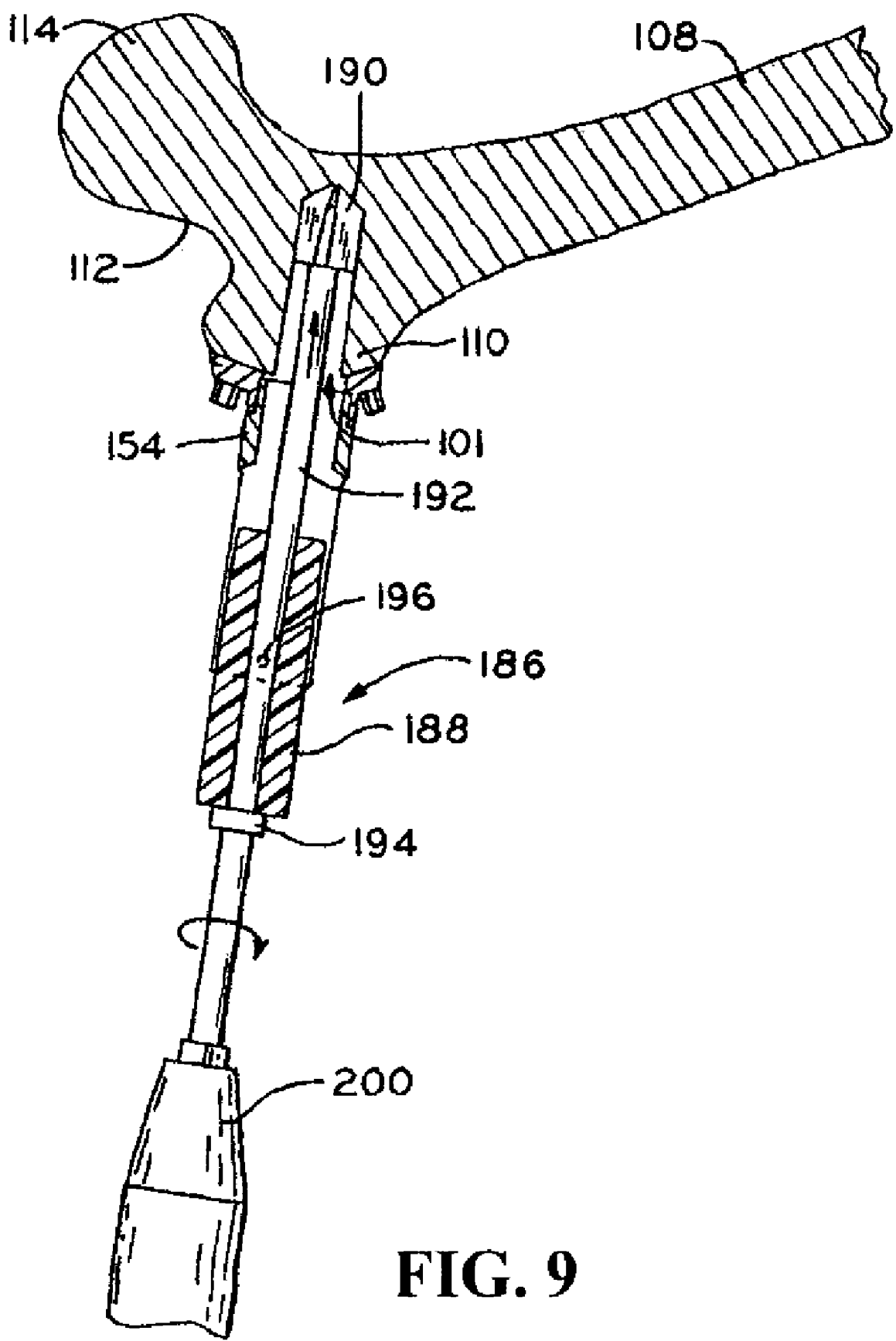
FIG. 9 is a partial perspective view of the straight reamer of FIG. 6, further illustrating use of the straight reamer to create the access in the greater trochanter.
Figure 10:
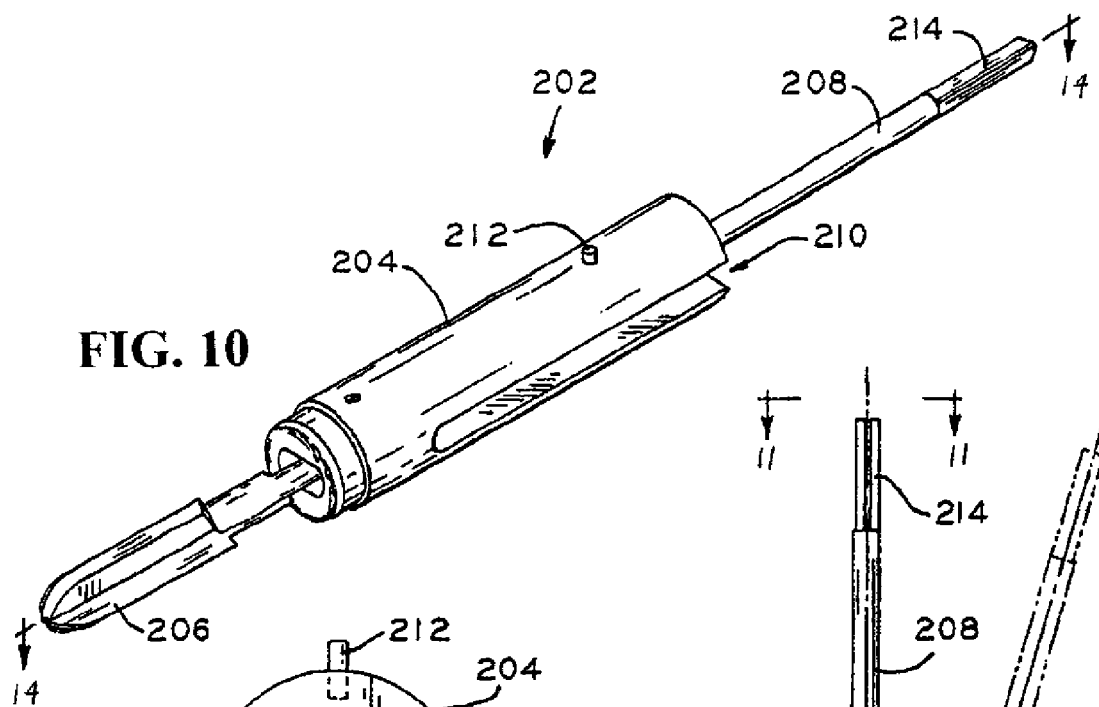
FIG. 10 is a perspective view of a swivel reamer.
Figure 11:
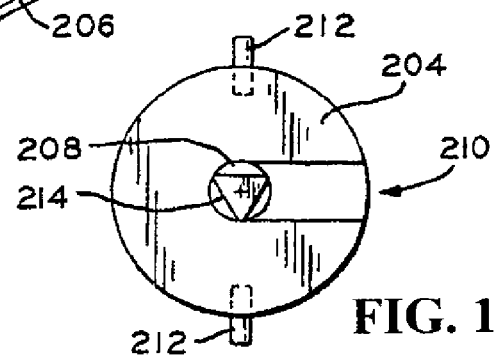
FIG. 11 is an end view of the proximal end of the swivel reamer of FIG. 14, taken along line 11-11 of FIG. 14.

Referring now to FIGS. 6-16, in an alternative embodiment, straight reamer 186, shown in FIGS. 6-9, may be used to form access 101 and swivel reamer 202, shown in FIGS. 10-16, may be used to form cavity 224. Straight reamer 186 includes straight reamer guide tube 188 surrounding straight reamer shaft 192. Straight reamer guide tube 188 is positioned intermediate straight reamer head 190 and flange 194 and is operable to move along reamer shaft 192 there between. Straight reamer guide tube 188 has an exterior geometry cooperating with the internal geometry of straight guide tube/retractor 154 (FIG. 9) and/or an angled guide tube/retractor (not shown) to provide a solid base for reaming femur 108. The structures of straight guide tube/retractor 154 and the angled guide tube/retractor are fully described in U.S. patent application Ser. No. 10/155,683, filed May 23, 2002, the disclosure of which is incorporated herein by reference. Straight reamer 186 further includes proximal end 198 adapted to be received in the chuck of a rotary motion imparting device 200 (FIG. 9). As shown in FIGS. 6-9, straight reamer guide tube 188 includes opposing bosses 196 protruding from the exterior surface thereof to cooperate with boss channels formed in the proximal end of the guide tube/retractors, as discussed in U.S. patent application Ser. No. 10/155,683.

In use and as shown in FIG. 9, straight reamer guide tube 188 is positioned within guide tube/retractor 154 with bosses 196 entering the boss channels (not shown) formed in the proximal end of guide tube/retractor 154. The engagement of bosses 196 with the boss channels prevents axial displacement of guide tube 188 relative to guide tube/retractor 154 into which it is inserted. Proximal end 198 of straight reamer 186 is actuated to provide rotational movement of reamer head 190 to form access 101 in femur 108. After achieving a predetermined reamer depth, flange 194 contacts the proximal end of guide tube 188 to limit axial displacement of reamer head 190. In one exemplary embodiment, straight reamer 186 is configured to provide a reaming depth of 1.9 centimeters (0.75 inches) into femur 108.

Figure 14:
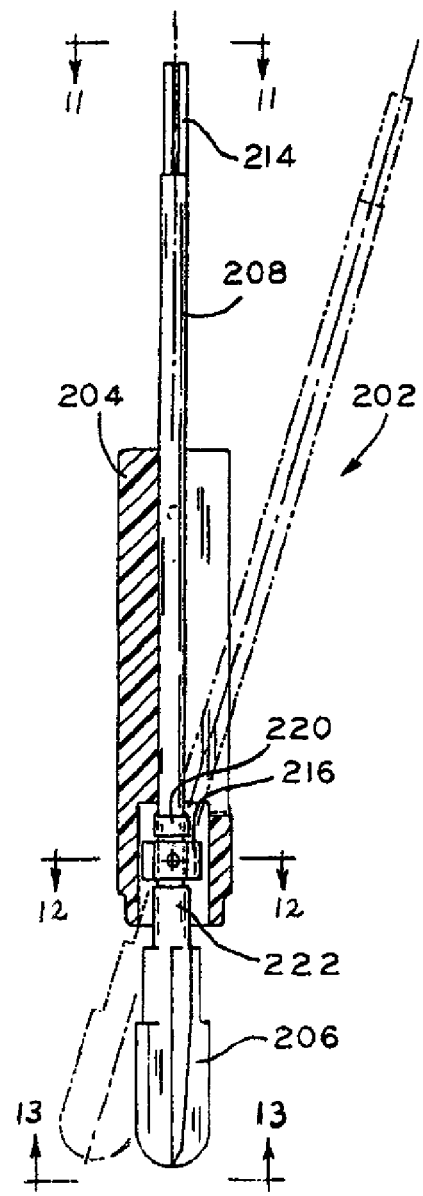
FIG. 14 is a cross-sectional view of the swivel reamer of FIG. 11, taken along line 14-14 of FIG. 11.
Figure 15:
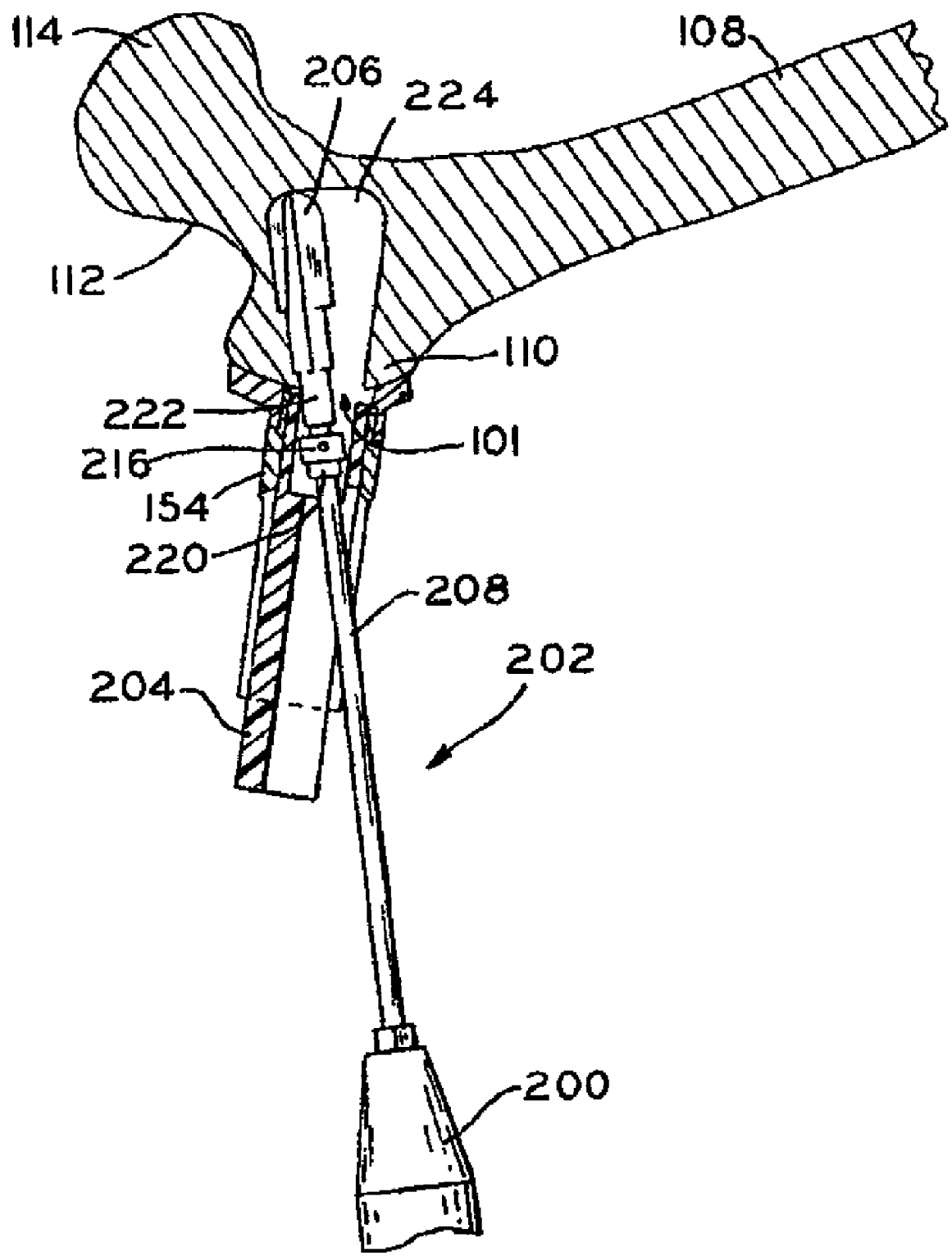
FIG. 15 is a partial sectional view of the swivel reamer of FIG. 11, further illustrating use of the swivel reamer to create a portion of the cavity in the femur.
Figure 16:
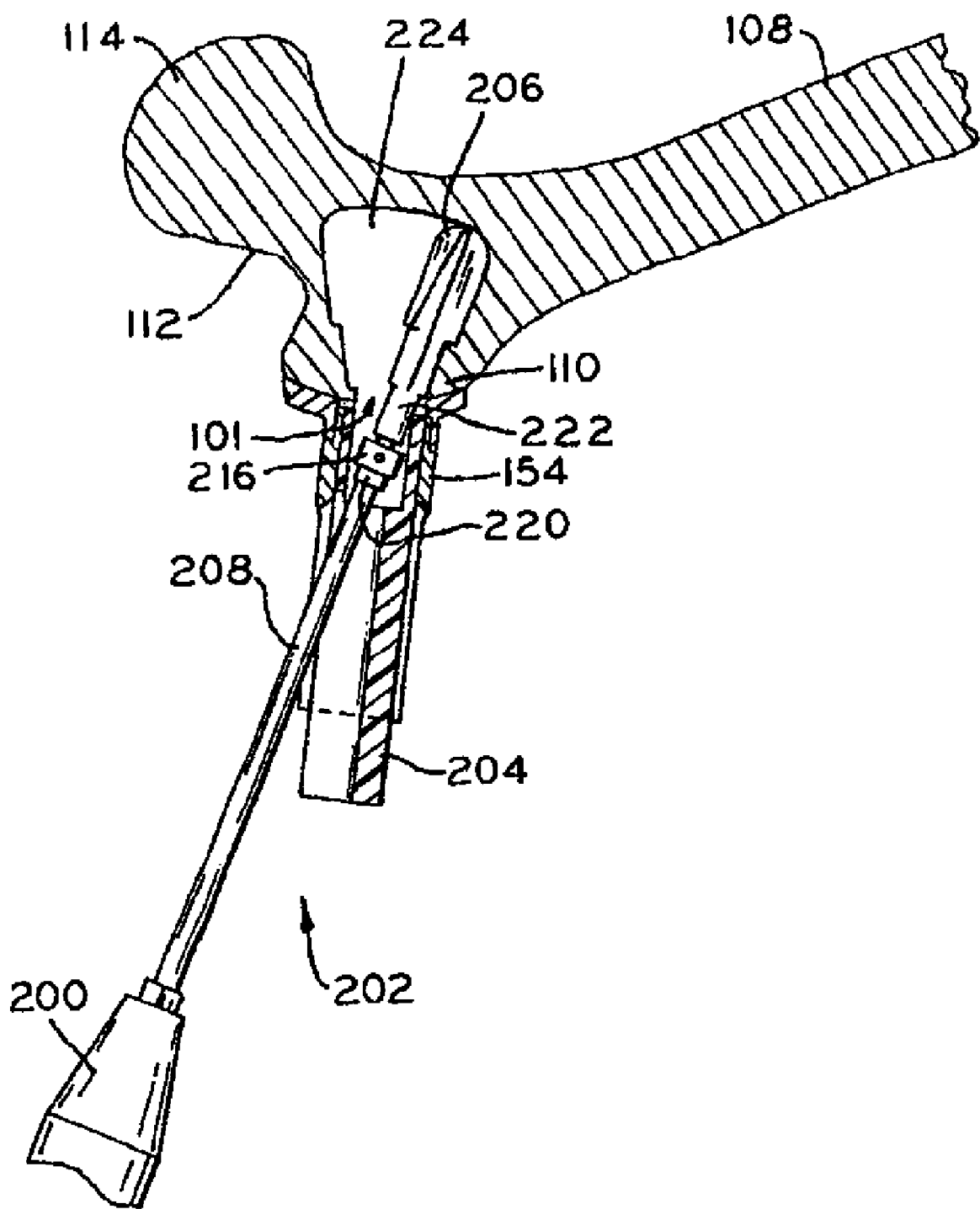
FIG. 16 is a partial sectional view of the swivel reamer of FIG. 11, further illustrating use of the swivel reamer to finish the cavity in the femur.

Swivel reamer 202, shown in FIGS. 10-16, may then be used to form cavity 224 (FIGS. 15-16). Swivel reamer 202 includes swivel reamer guide tube 204 having opposing bosses 212 protruding there from. Swivel reamer guide tube 204 includes cutout 210 operable to allow reamer shaft 208 to pivot about swivel reamer pivot 216. Similar to straight reamer 186, swivel reamer 202 includes proximal end 214 operable to connect swivel reamer 202 to the chuck of a rotary motion imparting device 200 (FIG. 15). Bosses 212 are utilized to connect swivel reamer 202 to guide tube/retractor 154 in the same manner as bosses 196 of straight reamer 186, as described above, thereby preventing axial displacement of swivel reamer 202 relative to guide tube/retractor 154.

Figure 12:
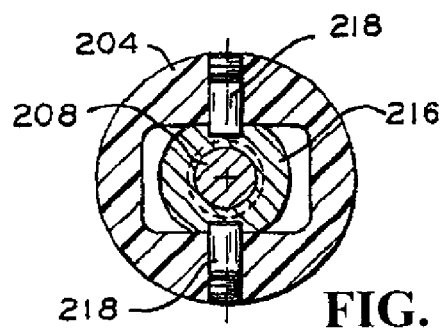
FIG. 12 is a cross-sectional view through the swivel reamer of FIG. 14, taken along line 12-12 of FIG. 14.
Figure 13:
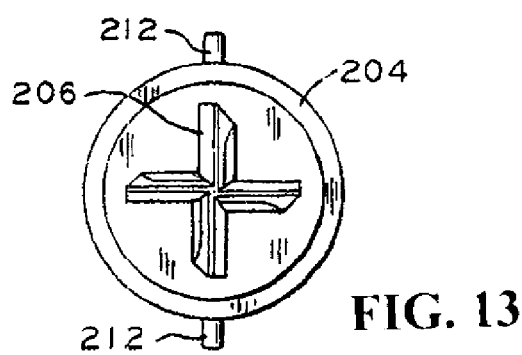
FIG. 13 is an end view of the distal end of the swivel reamer of FIG. 14, taken along line 13-13 of FIG. 14.

As shown in FIG. 12, swivel reamer pivot 216 is pivotally connected to swivel reamer guide tube 204 via pivot pins 218. As shown in FIG. 14, swivel reamer pivot 216 encircles reamer shaft 208 and abuts enlarged portion 222 of swivel reamer shaft 208 and flange 220 on opposing axial ends thereof to prevent axial displacement of swivel reamer head 206. As shown in FIG. 15, swivel reamer 202 is used to form a portion of cavity 224, i.e., forming cavity 224 as a generally conical and diverging-type cavity toward femoral head 114. As shown in FIG. 16, the orientation of swivel reamer 202 is changed to accommodate swivel reaming toward the femoral shaft to complete the reaming of cavity 224.

In another alternative embodiment shown in FIGS. 17-20, combination reamer 358 may be utilized to effect both plunge, i.e., straight reaming into the femur, as well as swivel reaming to form access 101 and cavity 224. In this embodiment, combination reamer 358 is inserted into a guide tube/retractor similar to that described above with respect to swivel reamer 202, with orientation plate 384 (FIG. 20) cooperating with one of the longitudinal channels formed in the guide tube/retractor to properly align combination reamer 358 within the guide tube/retractor. Combination reamer 358 includes reamer head 360 connected to the distal end of reamer shaft 362. Reamer shaft 362 includes flange 364 positioned toward the distal end thereof and ratchet teeth 382 formed toward the proximal end thereof. As shown in FIG. 20, reamer shaft 362 is positioned within reamer shaft tube 372 having reamer depth lock 374 formed on a proximal end thereof. Reamer depth lock 374 includes ratchet release lever 376 (FIG. 17) connected via connecting rod 378 to ratchet head 380, shown in FIG. 20. A spring is utilized to bias ratchet head 380 into engagement with selected ones of ratchet teeth 382 on reamer shaft 362. Ratchet release lever 376 is pivotally connected to reamer depth lock 374 such that actuation of ratchet release lever 376 causes outward radial movement of ratchet head 380 with respect to reamer shaft 362, thus disengaging the ratchet teeth formed in ratchet head 380 from ratchet teeth 382 and allowing for relative axial movement of reamer shaft tube 372 and reamer shaft 362. When used for plunge reaming, combination reamer 358 reaches the terminal reaming depth when the distal end of reamer shaft tube 372 contacts pivot 216'. The overall depth of plunge reaming may thus be adjusted by varying the axial displacement of reamer depth lock 374 along reamer shaft 362.

As shown in FIG. 17, combination reamer 358 includes combination reamer guide tube 366 having channel 368 formed therein. Swivel/plunge reaming selector 370 is operably connected to a proximal end of combination reamer guide tube 366. As shown in FIGS. 17 and 20, rotation guide pin 388 is fixably secured to combination reamer guide tube 366 and positioned within rotation guide channel 390 of swivel/plunge reaming selector 370. Swivel/plunge reaming selector 370 may be rotated about guide tube 366 of combination reamer 358 between the extremes shown in FIGS. 18 and 19, i.e., with rotation guide pin 388 abutting opposite ends of rotation guide channel 390. When swivel/plunge reaming selector 370 is positioned as shown in FIG. 18, swivel reaming with combination reamer 358 is not allowed because swivel/plunge reaming selector 370 covers channel 368 to prevent swivel movement of reamer shaft 362. To allow for swivel reaming, swivel/plunge reaming selector 370 is rotated into the position shown in FIG. 19, in which channel 392 in swivel/plunge reaming selector 370 aligns with channel 368 in guide tube 366 of combination reamer 358 to allow swivel movement of reamer shaft 362. Reamer shaft 362 is connected to guide tube 366 of combination reamer 358 via pivot 216' and pivot pins 218' to allow for swivel reaming. Combination reamer 358 includes distal flat 386' for signaling complete insertion of combination reamer 358 into the guide tube/retractor.

E. Reaming the Femoral Head Arm and the Femoral Shaft Arm

Figure 21:
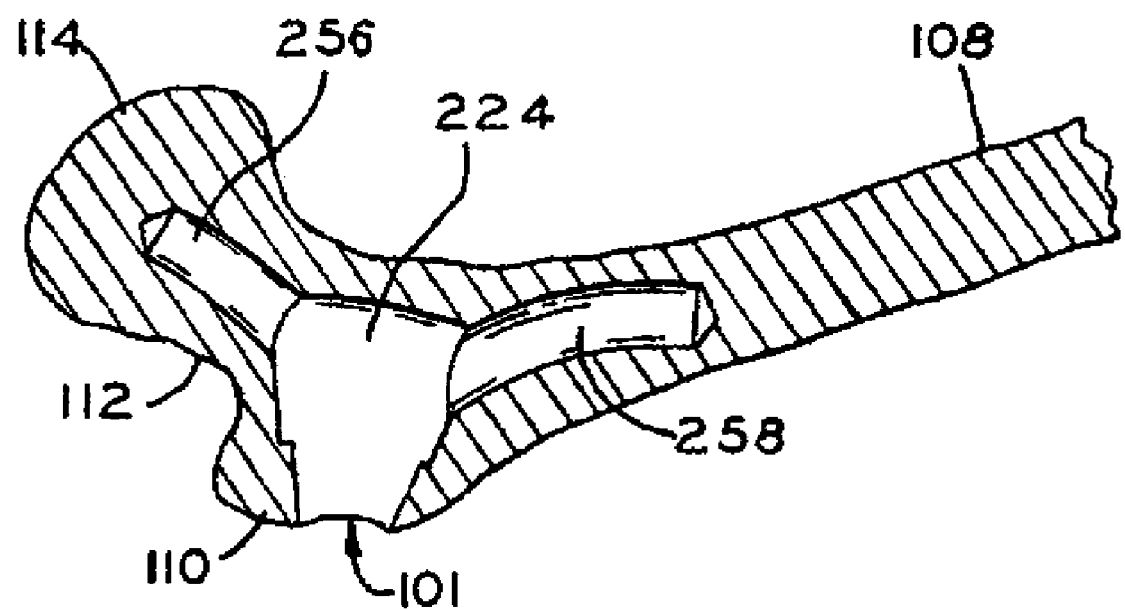
FIG. 21 is a partial sectional view of the femur of the human patient of FIG. 1, further illustrating the implant cavity, the femoral head arm, and the femoral shaft arm.

Referring now to FIG. 21, access 101 and cavity 224 provide access for instrumentation to create femoral head arm 256 and femoral shaft arm 258, as described below.

1. Creation of Femoral Head Arm

Once access 101 and cavity 224 are formed, femoral head arm 256 is created. Telescoping reamer 1044, shown in FIGS. 22 and 23, may be utilized to form femoral head arm 256. The structure and operation of telescoping reamer 1044 are fully described in U.S. patent application Ser. No. 11/061,898, filed Feb. 18, 2005, and U.S. Provisional Patent Application Ser. No. 60/654,481, filed Feb. 18, 2005, the disclosures of which are incorporated herein by reference.

Figure 24:
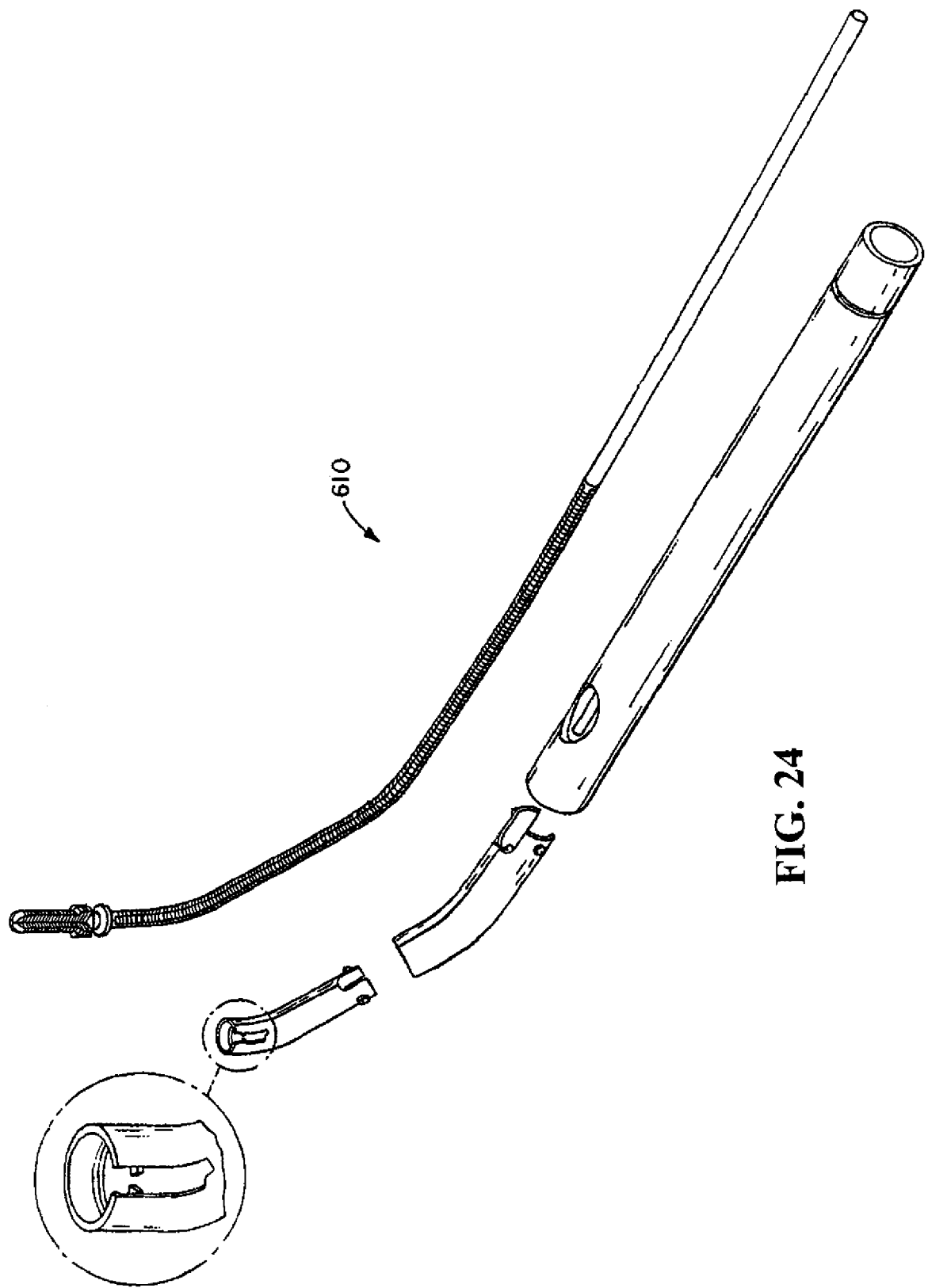
FIG. 24 is an exploded perspective view of a telescoping reamer according to an alternative embodiment.

In an alternative embodiment, telescoping reamer 610, shown in FIG. 24, may be utilized to form femoral head arm 256. The structure and operation of telescoping reamer 610 are fully described in U.S. patent application Ser. No. 10/266,319, filed Oct. 8, 2002, the disclosure of which is incorporated herein by reference.

Figure 25:
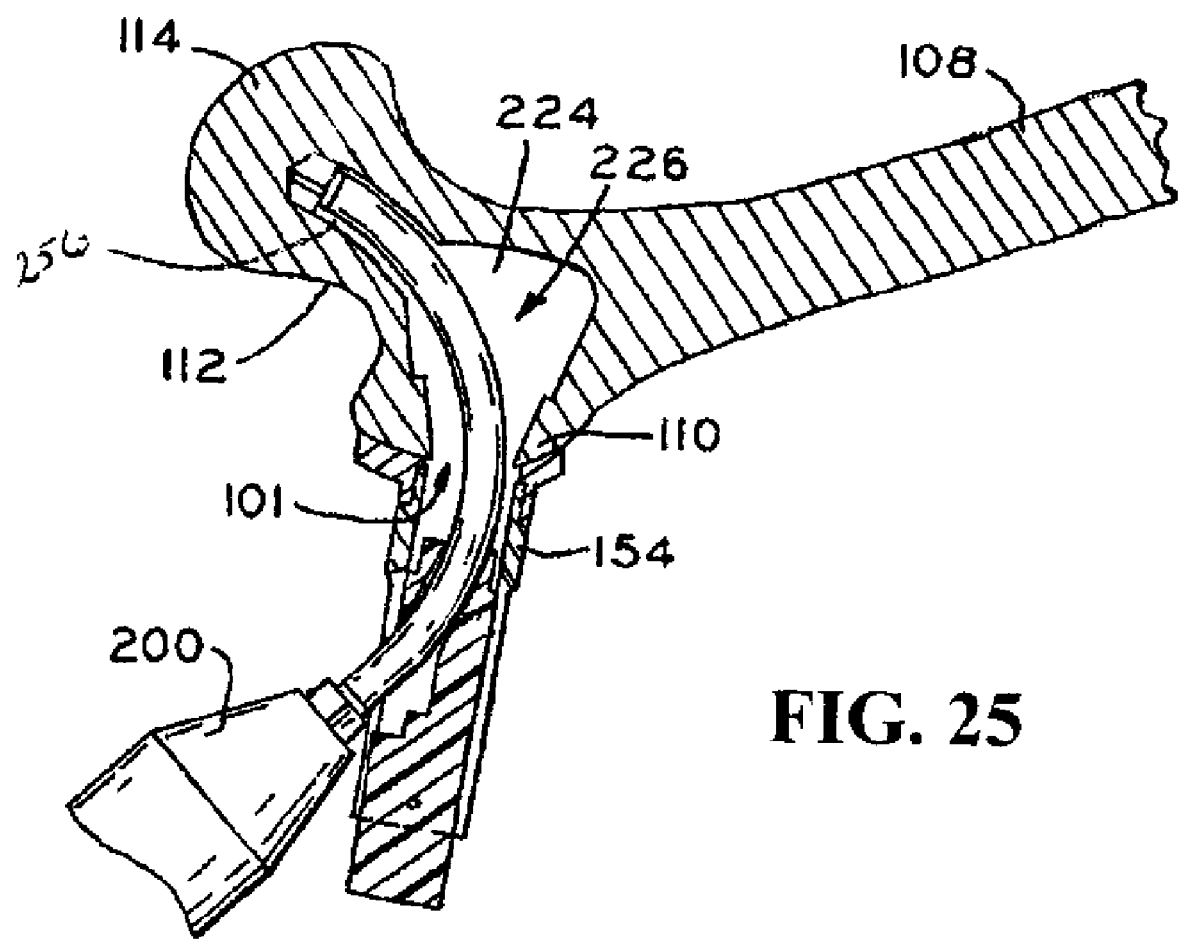
FIG. 25 is a partial sectional view of a curved femoral head arm reamer, further illustrating use of the femoral head arm reamer to create the femoral head arm in the femur of the patient of FIG. 1.

In another alternative embodiment, curved femoral head reamer 226, shown in FIG. 25, may be used to form femoral head arm 256. The structure and operation of curved femoral head reamer 226 are fully described in U.S. patent application Ser. No. 11/061,898, filed Feb. 18, 2005, the disclosure of which is incorporated herein by reference.

2. Creation of Femoral Shaft Arm

Figure 28:
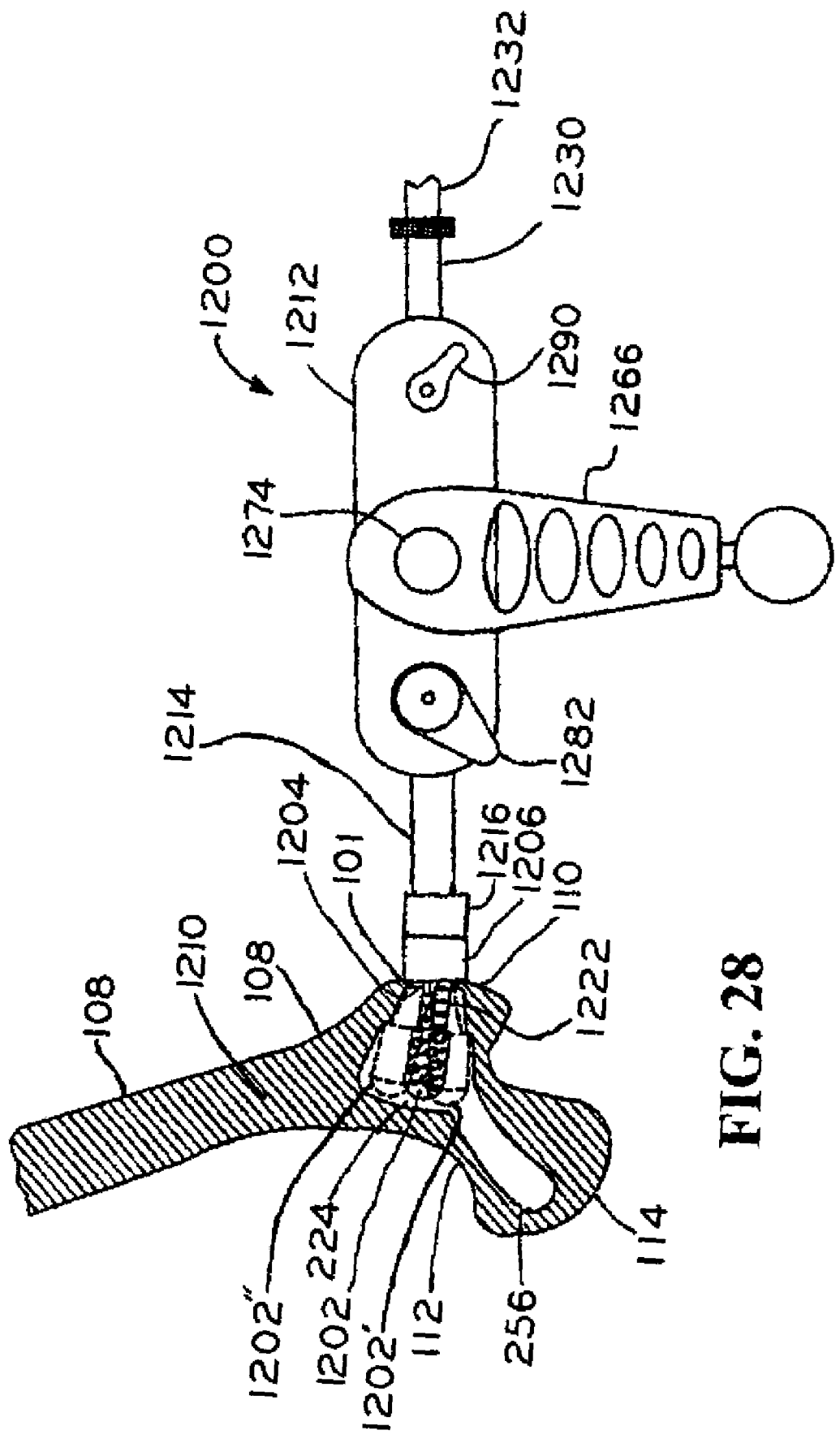
FIG. 28 is a partial sectional view of the flexible reamer of FIG. 26, further illustrating use of the flexible reamer in the femur of the patient of FIG. 1 and moving from a flex-up position to a flex-down position.

Either prior or subsequent to the formation of femoral head arm 256, flexible reamer 1200, shown in FIGS. 26-29, may be used to form femoral shaft arm 258. In operation, flexible reamer head 1202 is positioned through access 101 formed in femur 108. When inserting flexible reamer head 1202 through access 101, interior extension 1204 of distal body end 1206 is positioned within access 101, with flange 1208 abutting the generally planar surface of greater trochanter 110 to advantageously provide a positive depth indication and a stable fixation in femur 108. As shown in FIG. 28, positioned within access 101, flexible reamer head 1202 of flexible reamer 1200 can be actuated between flex up position 1202' and flex down position 1202", each shown in dashed lines, with concurrent rotational driving of reamer head 1202 to effect swivel reaming in the manner described below. In an alternative embodiment, in either flex position, flexible reamer head 1202 can be advanced, for example, to form femoral head arm 256, or flexible reamer head 1202 can be advanced into intramedullary canal 1210 of femur 108 to form femoral shaft arm 258, shown in FIG. 29.

Advantageously, the generally bullet shape of reamer head 1202 and the flexibility of flexible driveshaft 1218 is such that flexible reamer head 1202 is deflected off of relatively dense cortical bone and generally only reams along relatively less dense cancellous bone, for example, of intramedullary canal 1210. Generally, femoral shaft arm 258 is reamed to remove as much cancellous bone as practical in order to anchor an implant, as described below, within the harder, cortical bone of femur 108.

Referring to FIGS. 26 and 27A-C, flexible reamer 1200 includes main body housing 1212 which is connected to outer tool shaft 1214, coupling 1216, and distal body end 1206. Flexible driveshaft 1218 (FIGS. 27A and 29) extends through the cannulated bodies of flexible guide shaft 1222, distal body end 1206, coupling 1216, and outer tool shaft 1214. Distal body end 1206 includes guide tube slot 1220, which accommodates flexure of flexible guide shaft 1222 through a single plane, which, for example, may be coplanar with coronal femoral plane 1008 (FIG. 2). Body cover 1292 (FIG. 27A) may be secured to main body housing 1212 by thumb screw 1294.

Figure 26:
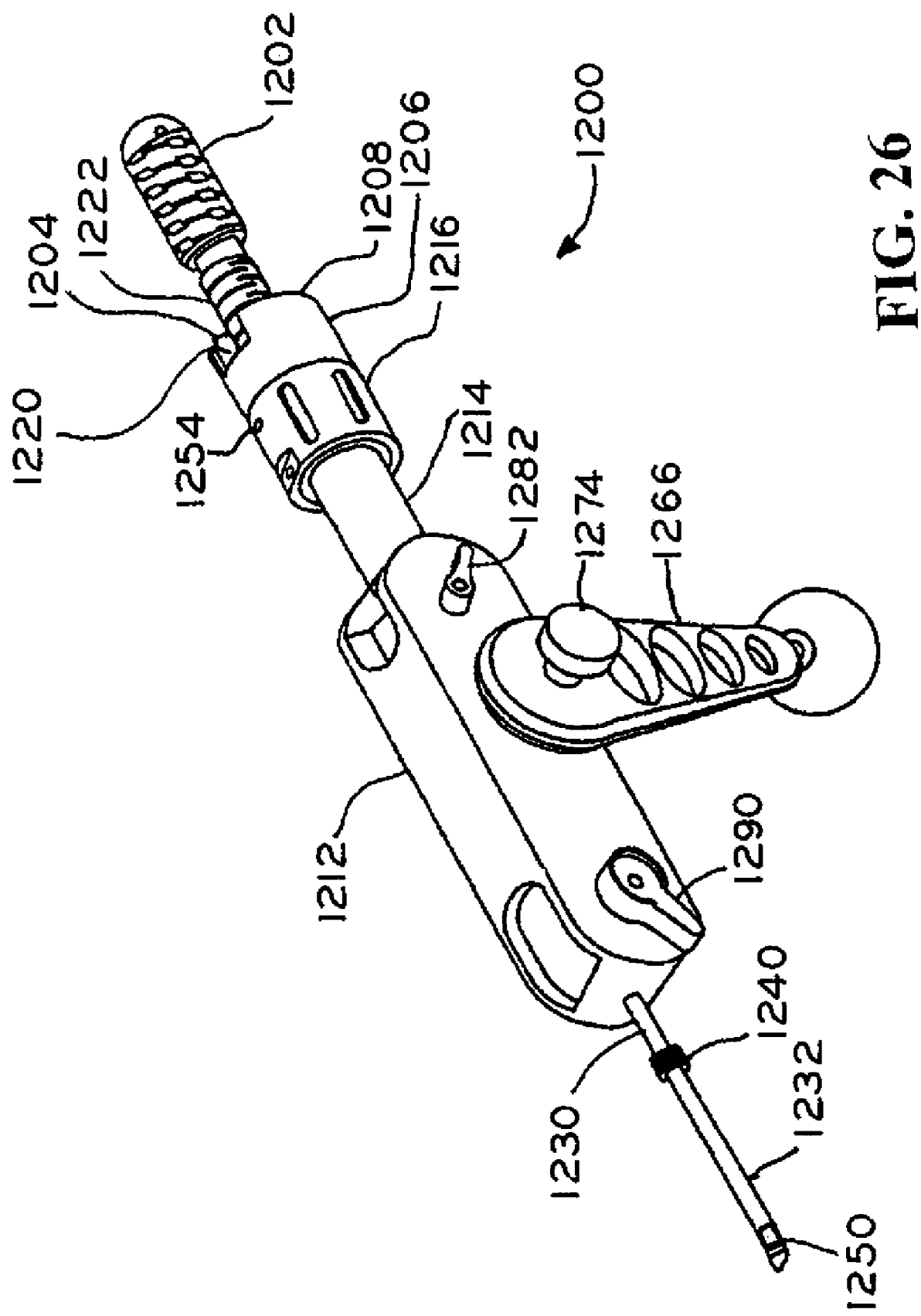
FIG. 26 is a perspective view of a flexible reamer.
Figure 27:
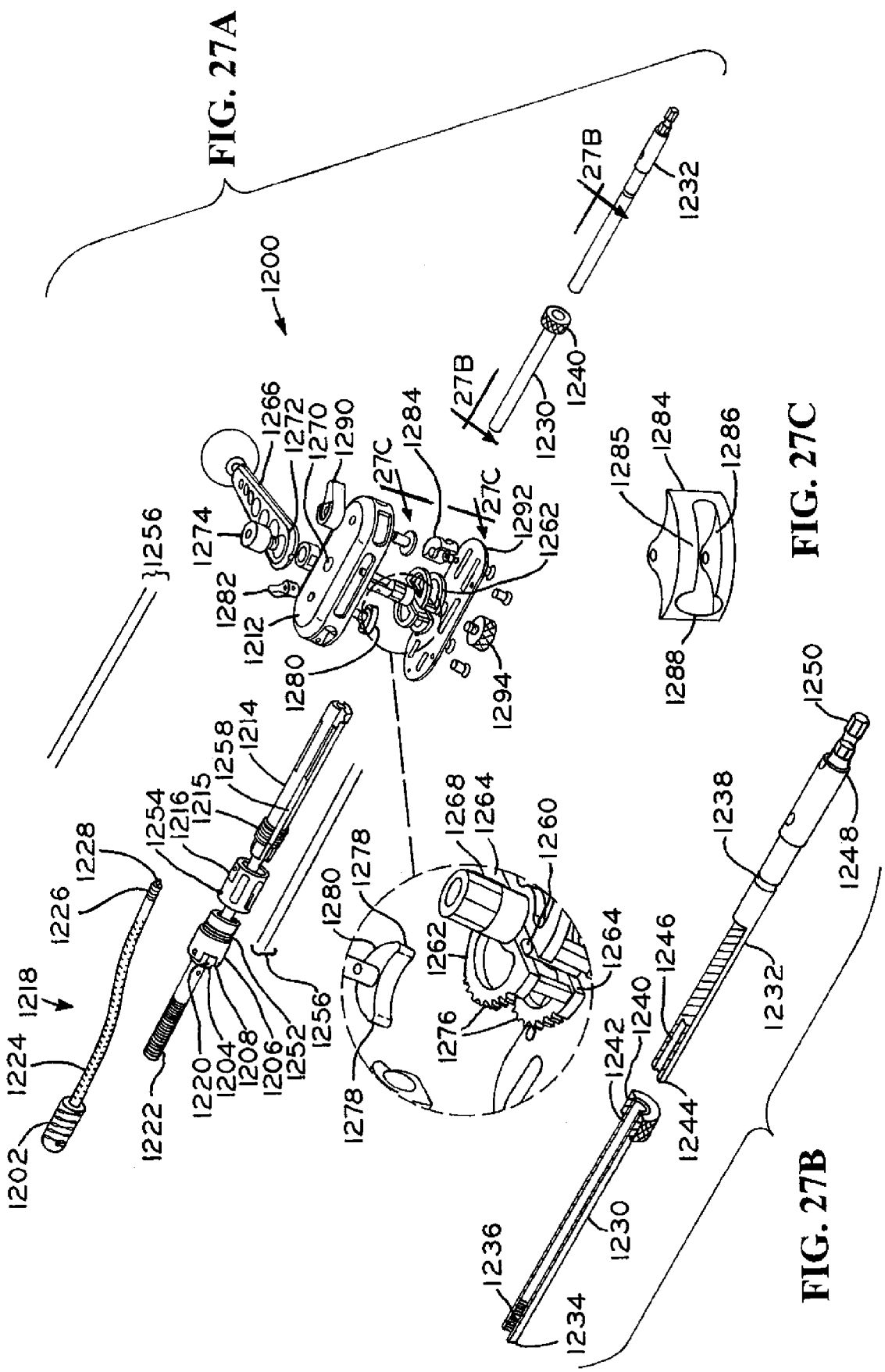
FIG. 27A is an exploded perspective view of the flexible reamer of FIG. 26.
FIG. 27B is a cross-sectional view of the flexible reamer of FIG. 27A, taken along line 27B-27B of FIG. 27A.
FIG. 27C is a perspective view of a portion of the flexible reamer of FIG. 27A.

As illustrated in FIGS. 26 and 27A, flexible driveshaft 1218 includes flexible distal end 1224 and a proximal end having left-hand male thread 1226 and key 1228 protruding proximally from thread 1226. Thread 1226 and key 1228 releasably secure flexible driveshaft 1218 to intermediate driveshaft 1230 and proximal driveshaft 1232. Intermediate shaft 1230 (FIG. 27B) is cannulated for reception of a distal portion of proximal driveshaft 1232 therein. Specifically, distal end 1244 of proximal driveshaft 1232 is received within intermediate driveshaft 1230. Upon drive shafts 1230 and 1232 being fully coupled, distal end 1244 of proximal driveshaft 1232 approximately abuts female threads 1236 located at the interior of distal end 1234 of intermediate driveshaft 1230. Proximate end 1242 of intermediate driveshaft 1230 includes coupling device 1240. Upon drive shafts 1230 and 1232 being fully coupled, circumferential groove 1238 of proximal driveshaft 1232 is located within coupling device 1240. Coupling device 1240 includes interior radial projections (not shown), e.g., pins or spring loaded bearings, for engaging circumferential groove 1238 of proximal driveshaft 1232, thereby longitudinally fixing intermediate driveshaft 1230 to proximal driveshaft 1232 while allowing relative rotation.

Distal end 1234 of intermediate driveshaft 1230 includes female thread 1236 for receiving male thread 1226 of flexible driveshaft 1218. Distal end 1244 of proximal driveshaft 1232 includes keyway 1246, which upon coupling drive shafts 1230 and 1232, is adjacent threads 1236. Flexible driveshaft 1218 is coupled to drive shafts 1230 and 1232. Engagement of key 1228 of flexible driveshaft 1218 in keyway 1246 provides rotational fixation of flexible driveshaft 1218 with proximal driveshaft 1232, thereby enabling driveshaft 1232 to rotationally drive flexible reamer head 1202. Proximal end 1248 of proximal driveshaft 1232 may include flats 1250 for coupling to the chuck of a device capable of imparting rotational motion thereto.

Flexible driveshaft 1218 is longitudinally fixed with proximal driveshaft 1232 by engaging male thread 1226 of flexible driveshaft 1218 with female thread 1236 of intermediate driveshaft 1230. Because male thread 1226 abuts key 1228 and female thread 1236 abuts keyway 1246, engagement of threads 1226 and 1236 secures key 1228 in keyway 1246. Threads 1226 and 1236 are advantageously left handed so that right hand driving of proximal driveshaft 1232, as viewed from the proximal end of flexible reamer 1200, rotates flexible driveshaft 1218 via keyway 1246 and key 1228 without loosening the engagement of threads 1226 and 1236.

Releasably coupling drive shafts 1218, 1230, and 1232 in this manner allows removal of housing 1212, flexible guide shaft 1222, distal body end 1206, coupling 1216, and outer tool shaft 1214 from flexible driveshaft 1218 without removing flexible reamer head 1202 from cavity 224. While proximal driveshaft 1232 is held to prevent flexible shaft 1218 from rotating, coupling device 1240 and intermediate driveshaft 1230 can be rotated relative to drive shafts 1218 and 1232. Left hand rotation of intermediate driveshaft 1230 disengages flexible drive shafts 1230 and 1232 from flexible driveshaft 1218. Without disengagement of drive shafts 1230 and 1232 from flexible driveshaft 1218, the increased diameter of coupling 1240 prevents housing 1212 and other components from sliding proximally off of drive shafts 1230 and 1232. Disengagement of driveshaft 1230 and 1232 allows housing 1212, flexible guide shaft 1222, distal body end 1206, coupling 1216, and outer tool shaft 1214 to slide proximally off of flexible driveshaft 1218.

Referring to FIGS. 27A-C, flexible driveshaft 1218 includes a distal end adapted for connection to flexible reamer head 1202, for example by using a set screw or other fastener. Flexible portion 1224 of flexible driveshaft 1218 may include at least one spiral flex cut, as described below. Flex cuts provide gaps in radially opposing sides of flexible driveshaft 1218 which allow for compression of a side of flexible driveshaft 1218 so that flexure in only a single plane is possible. Similarly, flexible reamer head 1202 may include one or more spiral cuts allowing for flexure thereof.

Figure 39:
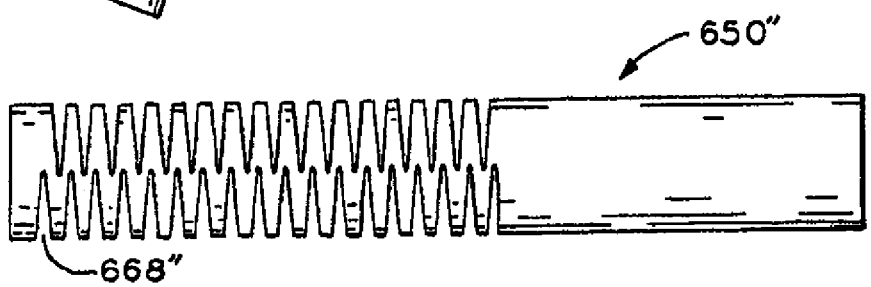
FIG. 39 is a plan view of the flexible guide shaft of FIG. 38 in a straight, non-flexed position.
Figure 40:
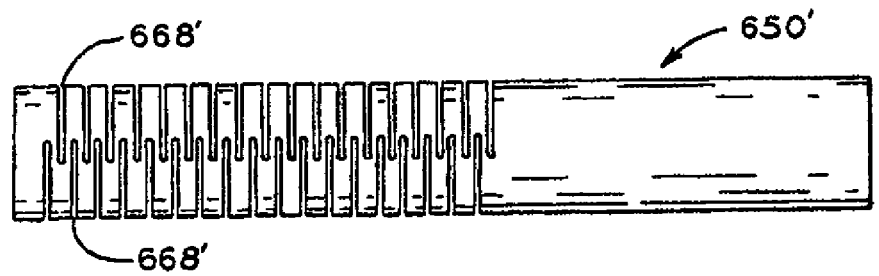
FIG. 40 is a plan view of a flexible guide shaft according to an alternative embodiment.

Flexible portion 1224 of flexible driveshaft 1218 and flexible reamer head 1202 may include a plurality of alternating, substantially semi-circular cuts 668', shown in FIG. 40, or cuts 668", shown in FIGS. 38-39, both of which are described below.

Figure 29:
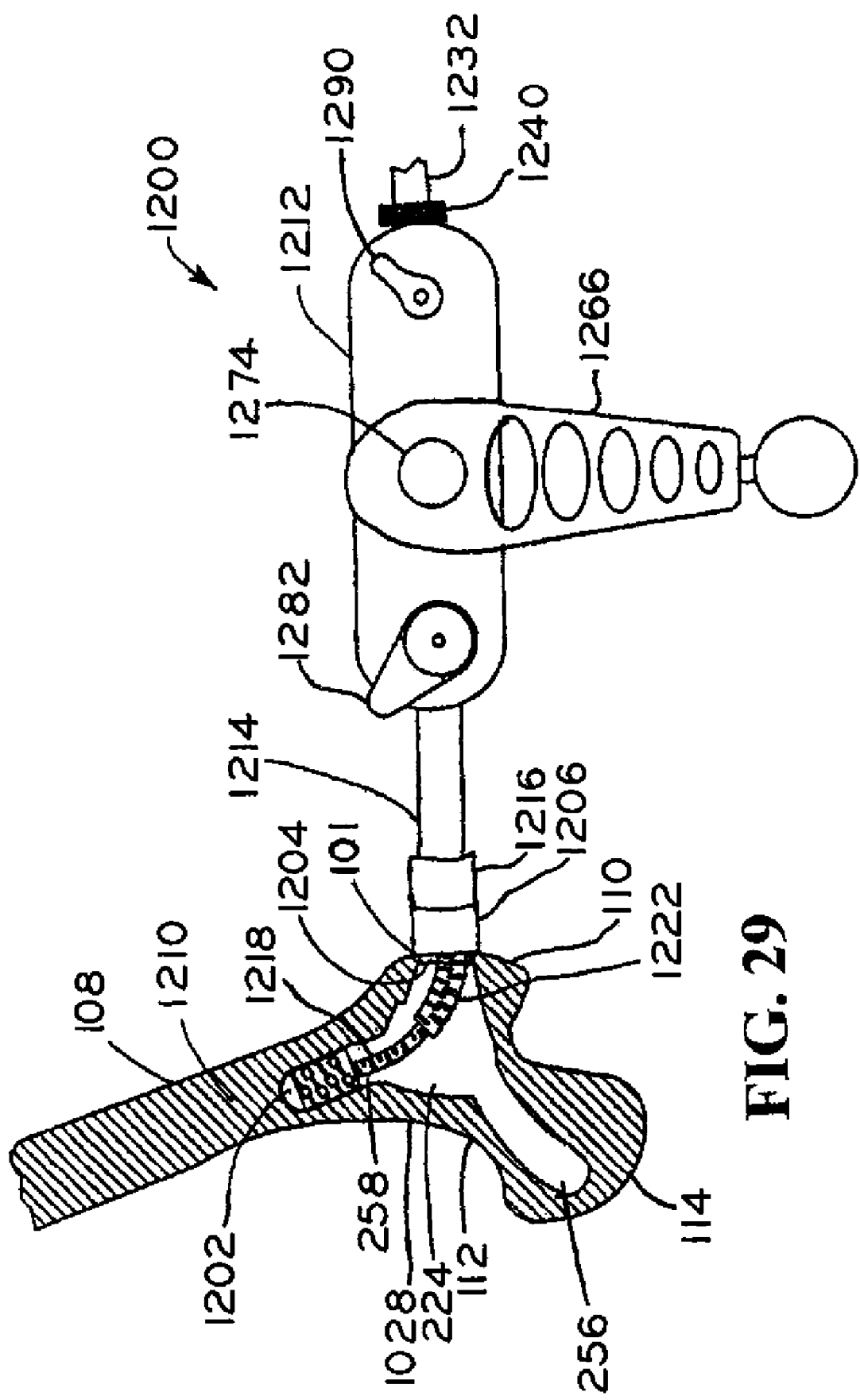
FIG. 29 is a partial sectional view of the flexible reamer of FIG. 26, further illustrating use of the flexible reamer to form the femoral shaft arm.

In operation, flexible driveshaft 1218 can be advanced through flexible guide shaft 1222, thereby providing reaming of femoral shaft arm 258 in femur 108, shown in FIG. 29. Flexible guide shaft 1222 may include at least one spiral cut or, alternatively, may include a plurality of alternating, substantially semi-circular cuts 668' (FIG. 40) or cuts 668" (FIGS. 38-39). In one exemplary embodiment, proximal intermediate driveshaft 1230 includes a coupling device 1240 limiting the length of advancement of flexible reamer head 1202 with respect to the body of flexible reamer 1200, shown in FIG. 29. Specifically, distal advancement of flexible reamer head 1202 requires distal advancement of intermediate driveshaft 1230 and proximal driveshaft 1232, which are coupled to flexible reamer head 1202 by flexible driveshaft 1218. However, distal advancement of flexible reamer head 1202 is stopped by coupling device 1240 contacting the proximal end of main body housing 1212. Although the shaft of intermediate driveshaft 1230 is sized to translate through main body housing 1212 and bore 1288 (FIG. 27C), coupling device 1240 has a larger outer diameter and will not translate there through. In one exemplary embodiment, a plurality of distal body ends 1206 are provided, each distal body end 1206 having a different length, thereby selectively limiting the distal extension length of flexible reamer head 1202 relative to flange 1208. Alternatively, a plurality of couplings 1216 may be provided for the same purpose, each coupling 1216 having a different length.

In construction, flexible guide shaft 1222 is positioned within the distal end of distal body end 1206 and is secured thereto, e.g., with a set screw. Distal body end 1206 is coupled to coupling 1216, e.g., by engaging set screws 1254 (FIG. 27A) radially into circumferential groove 1252 of distal body end 1206, so that coupling 1216 may rotate relative to distal body end 1206 and outer tool shaft 1214. Rotation of coupling 1216 engages or disengages coupling 1216 with threads 1215 of outer tool shaft 1214, thereby allowing assembly and disassembly. Flexible guide shaft 1222 includes a pair of cable apertures (not shown) formed in each of radially opposing sides thereof, separated by 180° and accommodating cables 1256. Cables 1256 are operably positioned through flexible guide shaft 1222 and extend through cable channels 1258 of outer tool shaft 1214. Each pair of cables 1256 extend proximally from outer tool shaft 1214 into main body housing 1212 and are fixably secured to one of pins 1260 (detail of FIG. 27A). Pins 1260 are each coupled in radially outwardly extending slots 1264 of drive wheel 1262. Slots 1264 are located 180° apart.

Drive wheel 1262 is rotationally connected to main body housing 1212 whereby rotation of drive wheel 1262 tensions one pair of cables 1256, thus actuating flexible guide shaft 1222 in guide tube slot 1220. Handle 1266 is operably coupled to drive wheel 1262, and is thereby capable of rotationally actuating drive wheel 1262. Hexagonal shaped hub 1268 (detail of FIG. 27A) of drive wheel 1262 protrudes through aperture 1270 in main body housing 1212 and is received by complementary shaped receptacle 1272 defined in handle 1270. Thumb screw 1274 may be used to fasten handle 1266 to drive wheel 1262. Actuating handle 1266 rotationally clockwise or counter-clockwise thus actuates flexible reamer head 1202 to down position 1202" (FIG. 28) or up position 1202' (FIG. 28), respectively.

Drive wheel 1262 includes teeth 1276 (detail of FIG. 27A) which cooperate with projections 1278, located at opposite ends of locking pawl 1280, to rotationally lock drive wheel 1262. Locking pawl 1280 is pivotably coupled to housing 1212 and is actuated by rotational locking lever 1282 in order to engage one of projections 1278 with teeth 1276 so that drive wheel 1262 is free to rotate clockwise or counter-clockwise, depending upon which projection 1278 is engaged with teeth 1276. Projections 1278 and teeth 1276 are angled upon engagement to function like a ratchet device, allowing engaged projection 1278 to drag over teeth 1276 in a first direction, but to block relative rotation of wheel 1262 in the opposite direction. In one position of rotational locking lever 1282, neither projection 1278 is engaged with teeth 1276 so that drive wheel 1262 is free to be rotated by handle 1266 in either direction. Rotational locking lever 1282 may include a spring detent or other mechanism (not shown) for preventing unintended actuation.

As shown in FIGS. 28-29, reamer handle 1266 is locked by moving handle 1266 to its most distal pointing position and fully turning locking lever 1282 located at the distal end of body housing 1212 of flexible reamer 1200. Locking lever 1282 is shown in unlocked position in FIG. 28 and in locked position in FIG. 29. Once locking lever 1282 is in the locked position, locking lever 1290 located at the lateral end of body housing 1212 may be rotated to the unlock position. Locking lever 1290 is shown in the locked position in FIG. 28 and in the unlocked position in FIG. 29.

Axial lock member 1284 (FIGS. 27A and 27C) is pivotably coupled to main body housing 1212 and operably cooperates with flexible driveshaft 1218 and intermediate driveshaft 1230 to prevent or allow axial translation of flexible reamer head 1202. Specifically, slot 1286 (FIG. 27C), defined in face 1285 of axial locking member 1284, is sized to allow translation of a proximal end of flexible driveshaft 1218 there through and to not allow translation of distal end 1234 (FIG. 27B) of intermediate driveshaft 1230 there through, thus preventing extension of flexible reamer head 1202 from flexible guide tube 1222. However, upon rotation of axial locking member 1284 so that bore 1288 is axially aligned with intermediate driveshaft 1230, intermediate driveshaft 1230 may translate there through, because bore 1288 has an inner diameter greater than that of the outer diameter of intermediate driveshaft 1230. Axial locking lever 1290 is operably coupled to axial locking member 1284 and rotationally actuates member 1284 in order to allow or prevent axial extension there through of intermediate driveshaft 1230, and therefore allow or prevent extension of flexible reamer head 1202 from flexible guide tube 1222. Axial locking lever 1290 may include a spring detent or other mechanism (not shown) to prevent accidental actuation. Thus, locking lever 1290 permits flexible driveshaft 1218 to be advanced through flexible guide shaft 1222, shown in FIG. 29. In this extended position, reamer head 1202 may be rotatably driven to form femoral shaft arm 258.

In an alternative embodiment shown in FIGS. 30-37 and 41-42, flexible reamer 826 may be utilized to form femoral shaft arm 258, and/or femoral head arm 256. Flexible reamer head 828 is positioned through access 101 formed in femur 108. When inserting flexible reamer 826 through access 101, interior extension 838 of distal body end 832 is positioned within access 101, with flange 840 abutting the exterior wall of femur 108. In this position, flexible reamer 826 can be actuated between the flex up position shown in FIG. 31 and the flex down position shown in FIG. 33 with concurrent rotational driving to effect swivel reaming. Furthermore, in the flex up position shown in FIG. 31, flexible reamer head 828 can be advanced into femoral head 114 to form femoral head arm 256. Similarly, in the flex down position shown in FIG. 33, flexible reamer head 828 can be advanced into the intramedullary canal of femur 108 to form femoral shaft arm 258.

Figure 30:
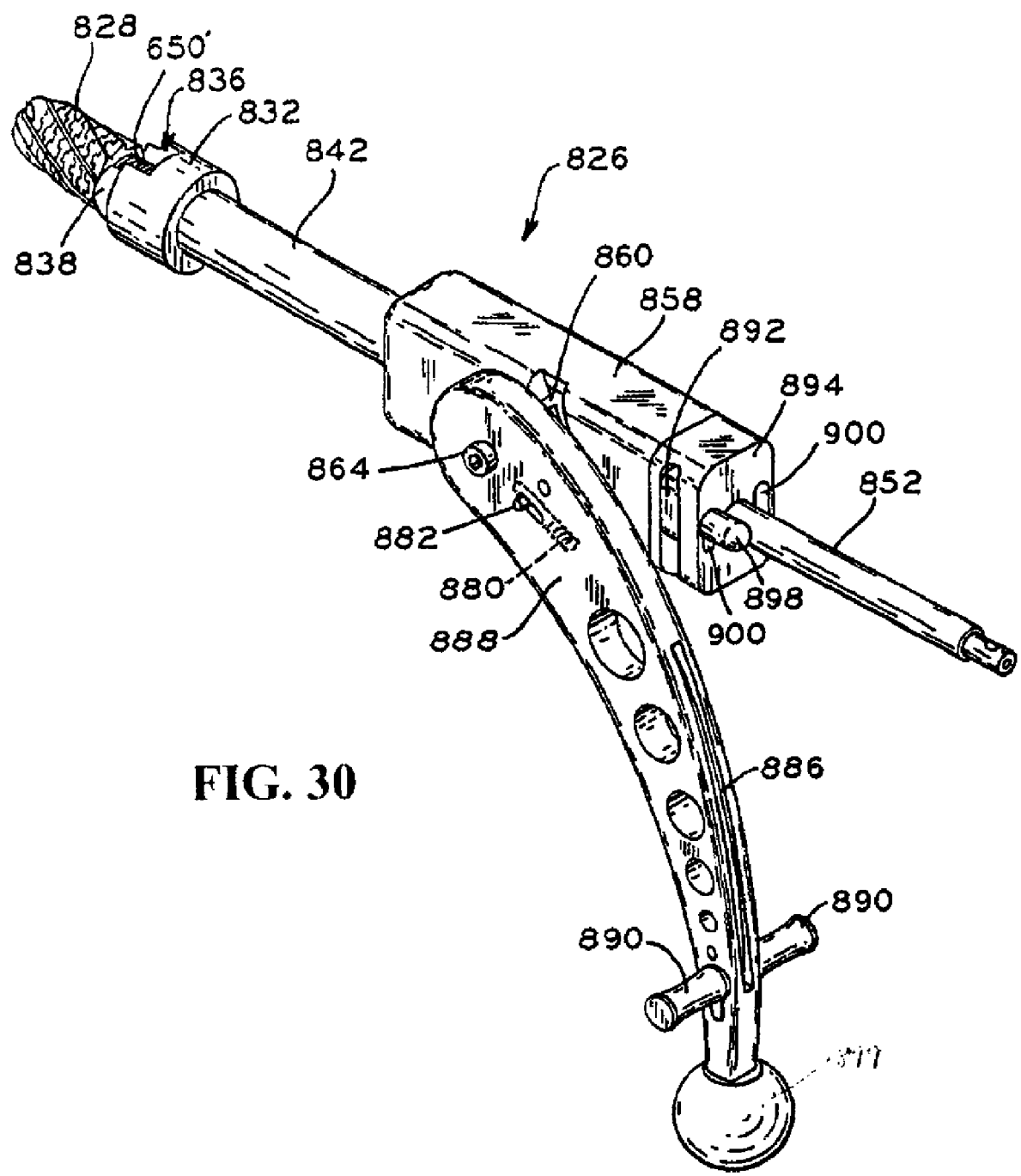
FIG. 30 is a perspective view of a flexible reamer according to an alternative embodiment.
Figure 31:
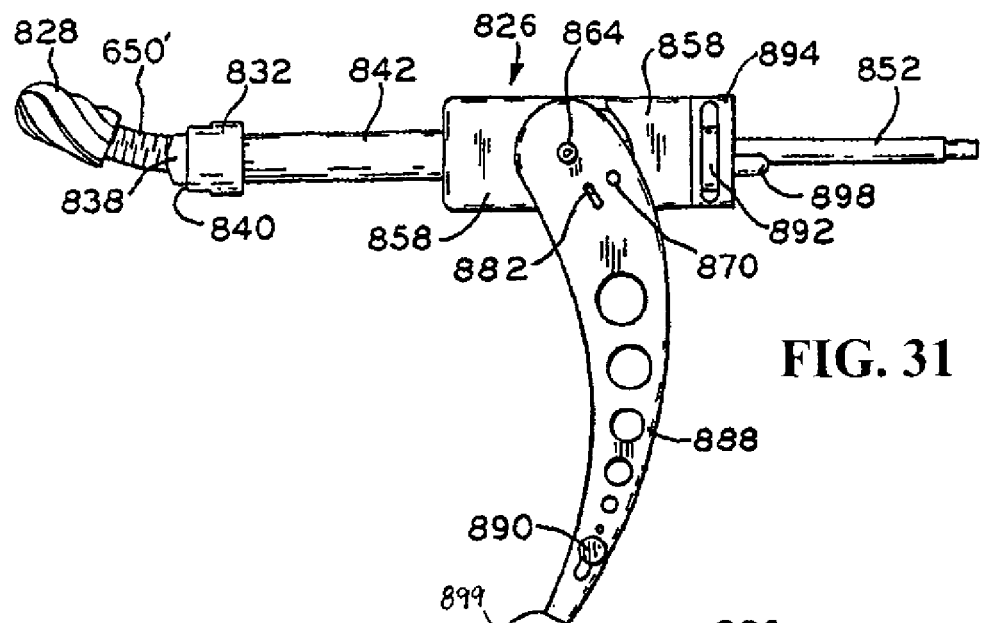
FIG. 31 is a side plan view of the flexible reamer of FIG. 30, further illustrating the reamer head in a flex-up position.
Figure 32:
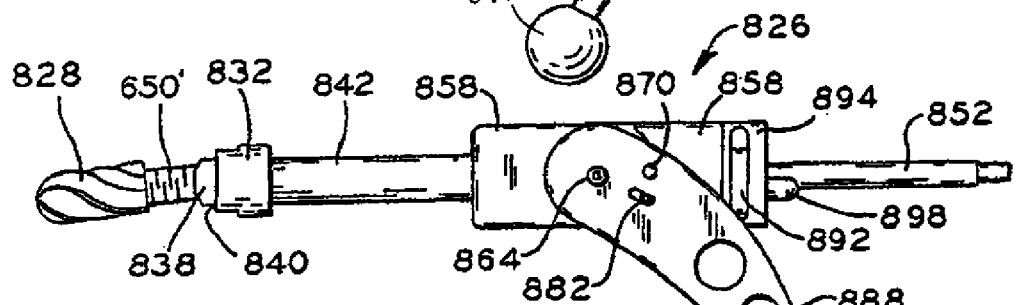
FIG. 32 is a side plan view of the flexible reamer of FIG. 30, further illustrating the reamer head in a slightly flex-down position.
Figure 33:
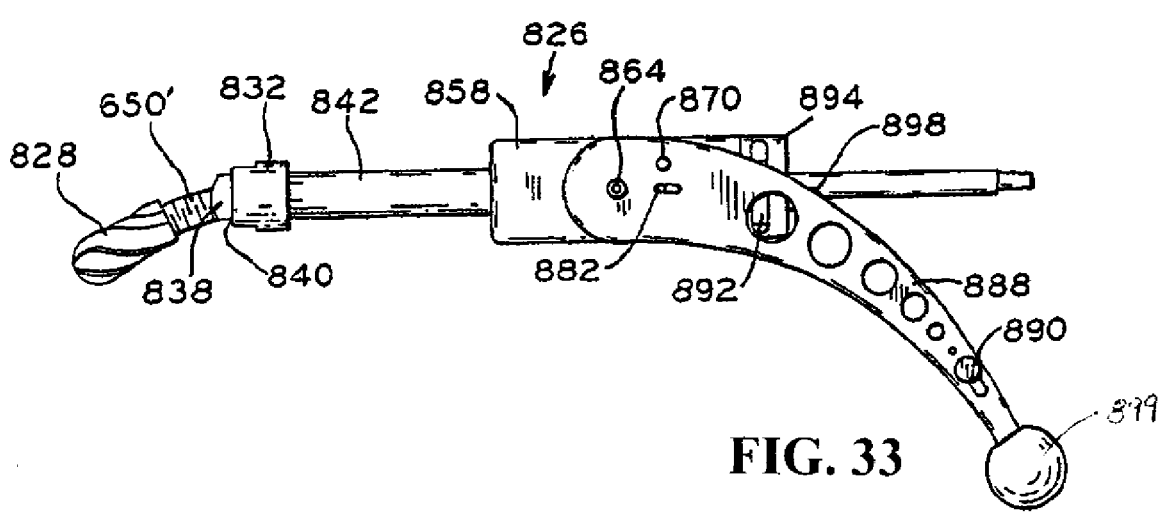
FIG. 33 is a side plan view of the flexible reamer of FIG. 30, further illustrating the reamer head in a flex-down position.
Figure 34:
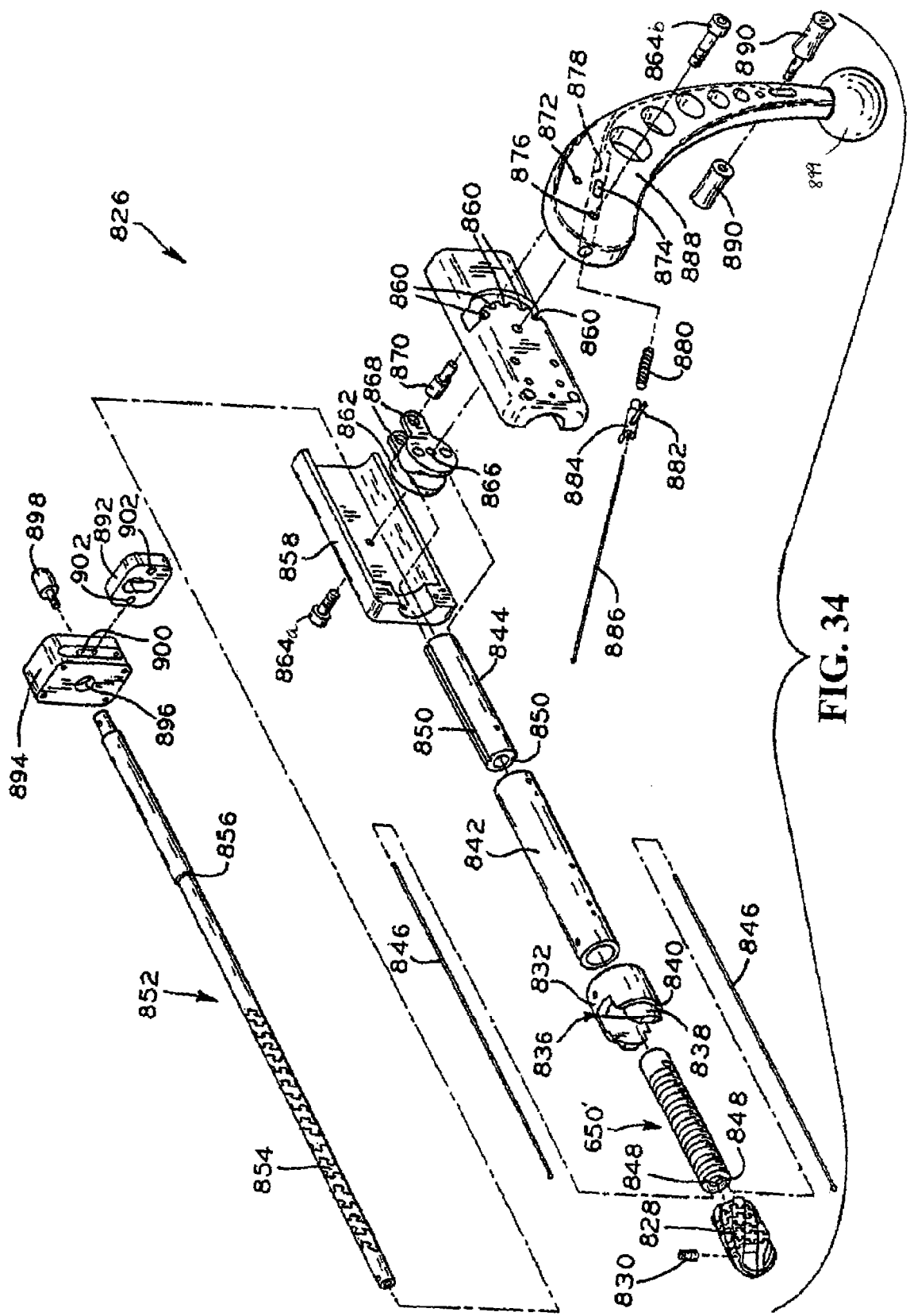
FIG. 34 is an exploded view of the flexible reamer of FIG. 30.

Referring to FIGS. 30-34, flexible reamer 826 includes proximal body end 894 connected to main body housing 858 which is further connected to outer tool shaft 842 and distal body end 832. Flexible driveshaft 852 extends through the cannulated body of flexible reamer 826. Distal body end 832 includes guide tube slot 836 accommodating flexure of flexible guide shaft 650' or 650" (FIGS. 38-39). As shown in FIGS. 31-33, flexible driveshaft 852 includes a proximal end for securing flexible driveshaft 852 to the chuck of a device for imparting rotational motion thereto. Referring to FIG. 34, flexible driveshaft 852 includes a distal end adapted for connection to flexible reamer head 828. As shown in FIG. 34, set screw 830 traverses a generally radial aperture in flexible reamer head 828 and is thereafter engaged in a radial aperture positioned at the distal end of flexible driveshaft 852. As shown in FIG. 34, flexible driveshaft 852 includes flexible distal end 854. Flexible distal end 854 may include at least one spiral flex cut. Similarly, flexible reamer head 828 may include a plurality of spiral cuts allowing for flexure thereof.

Referring still to FIG. 34, with flexible reamer head 828 secured thereto, flexible driveshaft 852 traverses the central apertures of flexible guide shaft 650', inner tool shaft 844, and proximal body end 894 to protrude proximally from flexible reamer 826, shown in FIGS. 31-33. In construction, distal body end 832 is secured about outer tool shaft 842. Flexible guide shaft 650' is positioned within the distal end of outer tool shaft 842 and is secured thereto with, e.g., a set screw. Similarly, inner tool shaft 844 is positioned within outer tool shaft 842 and is secured thereto with, e.g., a set screw. In construction, inner tool shaft 844 is positioned with its distal end in close proximity to the proximal end of flexible guide shaft 650'. In one exemplary embodiment, the distal end of inner tool shaft 844 abuts the proximal end of flexible guide shaft 650'. As shown in FIGS. 34-35 and 41-42, flexible guide shaft 650' may include a pair of cable apertures 848 formed in radially opposing sides thereof. With reference to flexible guide shaft 650', "radially opposing sides," and/or "opposing sides" refers to a pair of outer portions of flexible guide shaft 650' separated by 180°. Flexible guide shaft 650' can take many forms, including those in which the transverse cross section is circular or polygonal. Cable apertures 848 accommodate cables 846, shown in FIG. 34. Cables 846 include a ball, flange, or otherwise radially expanding structure or protrusion on a distal end thereof to prohibit cables 846 from being pulled through cable apertures 848 in a distal to proximal fashion. When operably positioned through cable apertures 848, the radially expanded distal end of cables 846 abuts the distal end of flexible guide shaft 650'. Cables 846 extend from the proximal end of flexible guide shaft 650' and are positioned in cable channels 850 of inner tool shaft 844. Cables 846 further extend proximally from inner tool shaft 844 and are received by and fixably secured to mandrel 862.

Referring now to FIGS. 34 and 37, mandrel 862 is pivotably connected to main body housing 858 whereby rotation of mandrel 862 tensions one of cables 846. Lag screws 864a and 864b are utilized to pivotally connect mandrel 862 to main body housing 858. As shown in FIG. 34, lag screws 864a and 864b are positioned through opposing sides of main body housing 858 to pivotally connect mandrel 862 thereto. One lag screw 864b traverses handle 888 to further pivotally connect handle 888 to main body housing 858. Mandrel 862 is rotationally fixed to handle 888 via pin 870. Pin 870 traverses an aperture formed in at least one pivot arm 868 of mandrel 862 and extends through the arcuate slot formed proximally of detents 860 in main body housing 858 and is engaged in aperture 872 of handle 888. Rotation of handle 888 about lag screw 864b therefore causes rotation of mandrel 862 about lag screw 864a. As handle 888 and mandrel 862 are rotated relative to main body housing 858, one cable 846 is tensioned to force flexible guide shaft 650' into a flexed position as shown, e.g., in FIG. 38. For example, if handle 888 and, consequently, mandrel 862 are rotated clockwise, then the upper cable 846 is tensioned and flexible guide shaft 650' is curved upward to place flexible reamer 826 in the flex up position, shown in FIG. 31. Similarly, if handle 888 is rotated counterclockwise, flexible reamer head 828 is positioned in the flex down position, shown in FIG. 33.

Figure 38:
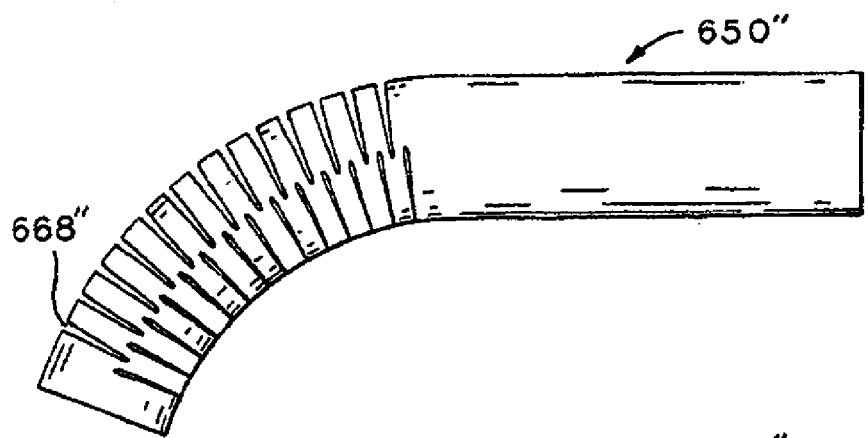
FIG. 38 is a plan view of a flexible guide shaft in a flexed position.

Tensioning of a cable 846 exerts a distal to proximal force on flexible guide shaft 650' causing compression of one side of flexible guide shaft 650' as shown, e.g., in FIG. 38. In an alternative embodiment, a flexible shaft or other device for transmitting force in a non-linear fashion may be utilized to push or extend one side or portion of the distal end of flexible guide shaft 650' in a proximal to distal direction and cause compression of the opposing side thereof. Flex cuts 668" provide gaps in radially opposing sides of flexible guide shaft 650' which gaps allow for compression of a side of flexible guide shaft 650' as shown, e.g., in FIG. 38. Each flex cut 668' (FIG. 39) or 668" (FIG. 40) is a discrete cut, i.e., each flex cut 668' or 668" does not intersect another flex cut 668' or 668". As shown in FIGS. 38-40, flex cuts 668' or 668" may take many forms, including triangular cuts 668", shown in FIGS. 38-39, and straight cuts 668', shown in FIG. 40. Other geometrical shapes may be utilized to form flex cuts 668' or 668". Importantly, material of flexible guide shaft 650' is removed to allow for compression of a portion of flexible guide shaft 650' to allow for flexure thereof as shown in FIG. 38. Further, flex cuts 668' or 668" are formed so that flexure in only a single plane (hereinafter the "plane of flexure") is possible, i.e., the longitudinal axis of guide shaft 650' remains in a single plane whether guide shaft 650' is flexed or straight.

Figure 41:
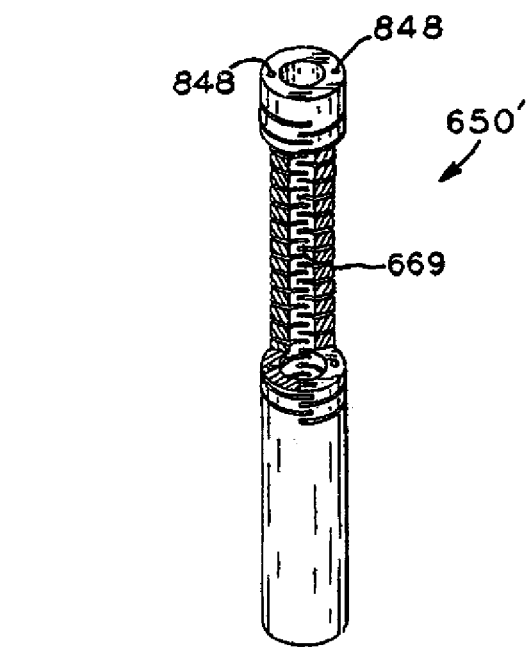
FIG. 41 is a partial perspective view of the flexible guide shaft of FIG. 40.
Figure 42:
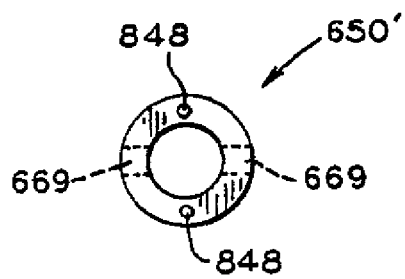
FIG. 42 is an end view of the distal end of the flexible guide shaft of FIG. 40.

To accommodate flexure in only the plane of flexure, flex cuts 668' or 668" are formed to leave continuous material 669 on radially opposing sides of guide shaft 650', shown in FIGS. 41-42. The radially opposing sides having continuous material 669 are 90° from the plane of flexure and prevent flexure in any plane other than the plane of flexure. Continuous material 669 further prevents compression of flexible guide shaft 650' when one of cables 846 is tensioned. Flex cuts 668' or 668" are formed through radially opposing sides of flexible guide shaft 650'. Flex cuts 668' or 668" each extend from the outer surface of flexible guide shaft 650' to and slightly beyond the longitudinal axis of flexible guide shaft 650'. Advantageously, flexure of guide shaft 650' in a single plane provides for excellent control and predictability in controlling the flexure of flexible driveshaft 852 and flexible reamer head 828. In an alternative embodiment (not shown), flex cuts are made through one side only of flexible guide shaft 650', e.g., the flex cuts are only made in the top or bottom of guide shaft 650' as oriented in FIG. 40.

Handle 888 includes a lock mechanism for retaining flexible reamer head 828 in one of the flex up, straight, and flex down positions. As shown in FIG. 34, handle 888 includes internal aperture 878 accommodating detent rod body 884. With detent rod body 884 positioned within internal aperture 878 of handle 888, detent rod 882 extends through detent rod slot 874. Cable 886 extends through the central aperture of detent rod body 884 and through internal aperture 878 of handle 888. As shown in FIG. 30, cable 886 exits internal aperture 878 and is positioned within an external channel formed in handle 888 and is secured to cable finger grips 890 at an end thereof opposite detent rod body 884. As shown in FIG. 34, internal aperture 878 includes a counter bore. Spring 880 is positioned against an external shoulder formed in detent rod body 884 and cooperates with counter bored aperture 878 of handle 888 to bias detent rod 882 into the position shown in FIGS. 31 and 33. In this position, detent rod 882 is positioned within one of detents 860 (FIGS. 34 and 37) formed in main body housing 858.

Referring to FIGS. 31-33, to rotate handle 888 to actuate flexible reamer head 828 between the flex up, straight, and flex down positions, cable finger grips 890 are moved from the position shown in FIG. 31 to the position shown in FIG. 32 towards knob 899 against the biasing force of spring 880. This movement of cable finger grips 890 repositions detent rod 882 from the position shown in FIG. 31 to the position shown in FIG. 32 and moves detent rod 882 from position within one of detents 860 into the arcuate channel adjacent to and proximal of detents 860. In this position, handle 888 can be moved to actuate flexible reamer head 828 between, e.g., a selected flex-up, straight, and a selected flex-down position. Due to the plurality of detents 860, multiple flex-up and flex-down positions are possible. When the chosen position is achieved, cable finger grips 890 can be released so that the biasing force of spring 880 acts against detent rod body 884 to position detent rod 882 in one of detents 860 and lock handle 888 in position.

Flexible reamer 826 also includes a lock-out feature which prevents axial movement of flexible driveshaft 852 with respect to the remainder of flexible reamer 826. As shown in FIG. 34, flexible driveshaft 852 includes shoulder 856. In the retracted position shown in FIG. 30, shoulder 856 is positioned within proximal body end 894. As shown in FIGS. 30-33, lock plate 892 is positioned within proximal body end 894 of flexible reamer 826. Lock plate 892 is shown in detail in FIG. 36 and includes a central aperture formed by the intersection of release aperture 906 with lock aperture 904. Both lock aperture 904 and release aperture 906 accommodate rotational movement of flexible driveshaft 852. However, only release aperture 906 accommodates passage of shoulder 856 of flexible driveshaft 852. Lock aperture 904 is sized whereby shoulder 856 will not pass there through. As shown in FIGS. 30-34, lock knob 898 is positioned through lock knob slot 900 of proximal body end 894 and engaged with lock plate 892 via lock knob aperture 902. Lock knob 898 can be moved within lock knob slot 900 of proximal body end 894 to actuate lock plate 892 to allow for distal to proximal advancement of flexible driveshaft 852 by positioning flexible driveshaft 852 within release aperture 906. Lock knob 898 can also be utilized to reposition lock plate 892 so that flexible driveshaft 852 is positioned within lock aperture 904. Achieving the locked position of lock plate 892 is only possible when flexible driveshaft 852 is positioned in the retracted position shown in FIG. 30. FIG. 30 illustrates lock knob 892 positioned whereby flexible driveshaft 852 is positioned within lock aperture 904, while FIGS. 31-33 illustrate lock knob 898 positioned whereby flexible driveshaft 852 is positioned within release aperture 906 of lock plate 892 and flexible driveshaft 852 is moved in a proximal to distal direction to advance flexible reamer head 828. In one exemplary embodiment, flexible driveshaft 852 includes a proximal flange limiting the length of advancement of flexible reamer head 828 with respect to the body of flexible reamer 826.

In an alternative embodiment, a curved femoral shaft reamer (not shown) having a substantially identical structure to curved femoral head reamer 226 (FIG. 25) may be used to form femoral shaft arm 258.

F. Implant Bag Construction

Figures 45, 46A, 46B:
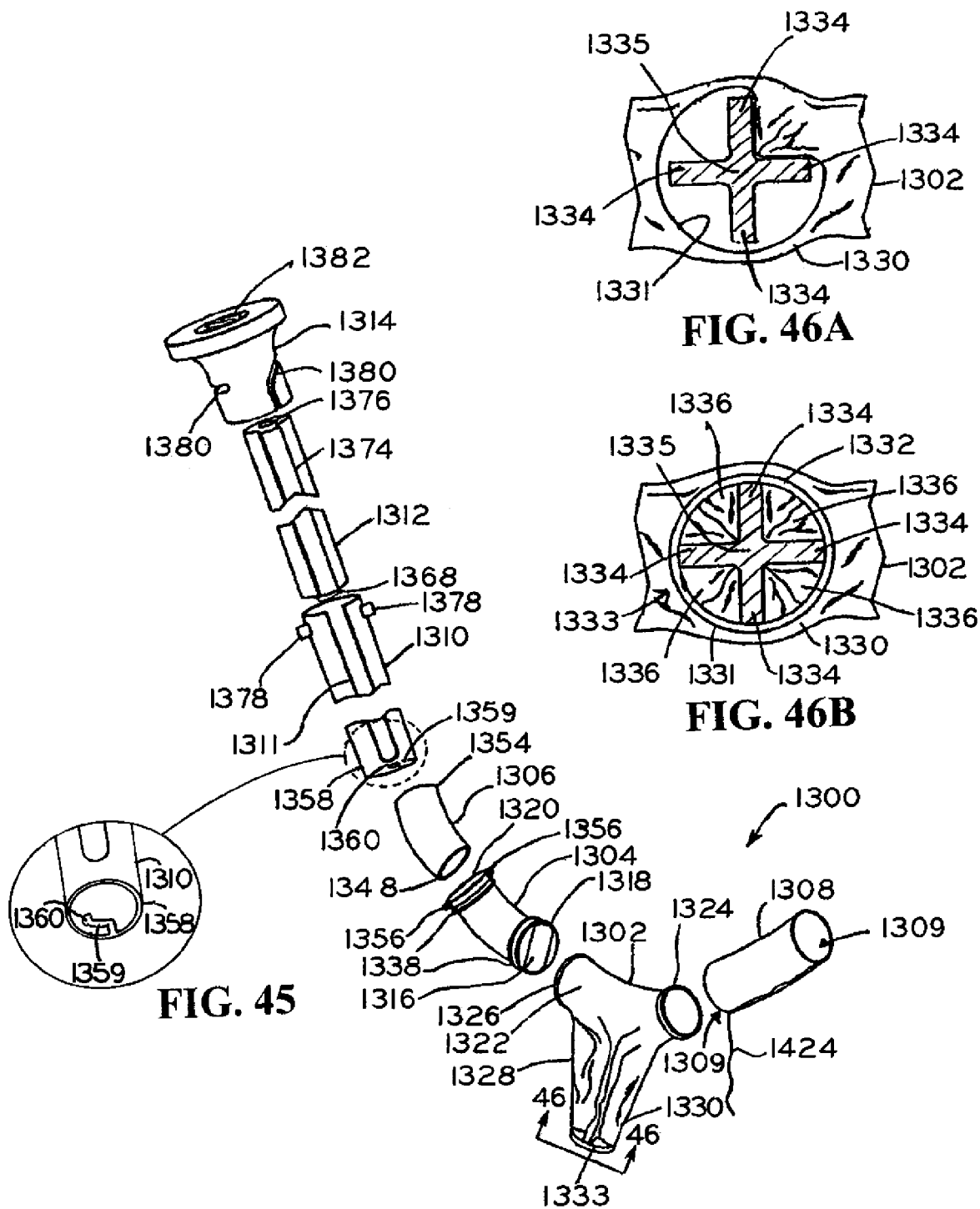
FIG. 45 is an exploded view of an implant according to one embodiment.
FIGS. 46A and 46B are sectional views of the implant of FIG. 45, taken along line 46-46 of FIG. 45.

Referring now to FIGS. 45 and 47, implant 1300, 2000 includes implant bag 1302, 2002 generally comprising a containment device which may be constructed of various materials including films such as, e.g., fiber or fabric reinforced films, or fabrics created by processes such as weaving, knitting, braiding, electrospinning, hydrospinning, or any combination thereof. In one exemplary embodiment, implant bag 1302, 2002 is formed from a biocompatible acrylic material, e.g., a woven acrylic material. Because bone cement is an acrylic, if implant bag 1302, 2002 is formed of an acrylic material, implant bag 1302, 2002 and the bone cement therein will achieve an intimate chemical bond. Alternative materials contemplated for implant bag 1302, 2002 include various polymers including, e.g., polymethylmethacrylate (PMMA), polycarbonate, ultra-high molecular weight polyethylene (UHMWPE), low density polyethylene (LDPE), high density polyethylene (HDPE), polyamides, polypropylene, polyester, polyaryletherketone, polysulfone, polyurethane, or hydrogels. Further alternative materials contemplated for implant bag 1302, 2002 include fabrics constructed of fibers formed of glass, ceramics, surgical grade stainless steel (e.g., 316L), titanium, titanium alloys, tantalum, or shape memory materials. Moreover, implant bag 1302, 2002 materials may be coated with, e.g., calcium phosphate, or a bioactive glass coating. Furthermore, implant bag 1302, 2002 and the associated filler may be utilized as a delivery mechanism for, e.g., drugs, or growth factors.

In one embodiment, implant bag 1302, 2002 may be flexible and woven of PMMA with a sufficiently tight weave to contain a biologically compatible filler. The filler may be, for example, a curable material, an expandable material, a fibrous or woven material, nitinol, hydrogel, or a known bone cement, e.g., PMMA based bone cement. Bone cement is generally inserted as a liquid, conforming to the shape of cavity 224 and femoral shaft arm 258 and then cures to a solid. Implant bag 1302, 2002 may alternatively be a biocompatible material which is expandable after implantation into femur 108, for example, an expandable biocompatible fabric or textile, nitinol, or hydrogel. Nitinol has the advantage of being able to compress from a "set" shape to a small shape and temporarily hold that shape; however, upon heating, nitinol will resume to the set shape, thus allowing a dimensionally small implant insertion size which expands upon receiving body or other heat. Hydrogel has the advantage of expanding dramatically in volume when exposed to water; therefore, implant bag 1302, 2002 could be expanded using water or an aqueous solution after placement within cavity 224 and femoral shaft arm 258.

Implant bag 1302, 2002 may be woven polyester, knit polyester, or spunbound polyester. The woven polyester bags may be fabricated from Texwipe TX1010 (100% continuous filament polyester) sheets manufactured by ITW Texwipe of Mahwah, N.J. The spunbound bags may be fabricated from Absorbond TX409 (100% hydroentangled polyester) spunbond sheets also manufactured by ITW Texwipe of Mahwah, N.J. The porosity and pore size of the fabric can be created to optimize the amount of cement permeation for example. The more porous material may allow more cement to permeate implant bag 1302, 2002 and the increased interdigitation of cement into the cancellous bone may thereby increase stability of the implant. The stronger material may have a greater resistance to rupture of implant bag 1302, 2002.

The fibers used to form implant bag 1302, 2002 may be formed through a process known as melt-spinning, the discussion of which is contained in *Joseph's Introductory Textile Science* by P. B. Hudson et al. (Sixth edition, pages 68-75), the text of which is hereby expressly incorporated herein by reference. The melt-spinning process begins by placing polymer chips or pellets into a hopper/dryer. The dryer may be included to eliminate moisture in the polymer chips or pellets. From the hopper, the pellets are transferred to a melt tank wherein the pellets are melted. A pump is operable to move the melted polymer to a filter pack comprised of essentially a metal sheet with holes (metal mesh material) which controls the polymer flow rate. Spinnerettes are used to extrude the melted polymer into a cooling tower or chamber, where the polymer hardens or solidifies in a continuous fiber form. Most melt-spun fibers are quenched in air, but some are water-quenched prior to drawing. The individual fibers are converged and pass over a finish roll which applies an anti-static, lubricating finish to the fibers. After finishing, the fibers are traversed over a number of rollers or godets, in one embodiment, four godets, wherein the fiber wraps around each godet approximately seven times. A bailer roll located beyond the godets moves fiber up and down on a wind-up spool for collection.

In an alternative embodiment, implant bag 1302, 2002 may be constructed to allow for bone in growth into the bag to thereby further stabilize the implant bag in a bone structure.

In a further embodiment, implant bag 1302, 2002 comprises a nested bag structure in which an inner bag is filled with a high strength material relative to the material of an outer bag in which the inner bag is placed. The outer bag is formed from and filled with a more bioresorbable material relative to the material of construction and fill material of the inner bag.

Figure 44A:
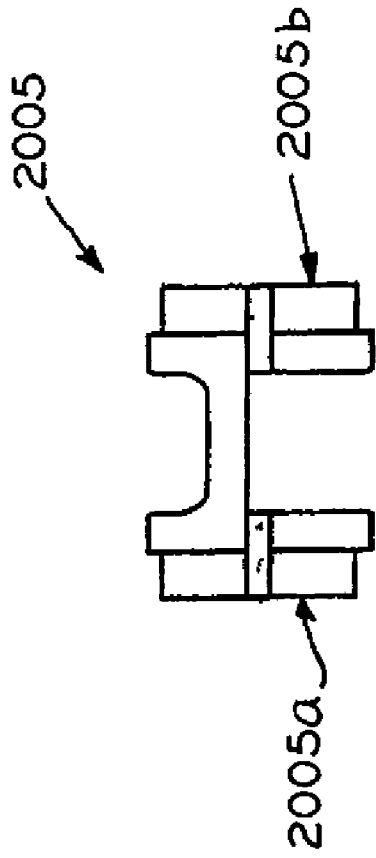
FIG. 44A is a side view of a mandrel used to form the implant bag of FIG. 47.
Figure 44C:
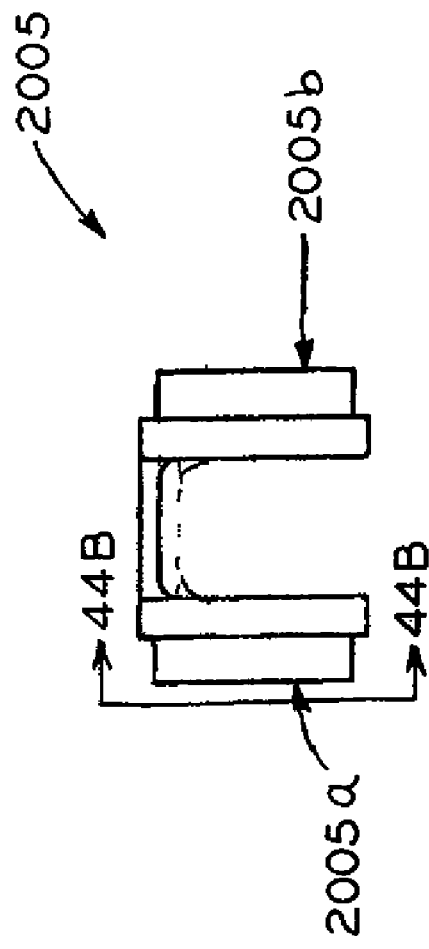
FIG. 44C is a side view of the mandrel of FIG. 44A slightly rotated.
Figure 44B:
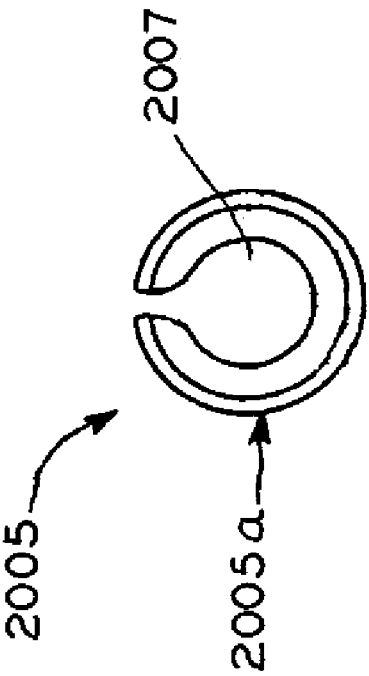
FIG. 44B is an end view of the mandrel of FIG. 44C.

Referring now to FIGS. 47, 47A, and 48, flaps 2004a-d in implant bag 2002 may be constructed as described below. Implant bag 2002 includes two buttonholes 2003 located on opposing sides thereof, shown in FIG. 48. After the weaving process is complete wherein implant bag 2002 includes two buttonholes 2003 (only one of which is shown in FIG. 48; an identical buttonhole 2003 is located on the opposite side of implant bag 2002), a cut, such as laser cut 2004, is made in implant bag 2002 to form a cross-shaped opening with flaps 2004a-2004d. Specifically, a mandrel 2005, shown in FIGS. 44A-44C, is inserted through either buttonhole 2003 such that mandrel 2005 is contained entirely within implant bag 2002. A center rod (not shown) is inserted through central aperture 2007 of mandrel 2005 and serves as a backstop for laser cut 2004 to prevent laser cut 2004 from cutting fabric beyond the buttonhole region. Once inside implant bag 2002, flaps 2004a-2004d entirely cover both mandrel ends 2005a and 2005b. Two mandrel plates are fixed on opposing ends 2005a and 2005b of mandrel 2005. The setup is then heat set to form indentations in implant bag 2002, such as those indicated by outline 2011 shown in FIG. 47A. The heating process involves the steps of scouring and heat setting, as fully described in U.S. Provisional Patent Application Ser. No. 60/654,481, filed Feb. 18, 2005, the disclosure of which is incorporated herein by reference. The step of scouring is a separate process which typically occurs prior to the heat setting step.

A laser may be utilized to cut laser cut 2004 in implant bag 2002, thereby forming flaps 2004a-d. Once the heating and laser-cutting processes are complete and indentations 2011 surround both buttonholes 2003 of implant bag 2002, the mandrel plates, the center rod, and mandrel 2005 are removed from implant bag 2002.

Although described above with respect to the formation of portions of implant bag 2002 of FIGS. 47, 47A, and 48, a similar procedure could be utilized to form portions of implant bag 1302 of FIG. 45.

G. Description of Implant Bag and Implant Tube

Figure 43:
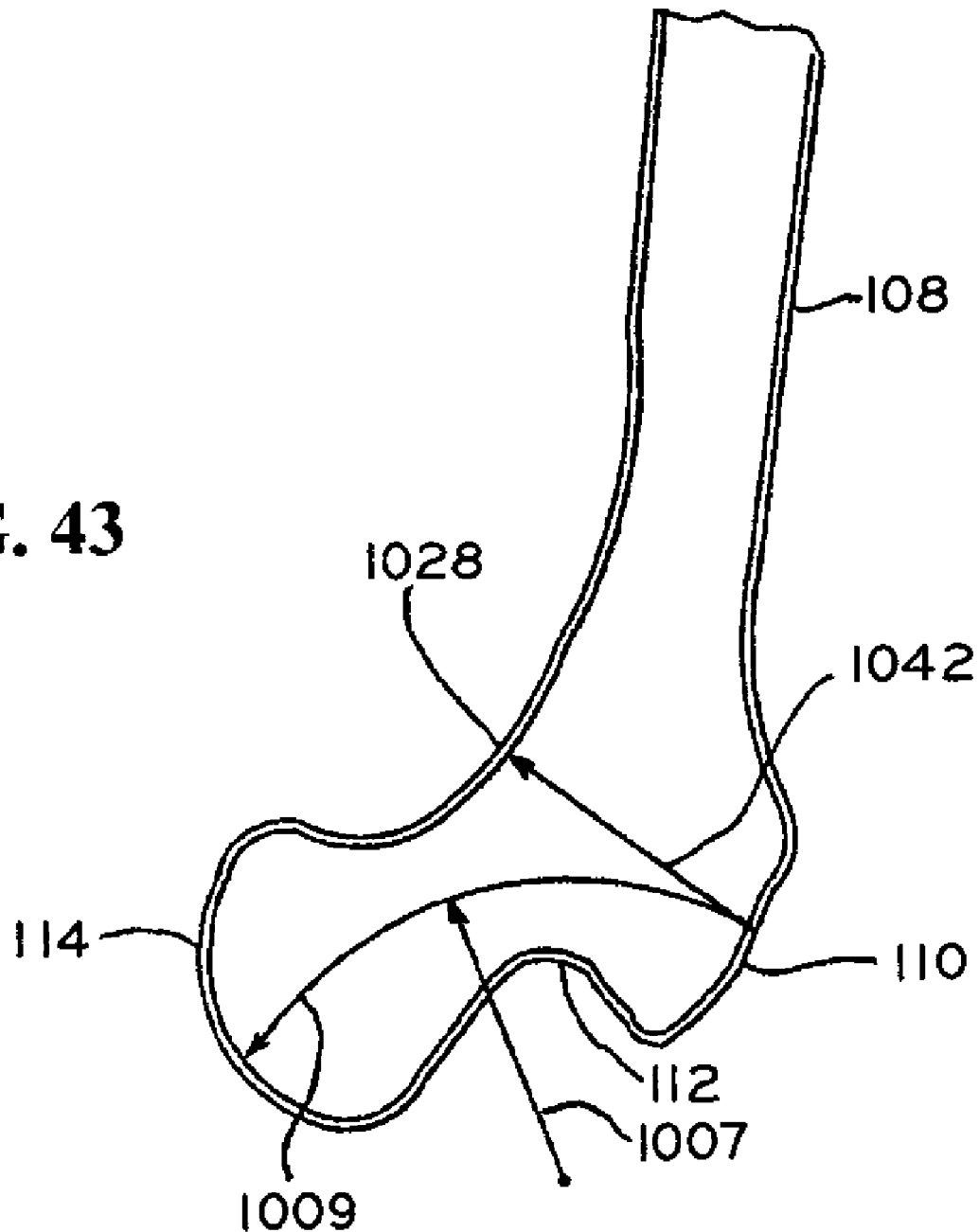
FIG. 43 is a plan view of the femur of the human patient of FIG. 1, further illustrating various depths and angles.

Referring now to FIG. 45, femoral implant 1300 includes implant bag 1302, implant tube 1304, lag tube 1306, and lag 1400 (FIG. 58). Associated instruments include implant sleeve 1308, insertion tube 1310, injection tube 1312, and fill adapter 1314, as described below. In one embodiment, the size of femoral implant 1300 is determined in part by arc length 1305 (FIG. 49A) of a central portion of implant tube 1304 and of lag tube 1306 being approximately equal to medial depth 1042 (FIG. 43) of femur 108 which extends from greater trochanter 110 to medial cortex 1028. Exemplary embodiments may include arc lengths 1305 of approximately 38 mm (1.5 in.), 48 mm (1.875 in.), or 58 mm (2.25 in.) depending upon the anatomy of the patient. Arc radius 1307 (FIG. 49A) of implant tube 1304 and of lag tube 1306 may be selected to be approximately equal to arc radius 1007 (FIG. 43) of femur 108 which is measured as the radius of a circle drawn to connect femoral head 114 and greater trochanter 110, for example, approximately 51 mm (2.0 in.) or 63 mm (2.5 in.) depending upon the anatomy of the patient. As shown in FIGS. 49C-49D, lag tube 1306 has a substantially elliptical cross-section to provide for two fill ports 1362, located 180° apart, which facilitate filling implant bag 1302 while isolating lag tube 1306 and maintaining a small implant cross-section. As shown in FIG. 59, lag 1400 may have an elliptical cross-section sized so that lag 1400 is slidingly received within lag tube 1306, as described below.

In one exemplary embodiment, lag tube 1306 is a metallic tube, e.g., stainless steel, and implant tube 1304 is formed of a biologically compatible material such as an acrylic, e.g., PMMA. Specifically, implant tube 1304 may be molded from PMMA into a rigid form.

Referring to FIGS. 49A-49D, femoral implant 1300 is formed by axially inserting lag tube 1306 within central opening 1316 extending axially through implant tube 1304, and securing implant bag 1302 over the length of implant tube 1304 while keeping distal end 1318 and proximal end 1320 of implant tube 1304 uncovered. Advantageously, femoral implant 1300 is designed so that no filler material contacts lag tube 1306 or lag 1400 such that lag 1400 may freely slide within lag tube 1306. Referring again to FIG. 45, implant bag 1302 includes a substantially cylindrical portion 1322 having distal aperture 1324 and proximal aperture 1326 through which distal end 1318 and proximal end 1320 of implant tube 1304 respectfully protrude. Implant bag 1302 further includes arm portion 1328 which extends radially from cylindrical portion 1322 and is shaped to generally conform to femoral shaft arm 258. In one embodiment, implant bag 1302 is woven and then shaped on a mandrel, as described above, while applying enough heat to reform the unstressed shape of implant bag 1302.

Referring now to FIGS. 45 and 46A-46B, in one embodiment, implant bag 1302 includes opening 1331 at end 1330. Opening 1331 may be closed, for example, by an injection molding process, in order to contain filler material in implant bag 1302. Plug 1333 for sealing opening 1331 includes walls 1334 against which opening 1331 at end 1330 of implant bag 1302 is gathered and against which molding fill 1336 and ring 1332 are injected to securely seal opening 1331 against walls 1334. In an alternative embodiment, implant bag 1302 is already sealed in the manufacture of the bag, as described above.

FIG. 46A shows approximately a quarter of the circumference of opening 1331 positioned against adjacent walls 1334. Plug 1333 advantageously includes walls 1334, which project radially from a central point 1335, so that opening 1331 may be sealed closed upon a structure having a smaller diameter than if plug 1333 had a circular surface matching the larger diameter of opening 1331. By providing radially projecting walls 1334, the perimeter distance measured along walls 1334 of plug 1333 is approximately equal to the circumference of opening 1331, even though the diameter of plug 1333 is smaller than the diameter of opening 1331.

As shown in FIG. 46B, after opening 1331 is pressed inward toward central point 1335 so that the entire circumference is in contact with walls 1334, molding fill 1336 and ring 1332, which couples and retains molding fill 1336 securely against opening 1331 and walls 1334, may be provided, for example, by injection molding. Alternatively, other cross-sectional shapes may be utilized for plug 1333 so that opening 1331 may be sealed within a small diameter that will fit through access 101 in femur 108.

Referring now to FIGS. 49A-49D, in construction, lag tube 1306 is inserted within central opening 1316 of implant tube 1304. Cylindrical portion 1322 (FIG. 45) of implant bag 1302 is slid over implant tube 1304. Distal end 1318 and proximal end 1320 of implant tube 1304 are subsequently at least partially overmolded, for example, by injection molding, as described below. In one embodiment, implant tube 1304 is at least partially overmolded with the same material used to construct implant tube 1304, e.g., PMMA. Overmolding secures cylindrical portion 1322 of implant bag 1302 to implant tube 1304.

Two cylindrical flanges 1338 (FIGS. 45 and 49A) are located adjacent each of distal end 1318 and proximal end 1320 of implant tube 1304. Flanges 1338 facilitate securing cylindrical portion 1322 of implant bag 1302 to implant tube 1304. As shown in FIG. 49A, retaining ring 1340 is positioned between each pair of cylindrical flanges 1338 to hold cylindrical portion 1322 of implant bag 1302 in position during overmolding and to provide thermal insulation to implant bag 1302 during the overmolding process so that implant bag 1302 is not heat embrittled other than where contacted by molding material. Subsequent to placement of retaining rings 1340, cylindrical molding fill 1342 is injected adjacent retaining rings 1340 between cylindrical flanges 1338.

In an alternative embodiment, retaining rings 1340 may be replaced by clips 2024, shown in FIG. 53A. Clip 2024 may be positioned in a substantially similar position as retaining ring 1340, as described above. In one embodiment, flange 2026, shown in FIG. 53D, of clip 2024 faces proximally at proximal end 1320 and distally at distal end 1318. As shown in FIGS. 53A, 53B, and 53C, clip locking portions 2024a and 2024b provide the ability to close and lock clip 2024 around implant tube 1304 and implant bag 1302. Clips 2024 are closed such that the locking region defined by portions 2024a and 2024b are oriented 180 degrees from regions where an overmold tool will gate into the finished part, i.e., regions where molten material enters the finished part. Where the overmold tool gates into the finished part, a higher pressure is exerted on the finished part due to the nature of the injection molding process. By orienting the locking region of clips 2024 away from this increased pressure, the risk of dislocation of clips 2024 during the overmolding process is decreased.

As shown in FIGS. 49A-49B, in order to retain lag tube 1306 within implant tube 1304, distal overmolding 1344 is injected over distal end 1318 of implant tube 1304. In one embodiment, distal overmolding 1344 includes distal tabs 1346 which radially overlap distal end 1348 of lag tube 1306, thereby preventing lag tube 1306 from distal movement out of implant tube 1304. As shown in FIGS. 49A, 49C, and 49D, proximal end 1320 of implant tube 1304 may be injection molded with proximal overmolding 1350, including proximal tabs 1352 which radially overlap top and bottom portions of proximal end 1354 of lag tube 1306, thereby preventing lag tube 1306 from sliding proximally out of implant tube 1304.

Referring still to FIGS. 49A, 49C, and 49D, proximal end 1320 of implant tube 1304 features fill ports 1362 which are isolated from central opening 1316 by walls 1364. Advantageously, fill ports 1362 provide paths for bone cement or other filler to be delivered from proximal end 1320 of implant tube 1304 into the interior of implant bag 1302, without exposing lag tube 1306 or central opening 1316 to the filler. Central opening 1316 has a generally elliptical cross-section and is formed in part by walls 1364. Fill ports 1362 are located outside of walls 1364 which are approximately parallel to the major axis of the generally elliptical cross-section of central opening 1316. As shown in FIG. 49D, fill ports 1362 are defined by flange 1321 and by walls 1364. In construction, the distal end of flange 1321 is located within the interior of bag 1302, thus fill ports 1362 provide paths for filling implant bag 1302.

The isolation of lag tube 1306 from the filler is desired in the event that later removal of implant 1300 is required. If lag tube 1306 is not cemented or otherwise adhered to implant tube 1304, removal of proximal tabs 1352 of implant tube 1304 allows lag tube 1306 to be easily removed from implant 1300 by sliding lag tube 1306 out proximal end 1320 of implant tube 1304. Similarly, removal of distal tabs 1346 of implant tube 1304 allows lag tube 1306 to be easily removed from implant 1300 by sliding lag tube 1306 out distal end 1318 of implant tube 1304.

Referring now to FIGS. 45 and 50-52, in one embodiment, insertion tube 1310 may be coupled to implant 1300, as described below, to facilitate handling of implant 1300 and insertion thereof into cavity 224. Injection tube 1312 and fill adapter 1314 provide for coupling of a filler dispenser and for delivery of bone cement or other filler into implant bag 1302, which, subsequent to implantation, fills cavity 224 and femoral shaft arm 258 in order to anchor and stabilize lag 1400, as described below, in femur 108.

Referring now to FIGS. 45 and 49A, proximal end 1320 of implant tube 1304 includes bosses or projections 1356 for releasably coupling insertion tube 1310 to implant 1300. Specifically, bosses 1356 are received within arcuate channels or recesses 1359 at the interior of proximal end 1358 of insertion tube 1310. Arcuate channels 1359 include a circumferential and a radial component. Upon rotation and slight axial translation of insertion tube 1310 relative to implant 1300, bosses 1356 translate in arcuate channels 1359 until releasably locking within receptacles 1360 defined at the ends of arcuate channels 1359 and through the wall of insertion tube 1310; thereby coupling insertion tube 1310 and implant 1300, shown in FIG. 50.

Referring now to FIGS. 51-52, distal end 1366 of injection tube 1312 is adapted to couple to proximal end 1320 of implant tube 1304 while plugging central opening 1316 and diverting filler from fill adapter 1314 into fill ports 1362 of implant tube 1304. Boss 1368 protrudes distally from injection tube 1312 and is sized to match and extend into central opening 1316 of implant tube 1304 and into the interior of lag tube 1306, thereby preventing filler from contacting or entering lag tube 1306. Shoulders 1370 defined at opposite sides of boss 1368 project axially from distal end 1366 of injection tube 1312. Upon coupling of injection tube 1312 and implant 1300, shoulders 1370 overlap the radially interior sides of the distal ends of walls 1364 (FIGS. 49C-49D) and abut the portion of proximal end 1354 (FIG. 49A) of lag tube 1306 not covered by proximal tabs 1352. The substantially matching elliptical shape of boss 1368 and the interior of lag tube 1306 generally ensure that diverting apertures 1372 of injection tube 1312 are aligned with fill ports 1362, thereby providing a pathway with lap joints for filler to be conveyed through injection tube 1312 into the interior of implant bag 1302.

Referring now to FIGS. 45 and 50, raised surface 1374, which extends longitudinally along at least a portion of the length of injection tube 1312, is received by slot 1311 of insertion tube 1310 to fix the rotational alignment of injection tube 1312 and insertion tube 1310. Engagement of bosses 1356 of implant tube 1304 and receptacles 1360 of insertion tube 1310 fix the rotational alignment of implant 1300 and insertion tube 1310, as described above. The combination of the rotational alignment of injection tube 1312 with insertion tube 1310 and of implant 1300 with insertion tube 1310 provides alignment of diverting apertures 1372 with fill ports 1362. Injection tube 1312 is cannulated so that single fill aperture 1376 at the proximal end thereof branches into two diverting apertures 1372 at distal end 1366. Filler material enters fill aperture 1376 and is directed through diverting apertures 1372 into and through fill ports 1362. Fill adapter 1314 includes arcuate slots 1380 for receiving bosses 1378 of insertion tube 1310, thereby releasably coupling fill adapter 1314 to insertion tube 1310 and capturing injection tube 1312 there between. Fill adapter 1314 may include internal threads 1382 for coupling a standard bone cement dispenser thereto.

In an alternative embodiment shown in FIGS. 54A-54D, implant 2000 including implant bag 2002 and implant tube 2012, substantially similar to implant tube 1304 described above, is assembled onto implant utility tube 2050. Implant utility tube 2050 includes slot or recess 2051, shown in FIG. 54B, to mate with the tabs or projections of bayonet lock 2015 of implant tube 2012, shown in FIG. 54C, when implant utility tube 2050 is slid onto implant tube 2012 in the general direction of arrow D and thereafter rotated 45 degrees in the general direction of arrow E to secure implant utility tube 2050 to implant 2000.

H. Description of Lag

Described below are several lags which may be used to anchor any of the implants described herein in the bone of the patient. For the purposes of this document, lag is defined as an anchoring device. In one embodiment shown in FIGS. 55-57, lag 264 includes a plurality of radially expanding fingers 928 positioned at the distal end thereof. Lag 264 may have an elliptical cross-sectional shape such as to match the shape of central opening 1316 of implant tube 1304. As shown in FIG. 57, radially expanding fingers 928 can be deformed to radially expand and engage femur 108 in femoral head arm 256, as described below.

As shown in FIG. 55, each radially expanding finger 928 of lag 264 is defined between a pair of respective outer circumferential grooves 930. Outer circumferential grooves 930 and inner circumferential groove 932 each create respective hinge points for radially expanding fingers 928 and facilitate deformation thereof into the position shown in FIG. 57. As shown in FIG. 55, the central portion of each radially expanding finger 928 may include small central cutouts 929 on one or opposing sides thereof. Cutouts 929 further facilitate deformation of radially expanding fingers 928 into the position shown in FIG. 57 by further reducing, and, therefore, weakening the material proximate the hinge points created by groove 932. In one exemplary embodiment, radially expanding fingers 928 are provided with additional hinge points, which allow for radially expanding fingers 928 to be deformed into shapes differing from the triangular shape shown in FIG. 57. For example, in one exemplary embodiment (not shown), four hinge points may be provided such that radially expanding fingers 928 form a trapezoidal shape upon deformation.

In an alternative embodiment shown in FIGS. 58-61, lag 1400, which is arcuate and cannulated, may be anchored within femoral head arm 256, as described below, and includes many of the characteristics and aspects of lag 264 described above. As shown in FIG. 59, lag 1400 may have a substantially elliptical cross-section throughout its entire length with the exterior dimensions of lag 1400 being slightly less than the interior dimensions of lag tube 1306 of femoral implant 1300. In one embodiment, major axis 1403 (FIG. 59) of the elliptical cross-section is coplanar with the arc defined by longitudinal axis 1401 (FIG. 58) of lag 1400.

As shown in FIG. 59, major axis 1403 of lag 1400 may be slightly less than the diameter of a reamer head used to form femoral head arm 256, as described above. In one embodiment, major axis 1403 is approximately 12.7 mm (0.5 in.) and fingers 1402 expand to approximately 25.4 mm (1.0 in.) along major axis 1403 and 21.6 mm (0.85 in.) along minor axis 1405. In one embodiment, available size selections for lag 1400 are arced longitudinally to conform to typical femoral anatomy, for example, arc radius 1007 (FIG. 43) of approximately 51 mm (2.0 in.) or 63 mm (2.5 in.). Lag 1400 may also be made in a plurality of lengths, therefore accommodating a typical range of sizes of femoral anatomy.

Figure 62:
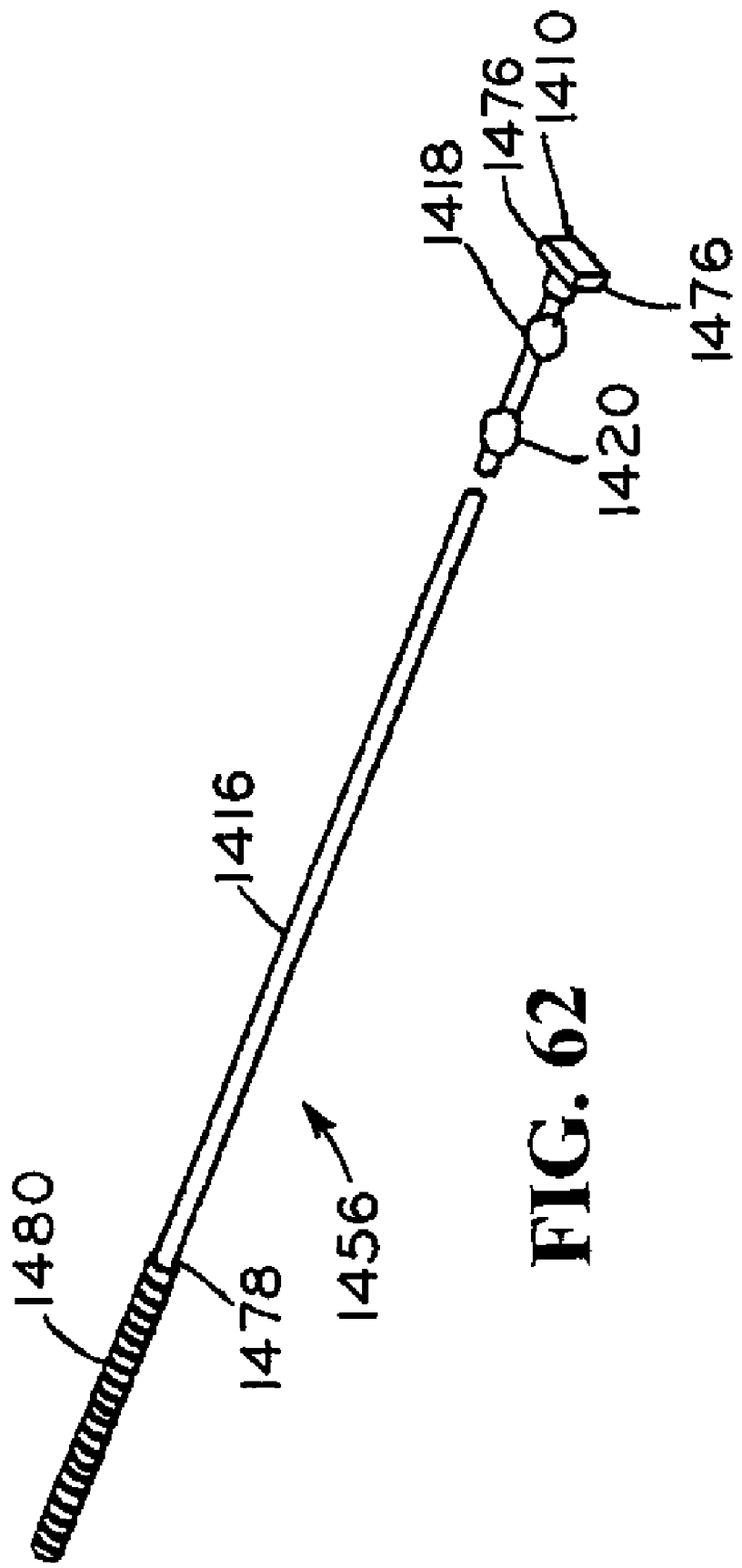
FIG. 62 is a perspective view of an actuation cable.

As shown in FIGS. 58 and 60-61, lag 1400 may include a plurality of radially expandable tines or fingers 1402 between body 1404 and distal end 1406. Distal end 1406 defines distal apertures 1408 (only one of which is shown) positioned 1800 apart. As shown in FIGS. 60-62, anchor 1410 may be engaged into distal apertures 1408, thereby enabling compression to be applied to lag 1400 to expand fingers 1402, shown in FIG. 61 and described below.

In one embodiment of lag 1400, notched regions that locate bend points for fingers 1402 have wall thickness 1415, shown in FIG. 60, which is a minimum of about 0.46 mm (0.018 in.) and may be a maximum of about 1.02 mm (0.040 in), or preferably about 0.76 mm (0.030 in). These thicknesses of wall thickness 1415 require a deformation force between about 181 kg (400 lbs.) and 363 kg (800 lbs.), or preferably about 227 kg (500 lbs.). The wall thickness of the remaining portions of lag 1400, in one embodiment, is a minimum of about 1.34 mm (0.053 in.). Lag 1400 may be constructed of, for example, stainless steel, and be electro-plated, electro-polished, or glass bead blasted for a matte finish.

Referring now to FIG. 62, anchor 1410 includes oppositely oriented engagement ears 1476 which extend along major axis 1403 (FIG. 59) of lag 1400 upon insertion into lag 1400. Anchor 1410 is sized to be inserted from proximal end 1412 of lag 1400 and to be positioned at distal end 1406. Distal apertures 1408 are formed so that a 90 degree rotation of anchor 1410 rotates engagement ears 1476 perpendicular to major axis 1403 and engages ears 1476 within apertures 1408. Referring again to FIG. 58, proximal end 1412 of body 1404 may include insertion receptacles 1414 for coupling of an inserting or retracting instrument to insert or retract lag 1400 through lag tube 1306 and/or into or out of femur 108.

Referring to FIGS. 60-62, cable 1416, for example, a cable braided from stainless steel wire, is coupled to tension anchor 1410. Distal spacer 1418 and proximal spacer 1420 are cannulated and are strung on cable 1416. Distal spacer 1418 is held in position on cable 1416, for example, by crimped beads (not shown) so that distal spacer 1418 is free to rotate on cable 1416 and is held in position adjacent fingers 1402. Because of the arcuate shape of lag 1400 and the nature of fingers 1402, finger 1402 located on the concave side of lag 1400 may tend to expand inwardly rather than outwardly. By positioning distal spacer 1418 adjacent fingers 1402, even if one of fingers 1402 initially folds inward, as distal end 1406 is compressed toward proximal end 1412, inwardly expanding fingers 1402 contact distal spacer 1418. As compression of lag 1400 continues, fingers 1402 must instead expand radially outward because fingers 1402 are prevented from expanding radially inward by contact with spacer 1418. Additionally, in order to radially substantially center cable 1416 and to prevent cable 1416 from damaging inner lag tube surface 1422 of lag tube 1306, proximal spacer 1420 may be positioned near proximal end 1412 of lag 1400.

Figure 63:
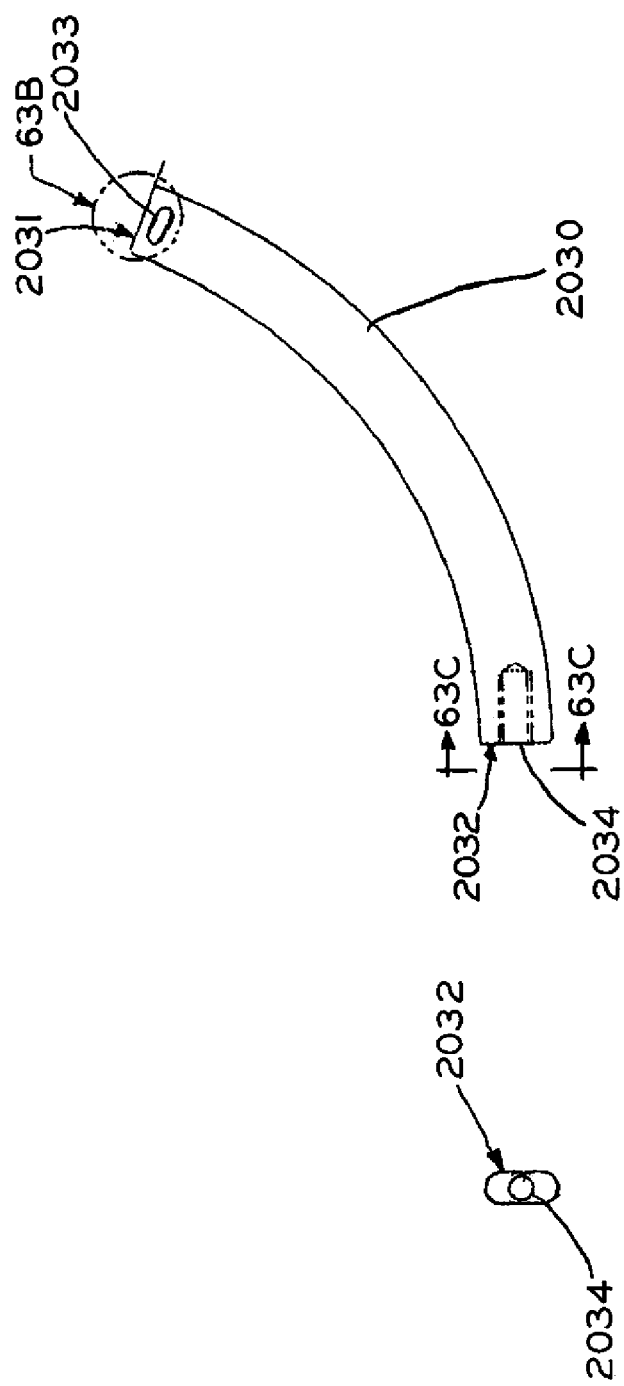
FIG. 63A is a plan view of a lag support.
FIG. 63B is a fragmentary view of a portion of the lag support of FIG. 63A.
FIG. 63C is a proximal end view of the lag support of FIG. 63A, taken along line 63C-63C of FIG. 63A.

In an alternative embodiment, lag support 2030, shown in FIGS. 63A-63C, may be used to prevent inward expansion of fingers 1402. Lag support 2030 includes distal end 2031 and proximal end 2032. Distal end 2031 includes aperture 2033 and proximal end 2032 includes recess 2034. In one embodiment, recess 2034 has internal threads. Lag support 2030 is curved or arcuate and made of a suitable material, in one embodiment, 316L stainless steel.

Figure 64:
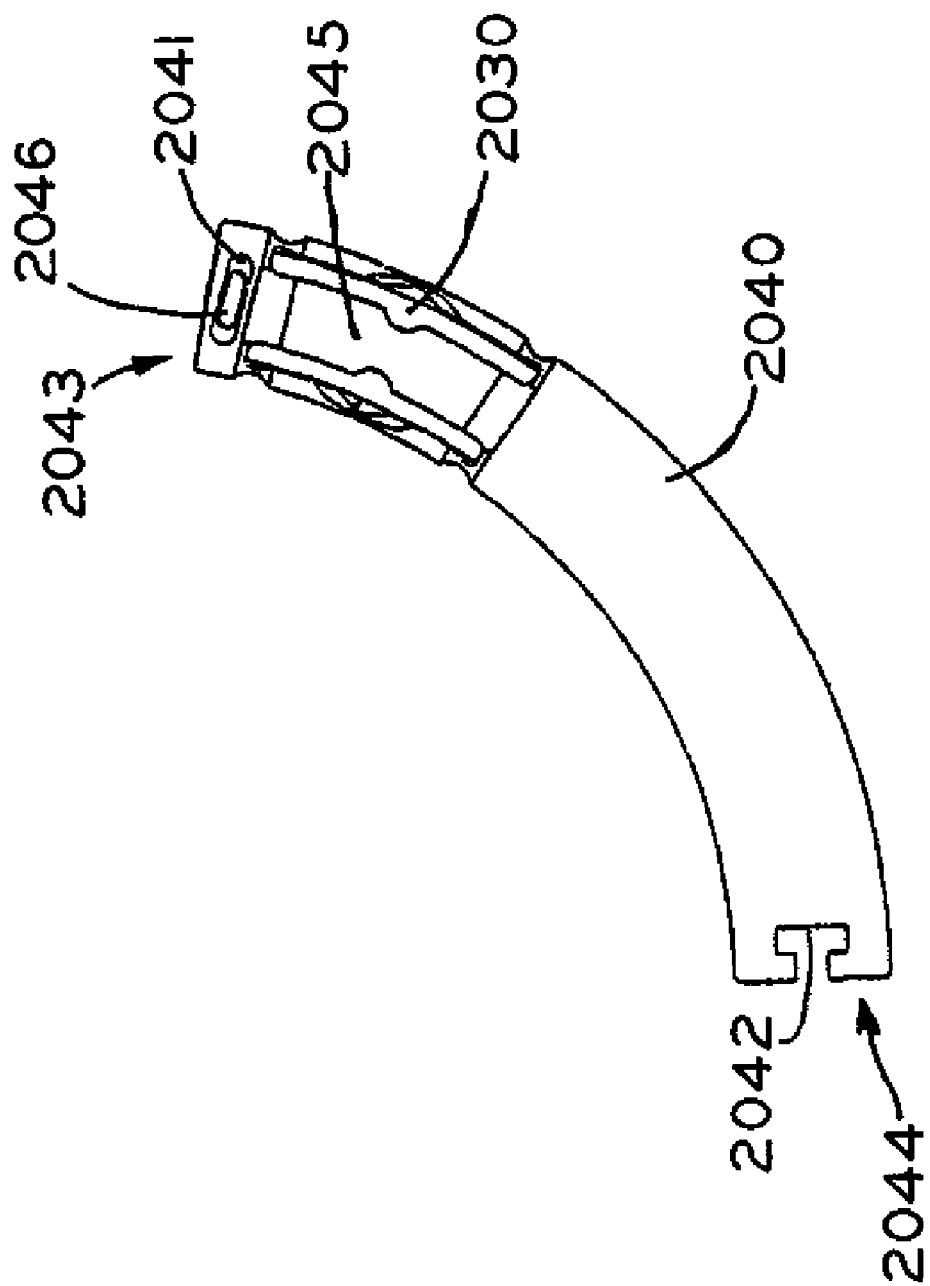
FIG. 64 is a plan view of a lag according to an alternative embodiment.

Lag support 2030 may also support lag 2040, shown in FIG. 64, which is substantially similar in many aspects to lag 1400, as described above. Lag 2040 includes aperture 2041 located at distal end 2043. Lag support 2030 is inserted into lag 2040 until distal end 2031 of lag support 2030 is level with distal end 2043 of lag 2040. Transverse pin 2046 is inserted through apertures 2041 and 2033 and forms a press-fit engagement with apertures 2033 of lag support 2030. Transverse pin 2046 is dimensioned to extend beyond both sides of lag support 2030 to provide a locking engagement between lag 2040 and lag support 2030. In an alternative embodiment (not shown), lag support 2030 may extend a short distance beyond distal end 2043 of lag 2040. Lag 2040 includes fingers 2045 which are substantially similar to fingers 1402, as described above.

I. Implant and Lag Insertion

Figure 65:
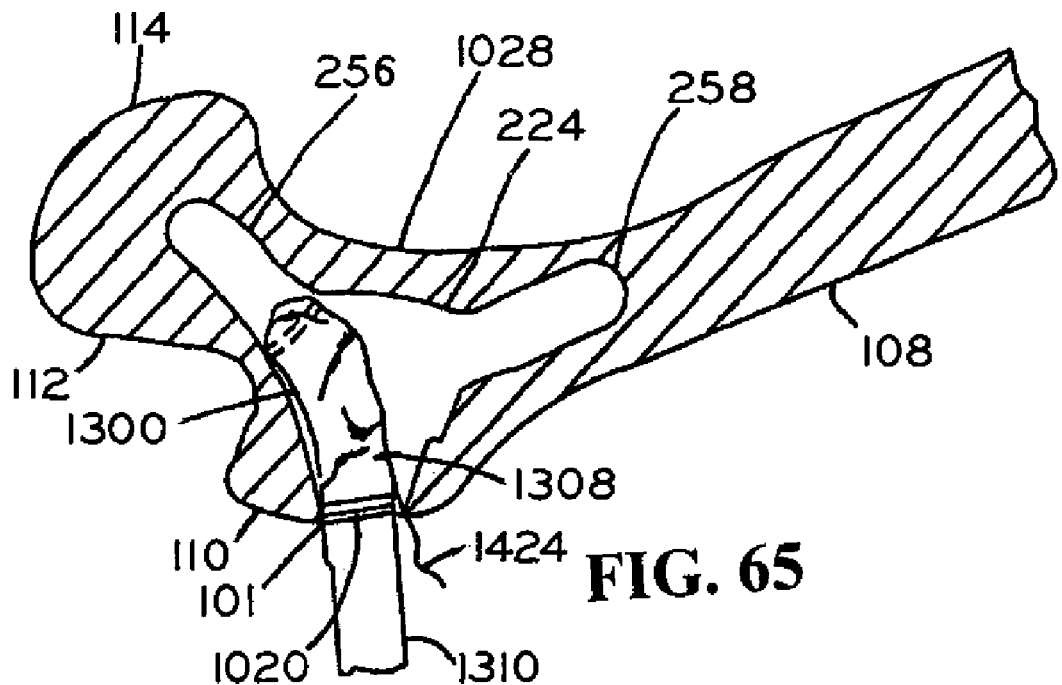
FIG. 65 is a partial sectional view of the femur of the human patient of FIG. 1, further illustrating the implant cavity, femoral shaft arm, femoral head arm, and the implant of FIG. 45.
Figure 66:
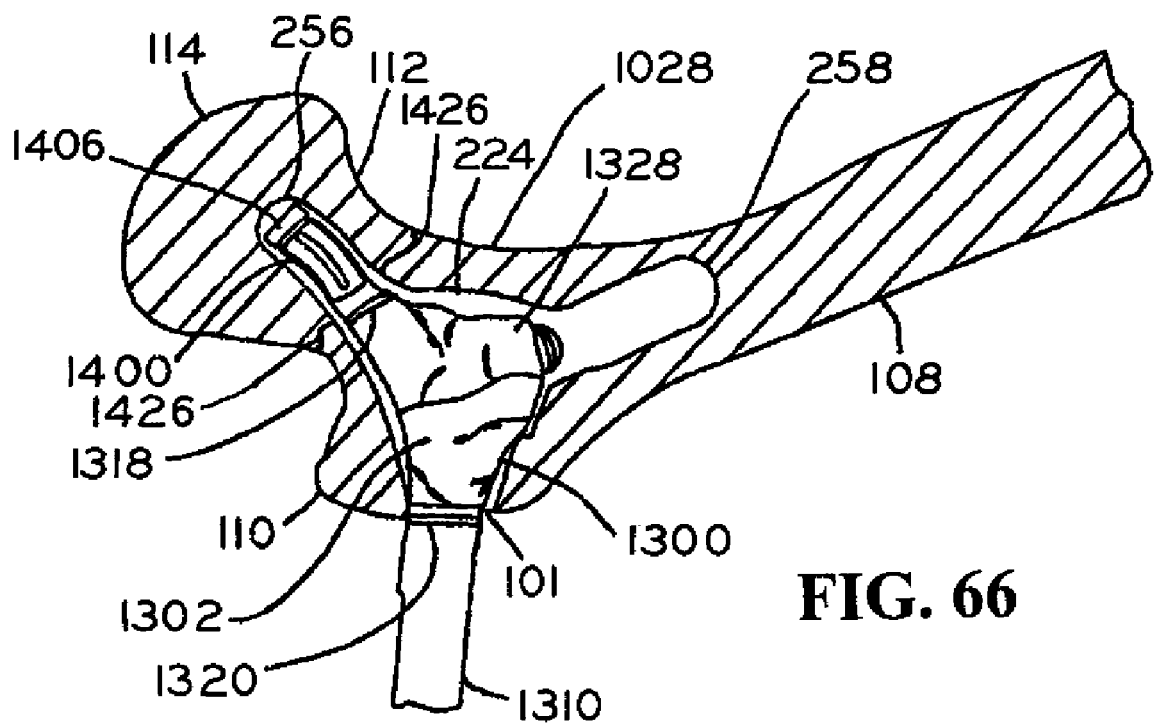
FIG. 66 is a partial sectional view of the femur of the human patient of FIG. 1, further illustrating further deployment of the implant of FIG. 45 into the femoral head arm.

Referring now to FIGS. 45 and 65-66, in one embodiment, insertion of implant 1300 into cavity 224 of femur 108 is facilitated by generally cylindrical implant sleeve 1308, which has openings 1309 (FIG. 45) at opposite ends thereof and which may be wrapped or slid over the outer surface of implant 1300 to compress implant bag 1302 into a generally cylindrical cross-section suitable for insertion through access 101. As shown in FIG. 65, implant 1300 may be positioned so that the arc shape of implant 1300 extends toward femoral head arm 256. Once implant 1300 is positioned within cavity 224, string 1424 or another protrusion coupled to implant sleeve 1308 may be pulled or otherwise tensioned in order to slide implant sleeve 1308 proximally over insertion tube 1310 and out of cavity 224, thereby exposing implant bag 1302, shown in FIG. 66.

Figure 67:
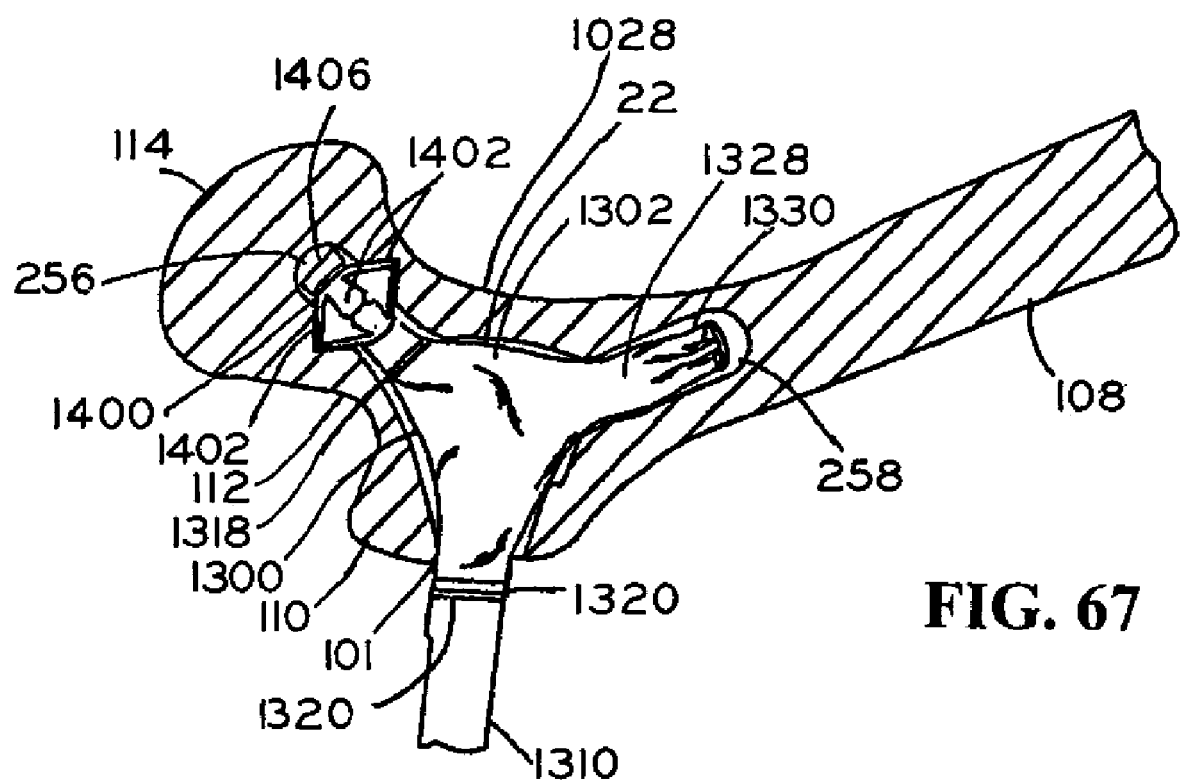
FIG. 67 is a partial sectional view of the femur of the human patient of FIG. 1, further illustrating the deployment of the expandable fingers and extension of the implant bag into the femoral shaft arm.

Referring now to FIG. 66, lag 1400 may then be inserted through lag tube 1306 of femoral implant 1300 so that distal end 1406 of lag 1400 extends into femoral head arm 256, for example, to a central position within femoral head 114, or at least so that lag 1400 and implant 1300 span fracture line 1426 in femur 108. Referring now to FIG. 67, fingers 1402 of lag 1400 may then be expanded into bone adjacent femoral head arm 256, thereby anchoring lag 1400 relative to femoral head 114. The actuation of fingers 1402 is described further below. Subsequently, implant bag 1302 may be filled with bone cement or other filler, thereby expanding arm portion 1328 of implant bag 1302 into femoral shaft arm 258 to anchor implant 1300 in femur 108, shown in FIG. 67 with a partially filled implant bag 1302.

Figure 68:
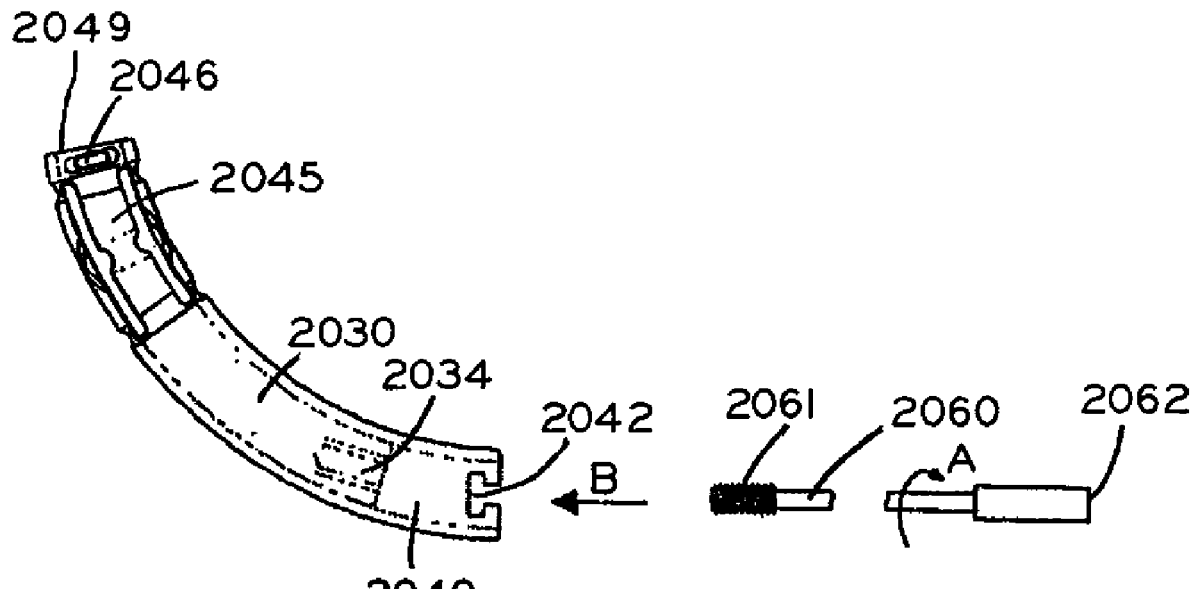
FIG. 68 is a plan view of the lag of FIG. 64, further illustrating the path of insertion of an actuation cable.
Figure 69:
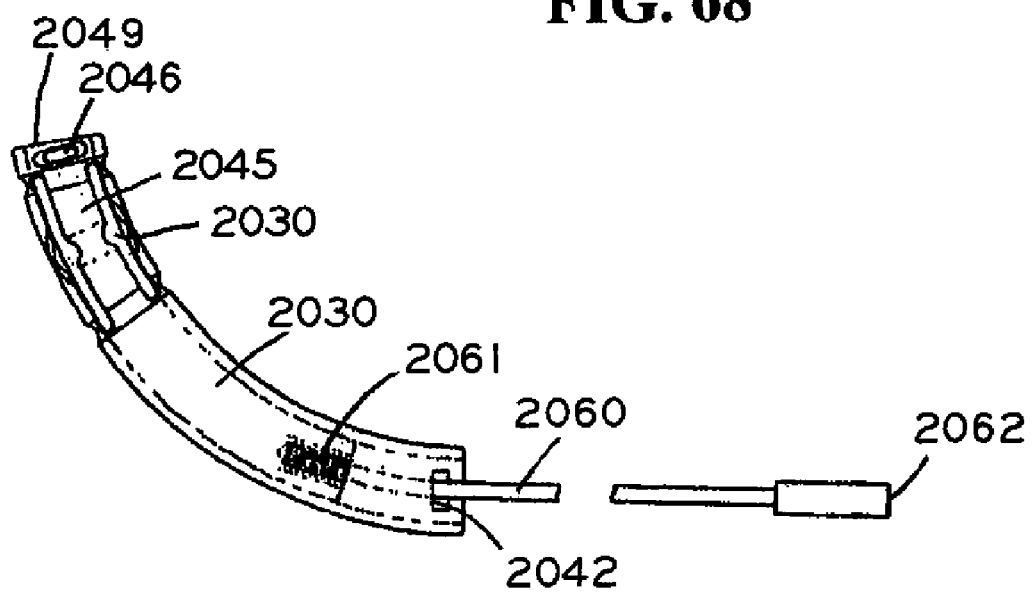
FIG. 69 is a cross-sectional view of the lag of FIG. 64, further illustrating the actuation cable engaged with the lag support of FIG. 63A.
Figure 70:
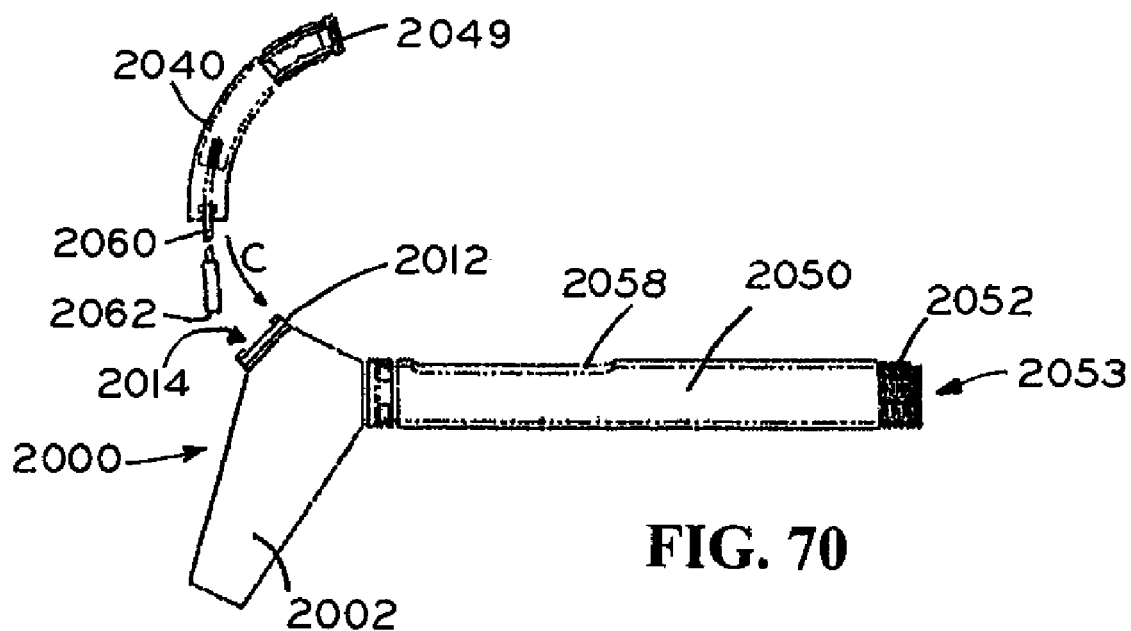
FIG. 70 is a plan view of the implant bag of FIG. 47, the lag of FIG. 64, and the implant utility tube coupled to the implant bag.
Figure 71:
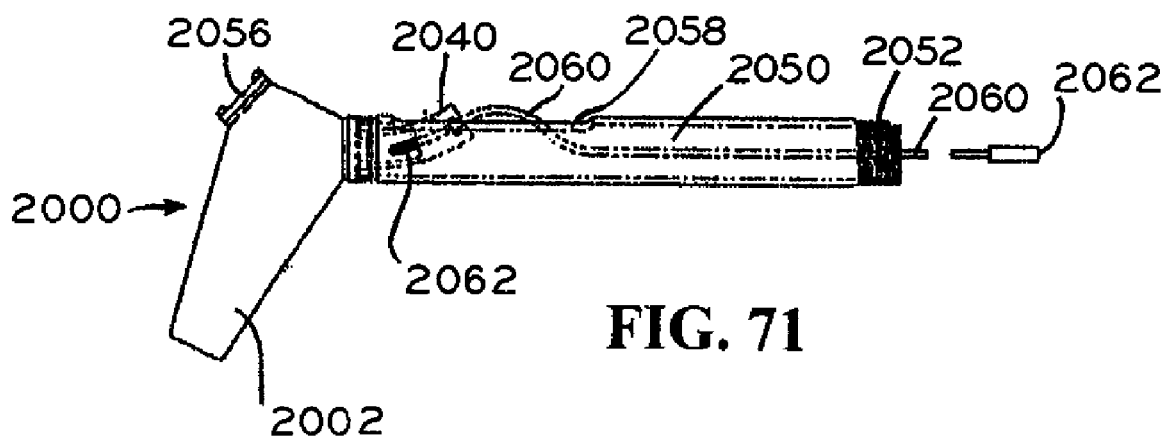
FIG. 71 is a plan view of the implant bag of FIG. 47 and the implant utility tube with the lag of FIG. 64 inserted in the implant bag and extending into the implant utility tube.

In an alternative embodiment, implant 2000 may be inserted into cavity 224 via similar instrumentation as described above with respect to implant 1300. Referring now to FIGS. 68-69, threaded end 2061 of lag cable 2060 is inserted in the direction of arrow B into threaded recess 2034 of lag support 2030, shown in dashed lines in FIG. 68, and turned clockwise or in the direction of arrow A to thread threaded end 2061 of lag cable 2060 and threaded recess 2034 of lag support 2030 together. Referring now to FIGS. 70-71, lag 2040, lag support 2030, and attached lag cable 2060 are placed into the previously assembled implant 2000 by inserting lateral tip 2062 of lag cable 2060 and lag 2040 into the opening in distal end 2014 of implant tube 2012 in the general direction indicated by arrow C. Lag 2040 is slid through implant tube 2012 until distal end 2049 of lag 2040 is flush with medial face 2056 of implant tube 2012. A portion of the proximal end of lag 2040 and lag cable 2060 protrude out opening 2058 of implant utility tube 2050 once fully inserted, shown in FIG. 71.

Figure 72:
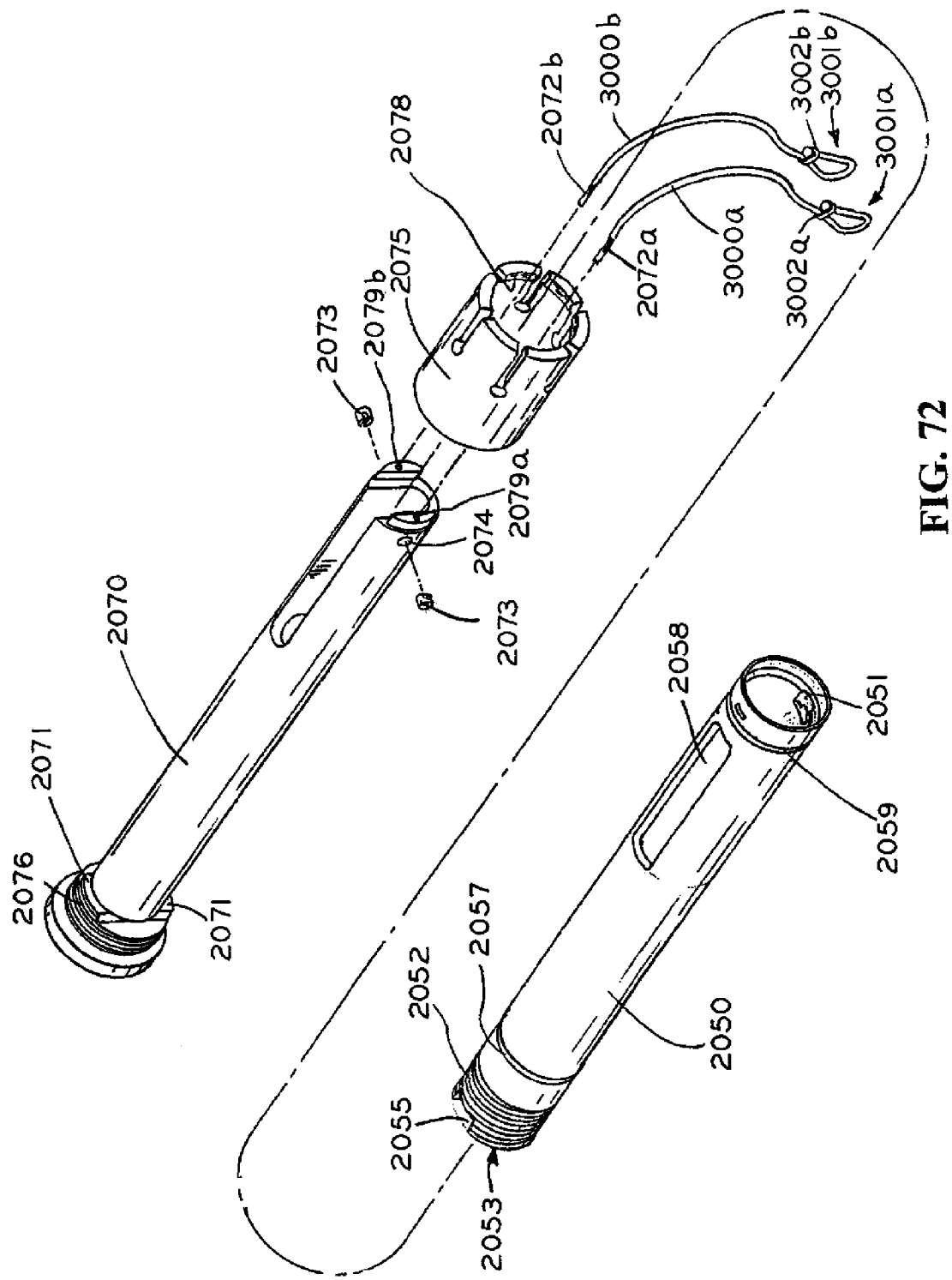
FIG. 72 is an exploded perspective view of the implant utility tube, a spring guide, and a collet nut.

Referring now to FIG. 72, spring guide 2070 includes wires 3000a and 3000b attached thereto via holding pins 2073. Compressed portions 2072a and 2072b of wires 3000a and 3000b, respectively, are inserted through apertures 2079a and 2079b in spring guide 2070, respectively. Holding pins 2073 pass through apertures 2074 in spring guide 2070 and engage compressed portions 2072a, 2072b, thereby securing wires 3000a and 3000b via a friction-fit engagement. Wires 3000a and 3000b are, in one embodiment, made of nitinol, or any other suitable shape-memory metal. Wires 3000a and 3000b facilitate extension of implant bag 2002 into femoral shaft arm 258, as described below. Wires 3000a, 3000b may include, in one embodiment, ends 3001a, 3001b generally formed by folding wires 3000a, 3000b back onto themselves. Ends 3001a, 3001b are secured in the shape shown in FIG. 72 by fasteners 3002a, 3002b. Ends 3001a, 3001b further facilitate extension of implant bag 2002 into femoral shaft arm 258.

Figure 73:
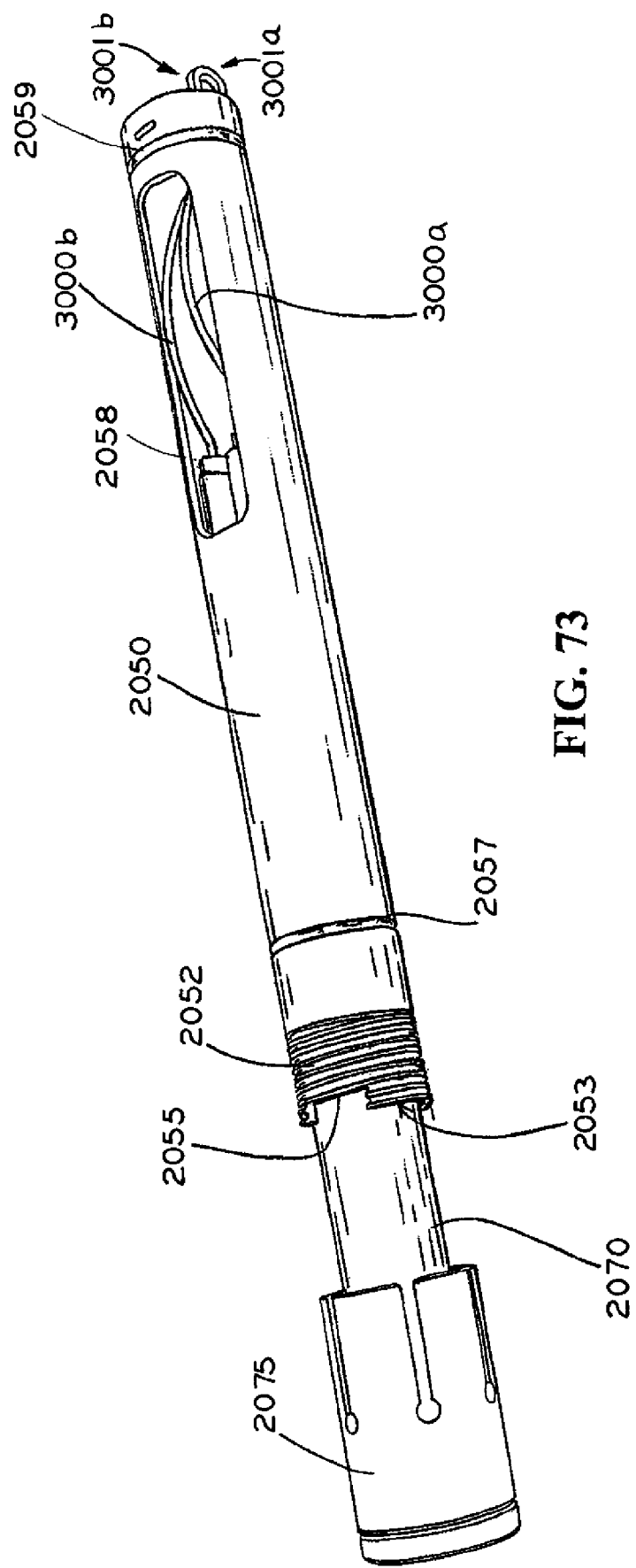
FIG. 73 is a perspective view of the implant utility tube, the spring guide, and the collet nut of FIG. 72 partially assembled.
Figure 74:
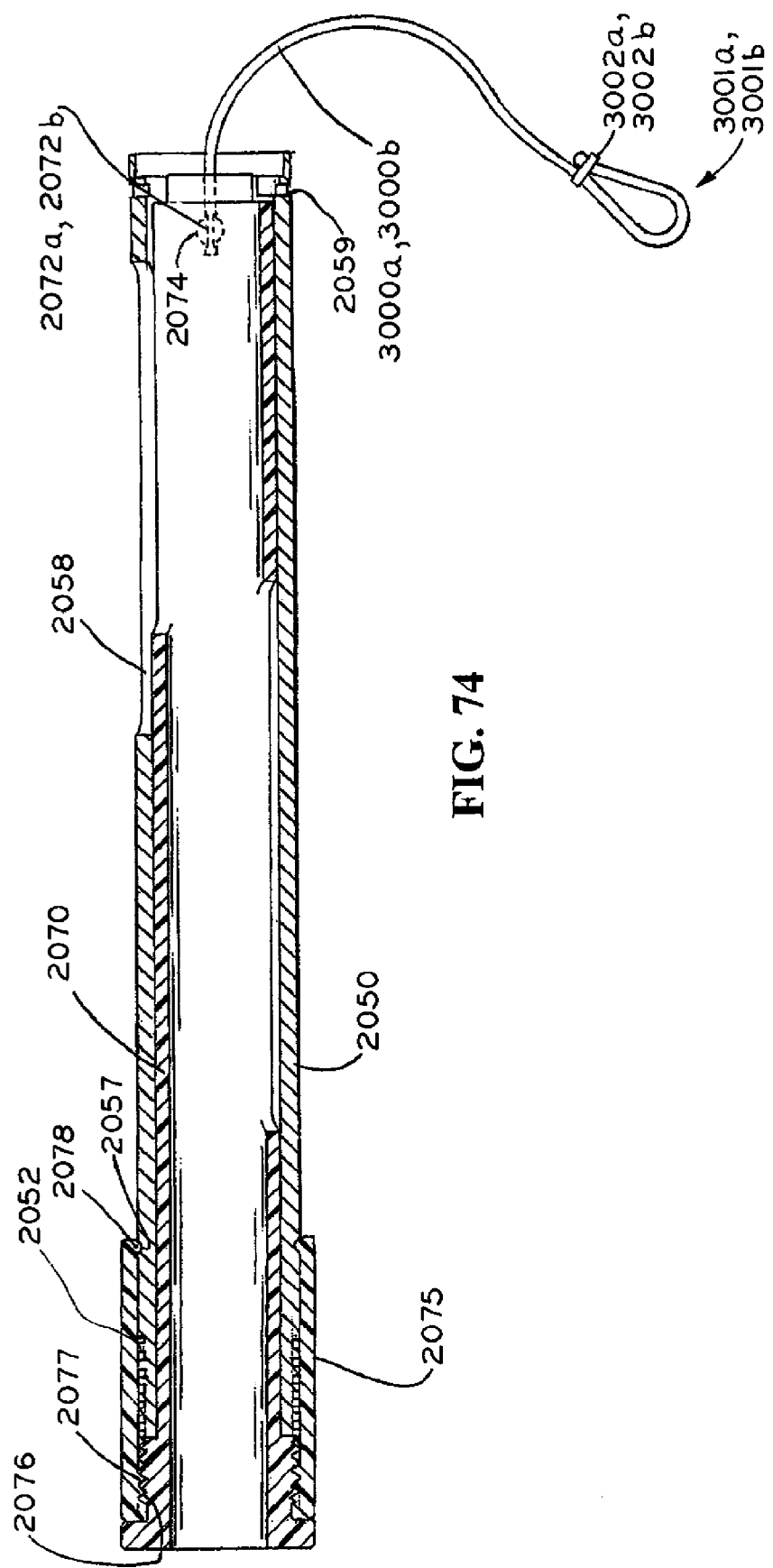
FIG. 74 is a cross-sectional view of the implant utility tube, the spring guide, and the collet nut assembly of FIGS. 72-73.

Referring now to FIGS. 72-74, spring guide 2070 is inserted into lateral end 2053 of implant utility tube 2050. Spring guide 2070 includes tabs 2071 to engage grooves 2055 of implant utility tube 2050 when assembled. Tabs 2071 each include threads 2076 which complete threads 2052 on implant utility tube 2050. Collet nut 2075 facilitates securing spring guide 2070 to implant utility tube 2050. Collet nut 2075 includes threaded interior portion 2077 which engages threads 2076 of spring guide 2070. Collet nut 2075 includes radially inwardly extending ribs 2078 which engage circumferential groove 2057 of implant utility tube 2050. Such an arrangement locks spring guide 2070 with implant utility tube 2050, shown in FIG. 74. In one embodiment, wires 3000a, 3000b may extend partially outside implant utility tube 2050 via opening 2058, shown in FIG. 73.

Figure 75:
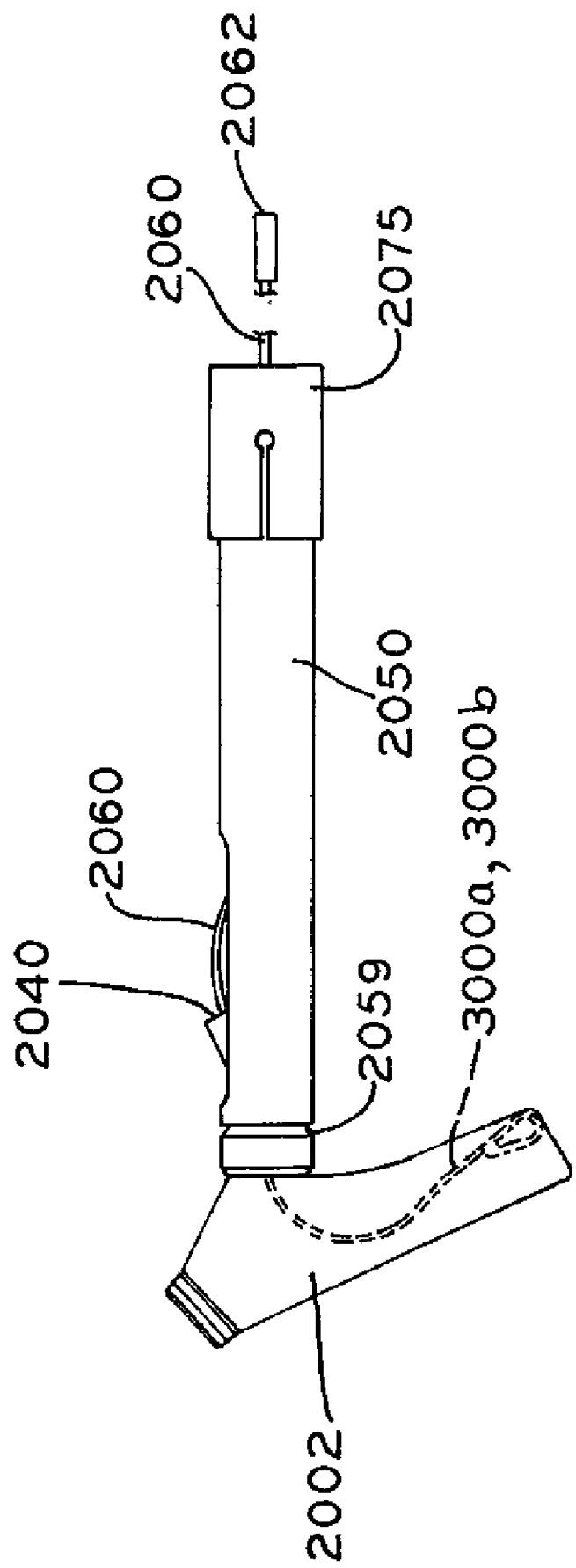
FIG. 75 is a plan view of the implant utility tube, the spring guide, and the collet nut assembly assembled to the implant bag of FIG. 47.

Referring now to FIG. 75, lag cable 2060 extends out the proximal end of collet nut 2075 and wires 3000a, 3000b pass into implant bag 2002 via fill ports 1362 (FIGS. 49C-49D). FIG. 75 also shows implant bag 2002 partially folded for insertion into insertion sleeve 2090 (FIG. 76).

Figure 76:
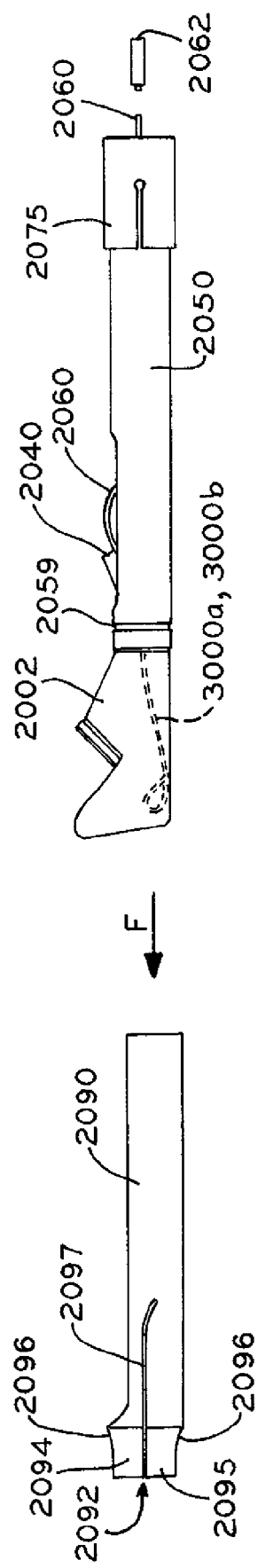
FIG. 76 is a plan view of the assembly of FIG. 75, further illustrating the direction of insertion of the assembly into an insertion sleeve.

Referring now to FIGS. 76-78, insertion sleeve 2090 may be used to introduce implant bag 2002 into cavity 224. As shown in FIGS. 77A-77B, insertion sleeve 2090 includes longitudinal opening 2091 (FIG. 77B) and internal taper 2098 (FIG. 77A) to facilitate insertion of implant bag 2002 into cavity 224. As shown in FIGS. 77A, 77C, and 77D, insertion sleeve 2090 also includes slots 2097, only one of which is shown, disposed on both sides of insertion sleeve 2090. Slots 2097 define upper portion 2094 and lower portion 2095 to facilitate insertion of implant bag 2002, as described below. Corners 2093 are provided at distal end 2092 of insertion sleeve 2090 and are rounded to protect implant bag 2002 from tearing. Any other suitable configuration for corners 2093 may be utilized which protect implant bag 2002 from tearing. Slot 2097 is curved to allow greater flexibility to push implant bag 2002 through upper portion 2094 and lower portion 2095. Providing a curve in slot 2097 increases the strength of insertion sleeve 2090 and decreases the chance of fracturing insertion sleeve 2090 while still permitting slot 2097 to end in the center of distal end 2092. In an alternative embodiment (not shown), insertion sleeve 2090 does not include slot 2097.

Referring now to FIGS. 76 and 78, implant bag 2002 is introduced into insertion sleeve 2090 by folding the distal end of implant bag 2002. Implant bag 2002 is slid along insertion sleeve 2090 in the general direction of arrow F (FIG. 76) until the medial aspect of the folded distal tip of implant bag 2002 is flush with distal end 2092 of insertion sleeve 2090, shown in FIG. 78.

Figure 78A:
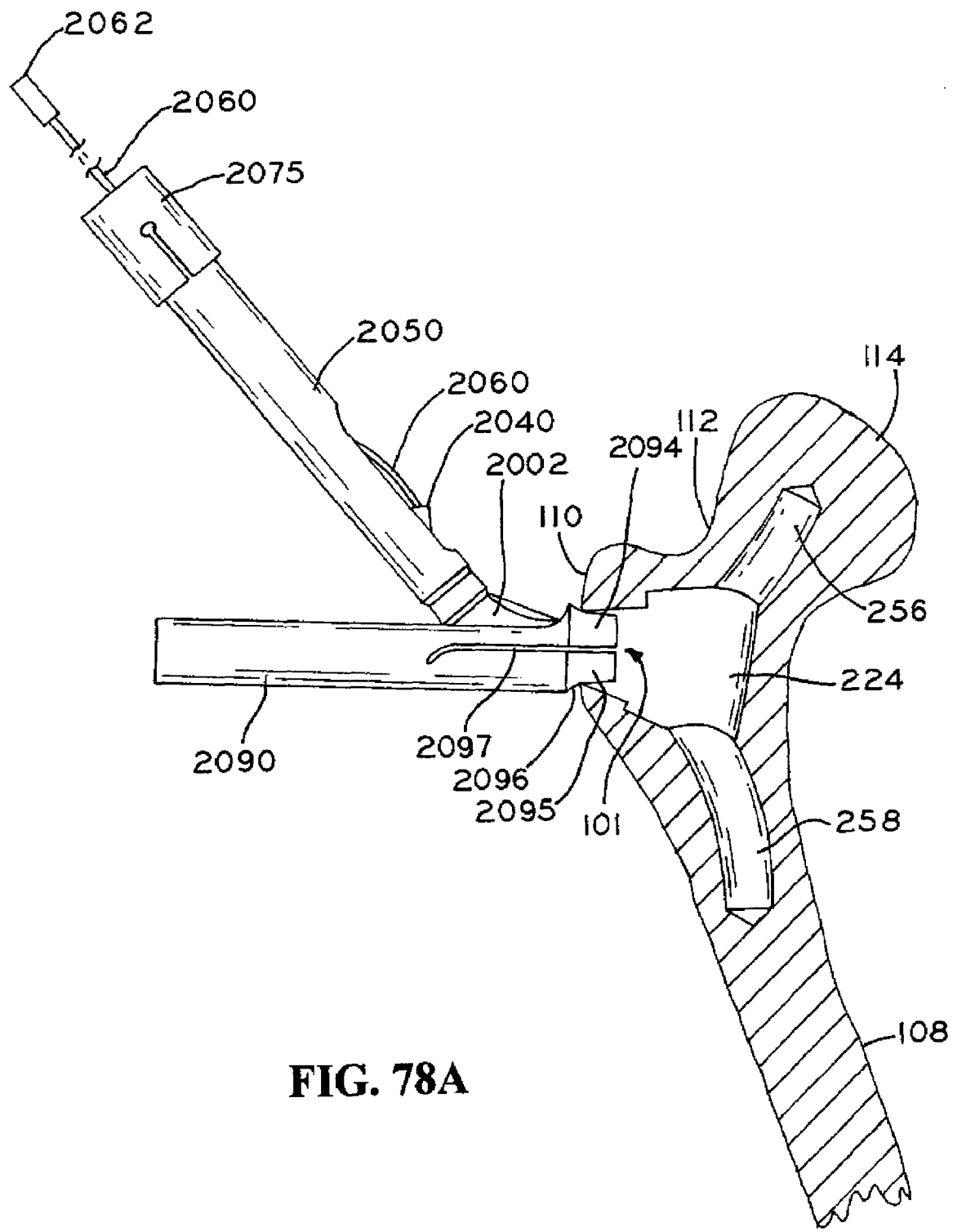
FIG. 78A is a perspective view of the device of FIG. 78 inserted into the femur of the patient of FIG. 1.

Referring now to FIG. 78A, insertion sleeve 2090 may then be placed into access 101 in greater trochanter 110 such that longitudinal opening 2091 of insertion sleeve 2090 is facing superior to slot 2097 and shoulder 2096 abuts against greater trochanter 110. Distal end 2092 is sized slightly smaller than access 101 to permit shoulder 2096 abutment against greater trochanter 110. Implant bag 2002 is then pushed into cavity 224 with implant utility tube 2050. Fluoroscopic images may provide assurance that implant bag 2002 is fully deployed. Groove 2059 of implant utility tube 2050 must be flush with the face of greater trochanter 110 for implant bag 2002 to be fully inserted. Wires 3000a, 3000b facilitate extension of implant bag 2002 into femoral shaft arm 258.

Once implant bag 2002 is fully deployed in femoral shaft arm 258, insertion sleeve 2090 is slid off of implant bag 2002 and removed from access 101.

In an alternative embodiment shown in FIGS. 79-81, deployment instrument 2080 may be used in lieu of spring guide 2070/wires 3000a, 3000b of FIGS. 72-74 to deploy implant bag 2002 into femoral shaft arm 258. Deployment instrument 2080 includes end 2081 connected to deployment wire 2084. Deployment instrument 2080 further includes handle 2085 with wire housing 2083 attached at a proximal end thereof and wire guide 2086 attached at a distal end thereof. Wire guide 2086 functions to guide deployment wire 2084. Slide handle 2082 includes deployment wire 2084 fixedly attached at a distal end thereof.

In operation, slide handle 2082 is slidingly engageable with wire housing 2083. Deployment wire 2084 is completely encompassed within wire guide 2086 in a non-extended position, shown in FIG. 81. To extend deployment wire 2084 and allow the return of wire 2084 to its normal curved shape, handle 2085 with wire housing 2083 is moved in the direction of arrow G such that wire housing 2083 is accepted within slide handle 2082. When wire housing 2083 enters slide handle 2082, deployment wire 2084 is extended beyond wire guide 2086 to return to its curved shape, shown in FIG. 80. Deployment wire 2084, in one embodiment, is formed of nitinol or any other shape-memory metal. The ability to keep deployment wire 2084 straight via wire guide 2086 permits efficient entry into cavity 224. The curved shape of deployment wire 2084 facilitates deploying implant bag 2002 into femoral shaft arm 258. End 2081, shown in FIGS. 79A and 79C, further facilitates deploying implant bag 2002 and is shaped such as to not tear implant bag 2002.

J. Lag Deployment

Referring again to FIGS. 55-57, to effect deformation of radially expanding fingers 928 of lag 264, threaded end cap 936 is provided. Threaded end cap 936 includes a central threaded aperture into which a deformation tool such as deformation tool 938, shown in FIG. 56, can be threaded. Deformation tool 938 includes an internal flexible and threaded shaft which can be advanced into the hollow interior of lag 264 and threadedly engaged with end cap 936. Once engaged with end cap 936, distal to proximal movement of the threaded shaft of deformation tool 938 will cause deformation of radially expanding fingers 928 into the position shown in FIG. 57, as discussed above. In an alternative embodiment, deformation tool 938 includes a curved shaft having a curvature matching that of lag 264. In this embodiment, the curved shaft is inserted through the hollow interior of lag 264 and engages end cap 936 to effect deformation of radially expanding fingers 928, as previously described.

Figure 82:
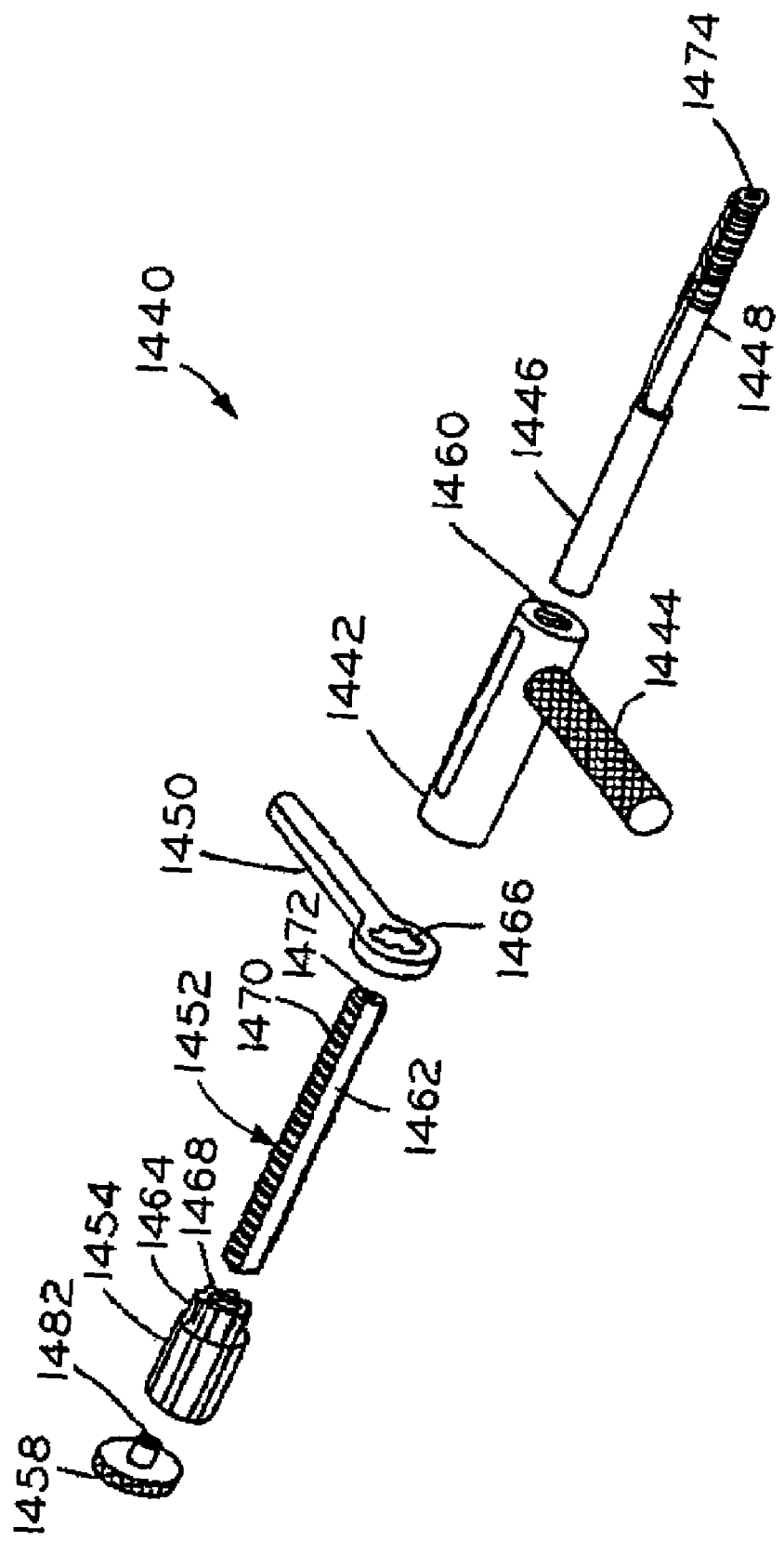
FIG. 82 is an exploded perspective view of a lag actuator according to one embodiment.
Figure 83:
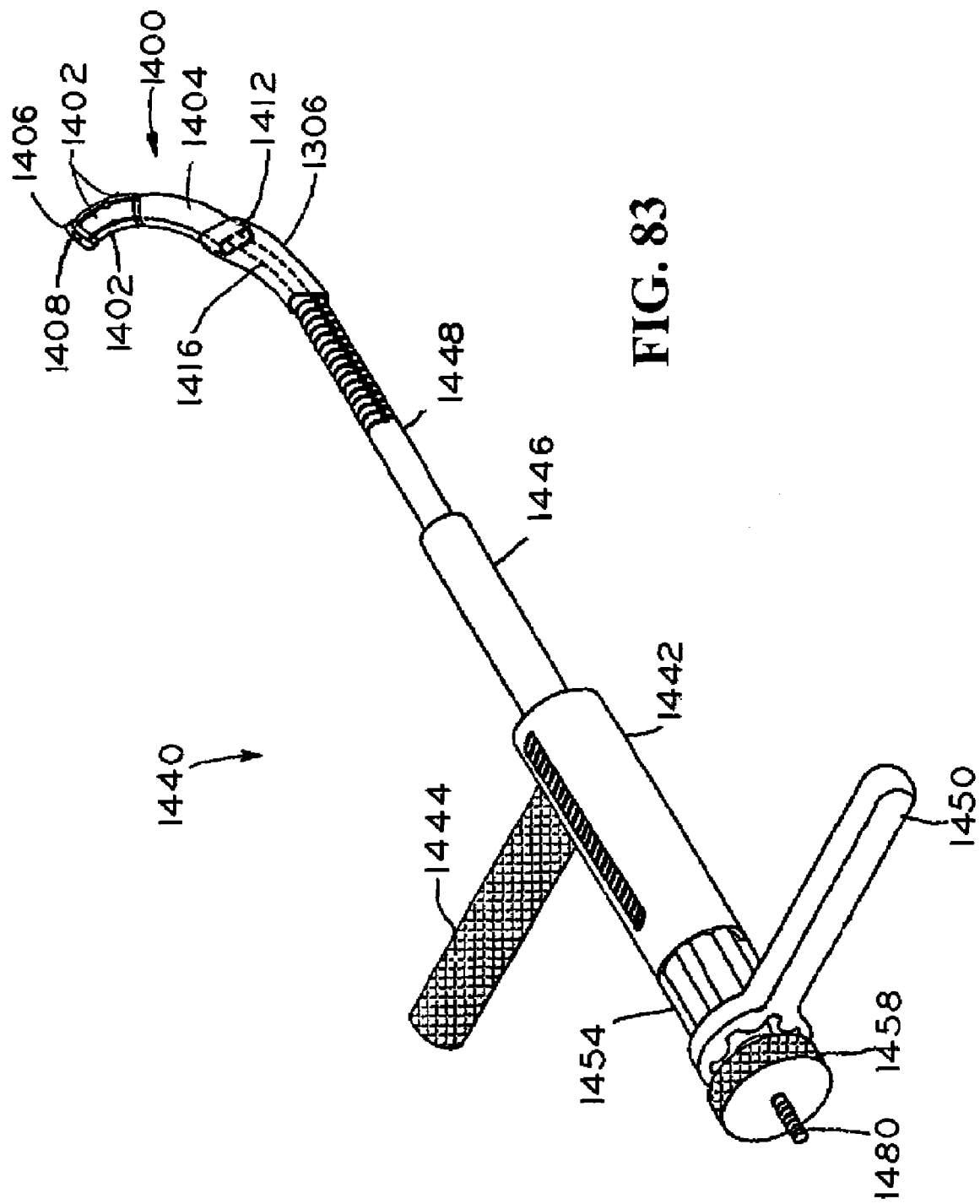
FIG. 83 is a perspective view of the lag actuator of FIG. 82, further illustrating the lag of FIG. 58.
Figure 86B:
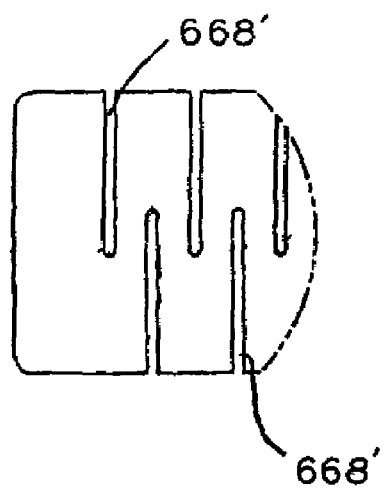
FIG. 86B is a fragmentary view of a portion of the flexible lag cable of FIG. 86A.
Figure 86A:
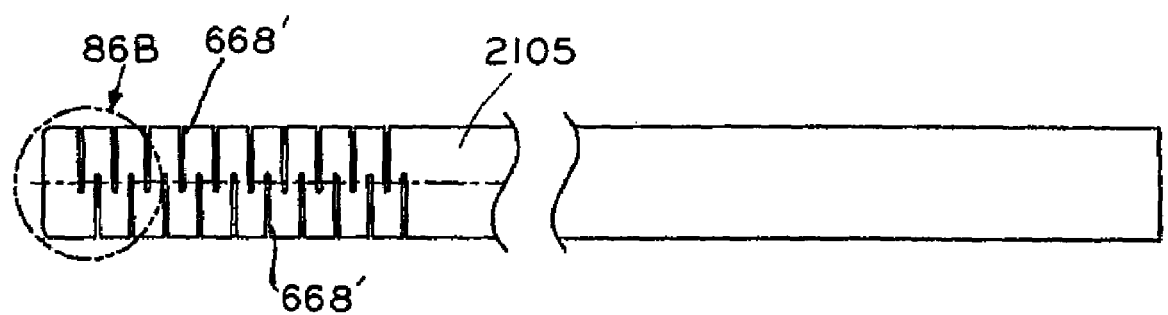
FIG. 86A is a partial plan view of the flexible lag cable.

In an alternative embodiment, referring now to FIGS. 82-83, lag actuator 1440 may be used for applying compression to lag 1400 and expanding fingers 1402 radially outwardly. Preferably, lag actuator 1440 is capable of compressing lag 1400 to a load of at least about 454 kg (1,000 lbs.) or at least about twice the deformation force of lag 1400. As shown in FIG. 82, lag actuator 1440 includes body 1442, handle 1444, intermediate shaft 1446, flexible guide 1448, wrench 1450, linear screw 1452, gear 1454, cable anchor 1458, and compression device 1456, shown in FIG. 62 and described above, which includes cable 1416, anchor 1410, distal spacer 1418, and proximal spacer 1420. Body 1442 includes bore 1460 shaped to axially receive linear screw 1452. Linear screw 1452 may be, for example, an acme screw having at least one flat 1462 longitudinally extending along its length. Bore 1460 correspondingly includes at least one flat (not shown) so that linear screw 1452 may be axially received into bore 1460 while preventing screw 1452 from rotating within body 1442.

Gear 1454 includes external teeth 1464 which may be engaged by corresponding internal teeth 1466 of wrench 1450 for rotational actuation of gear 1454 by wrench 1450. Gear 1454 also includes internal thread 1468 which corresponds to threads 1470 of linear screw 1452. In construction, rotation of wrench 1450 on gear 1454 axially translates linear screw 1452 relative to body 1442. Axial rather than rotational translation is provided because of the matching of flat 1462 of linear screw 1452 with the internal flat of bore 1460. Linear screw 1452 is cannulated by bore 1472 which receives cable 1416 (FIGS. 60-62) there through.

Intermediate shaft 1446 and flexible guide 1448 are also cannulated to receive cable 1416 through bore 1474. Flexible guide 1448 includes a substantially elliptical cross-section shaped to be slidingly received into lag tube 1306 (FIGS. 45 and 49A). Flexible guide 1448 may also be cut as described above in order to provide flexibility in a single plane, thereby facilitating extension into the interior of lag tube 1306 until butted against proximal end 1412 of lag 1400, shown in FIG. 83.

Referring now to FIGS. 62, 82, and 83, anchor 1410 may be T-shaped with engagement ears 1476 for engaging distal apertures 1408 of lag 1400, as described above. Anchor 1410 may be coupled to cable 1416 in order to withstand a tension of at least approximately 454 kg (1,000 pounds). Proximal end 1478 of cable 1416 is coupled to threaded shaft 1480. Threaded shaft 1480 may be received through bore 1474 of flexible guide 1448, bore 1460 of body 1442, bore 1472 of linear screw 1452, internal thread 1468 of gear 1454, internal teeth 1466 of wrench 1450, and engaged with internal thread 1482 of cable anchor 1458, thereby coupling together the assembly of lag actuator 1440 with lag 1400, shown in FIG. 83. As wrench 1450 is rotated, linear screw 1452 translates in a proximal axial direction, displacing cable anchor 1458 and therefore cable 1416 proximally relative to flexible guide 1448. Proximal displacement of cable 1416 compresses distal end 1408 of lag 1400, against flexible guide 1448, thereby expanding fingers 1402 radially outwardly, as described above.

Upon full expansion of fingers 1402 in femoral head arm 256, wrench 1450 may be rotated in the opposite direction to loosen the tension on cable 1416. Lag actuator 1440 may then be removed from cable 1416 by uncoupling proximal end 1478 of cable 1416 and threaded shaft 1480. Lag actuator 1440 may then be removed from contact with lag 1400. Cable 1416 may be removed from lag 1400 by turning cable 1416 clockwise or counterclockwise 90 degrees. Such turning action releases anchor 1410 from engagement with distal apertures 1408 of lag 1400 and allows cable 1416 to be slid out of lag 1400.

Figure 89:
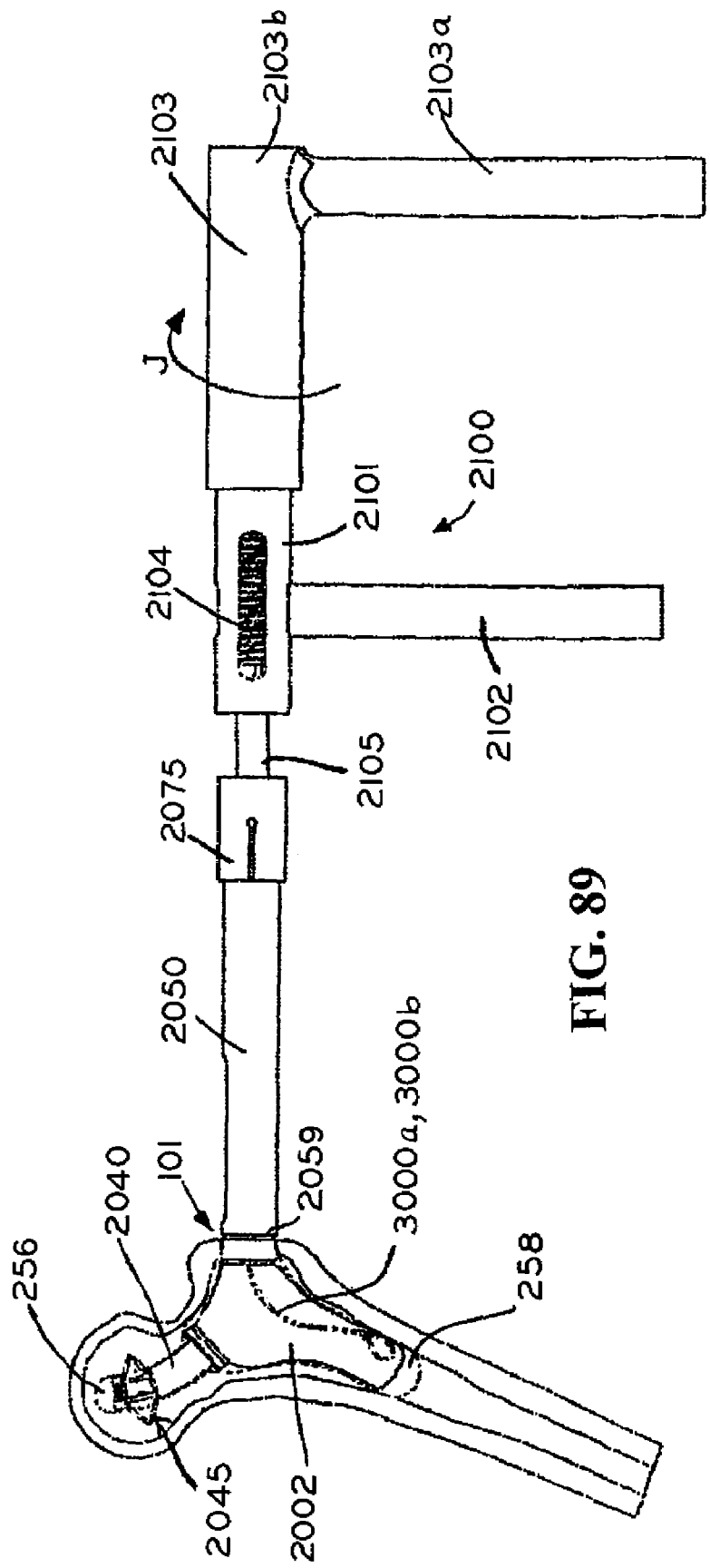
FIG. 89 is a perspective view of the lag actuator of FIG. 87, further illustrating the lag wrench coupled thereto.
Figure 90:
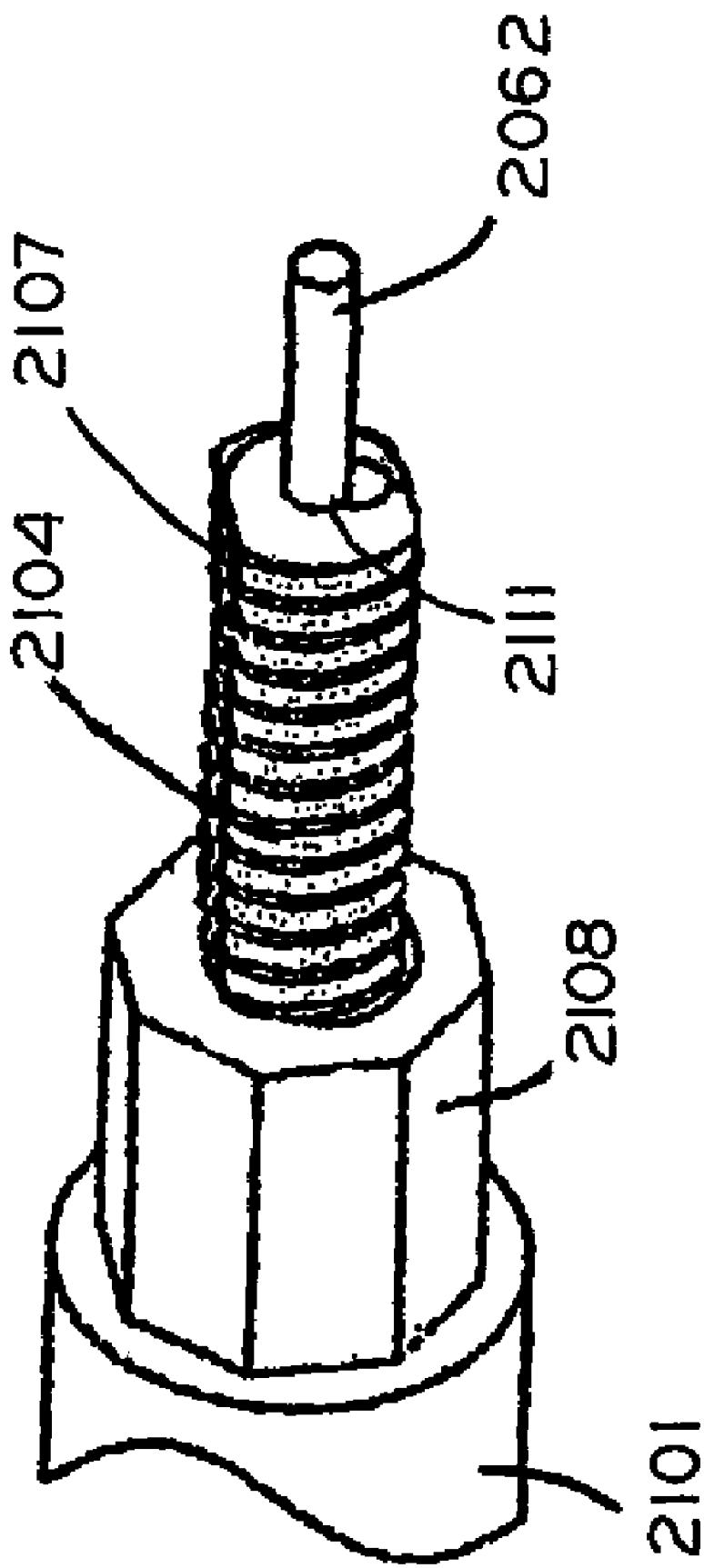
FIG. 90 is a fragmentary view of a portion of the lag actuator of FIG. 87.

In an alternative embodiment shown in FIGS. 84-89, lag 2040 may be actuated via lag actuator 2100 to anchor lag 2040 in femoral head arm 256. Lag actuator 2100 may be used for applying compression to lag 2040 to expand fingers 2045 radially outwardly. Preferably, lag actuator 2100 is capable of compressing lag 2040 to a load of at least about 454 kg (1,000 lbs.) or at least about twice the deformation force of lag 2040. Referring now to FIGS. 87-89, lag actuator 2100 includes body 2101, handle 2102, wrench 2103, and screw 2104. Body 2101 includes a bore there through that is shaped to axially receive linear screw 2104. Linear screw 2104 may be, for example, an acme screw having at least one flat 2107 (FIG. 90) longitudinally extending along its length. The bore in body 2101 correspondingly includes at least one flat so that linear screw 2104 may be axially received into the bore while preventing screw 2104 from rotating within body 2101. Body 2101 also includes at least one threaded bore into which the threads (not shown) of handle 2102 are screwed to attach handle 2102 to body 2101. The inclusion of multiple bores permits a surgeon to choose the most ideal position for handle 2102 in any situation.

Lag actuator 2100 also includes lag actuator nut 2108 having internal threads corresponding to the threads of screw 2104. Nut 2108 also includes a polygonal surface on at least 1a portion of its exterior to mate with wrench 2103 for rotational actuation of nut 2108. Wrench 2103 includes handle 2103a and body 2103b configured to mate with nut 2108. In operation, rotation of wrench 2103 on nut 2108 axially translates screw 2104 relative to body 2101. Axial rather than rotational translation is provided because of the matching of flat 2107 of linear screw 2104 with the internal flat of the bore in body 2101. Linear screw 2104 is cannulated to receive lag cable 2060 there through.

In operation, shown in FIGS. 84-85, flexible lag brace 2105 is moved in the general direction of arrow H in FIG. 84 and inserted over lag cable 2060 and into implant utility tube 2050 until it butts against lag 2040. Lag 2040 is then pushed into place with flexible lag brace 2105 in femoral head 114, shown in FIG. 85. Flexible lag brace 2105 may include cuts 668', as described above and shown in FIGS. 86A and 86B.

Referring now to FIGS. 87-88, lateral tip 2062 of lag cable 2060 is slid through lag actuator 2100. Lateral tip 2062 of lag cable 2060 must be secured to the proximal end of screw 2104, shown in FIG. 90. Lag cable 2060 extends through the cannulated screw 2104 and lateral tip 2062 must seat in notch 2111 of screw 2104.

Referring now to FIG. 89, wrench 2103 is then used to turn lag actuator nut 2108 clockwise or in the direction of arrow J to tension lag cable 2060. As wrench 2103 is rotated, lag actuator nut 2108 continues turning clockwise to translate screw 2104 in a proximal axial direction, displacing lag cable 2060 proximally relative to flexible lag brace 2105. Proximal displacement of lag cable 2060 compresses distal end 2043 of lag 2040 against flexible lag brace 2105, thereby expanding fingers 2045 radially outwardly, as described above and shown in FIG. 89. Wrench 2103 is continuously rotated to deploy fingers 2045 until adequate fixation is achieved, as determined, for example, by fluoroscopic imaging.

Once fingers 2045 are fully deployed, lag actuator nut 2108 is reversed with lag actuator wrench 2103 in a direction opposite to arrow J to release tension on and loosen lag cable 2060. Lag actuator 2100 can then be removed from lag cable 2060 by moving lateral tip 2062 of lag cable 2060 out of engagement with notch 2111 of screw 2104 and then sliding lag actuator 2100 off of lag cable 2060. To remove lag cable 2060 from lag 2040, lag cable 2060 is rotated counterclockwise until it disengages from threaded recess 2034 of lag support 2030. Lag cable 2060 may then be removed. Spring guide 2070 is then removed while simultaneously holding implant utility tube 2050 and implant bag 2002 steady.

K. Filling the Implant Bag

Figure 91:
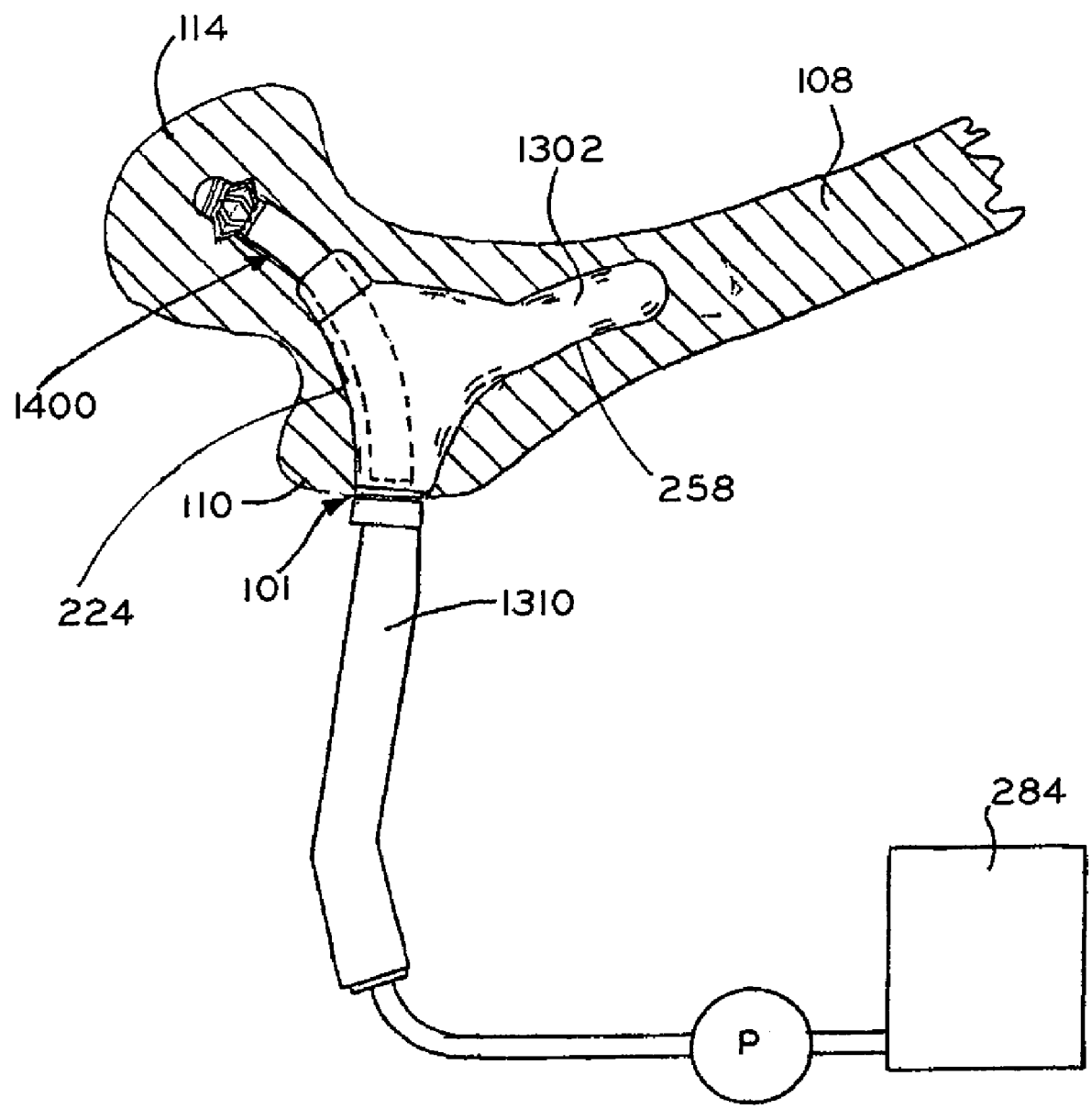
FIG. 91 is a partial sectional view of the assembly of FIG. 67, further illustrating a filler material source with pump coupled thereto.

In one embodiment shown in FIG. 91, to fill implant bag 1302, pump P may be utilized to convey a bag filler material for filling implant bag 1302 from source 284 of bag filler material. In one exemplary embodiment, source 284 of bag filler material comprises a source of bone cement. As implant bag 1302 is filled with, e.g., bone cement, it expands to fill cavity 224 and femoral shaft arm 258. Once implant bag 1302 is filled, the bone cement injected therein cures and provides intramedullary fixation of implant 1300. Insertion tube 1310 may be then uncoupled from implant bag 1302 for closure of incision 106. In order to aid determination of location of implant bag 1302 within femur 108, plug 1333 (FIG. 45) may be at least partially radiopaque for locating end 1330 on a fluoroscopic image.

In an alternative embodiment (not shown), the bag structure of the implant of the present invention comprises a nested bag structure in which an inner bag is filled with a high strength material relative to an outer bag in which the inner bag is placed. The outer bag of this form of the present invention is formed from, and filled with, a more bioresorbable material relative to the material of construction and fill material of the inner bag.

Figure 92:
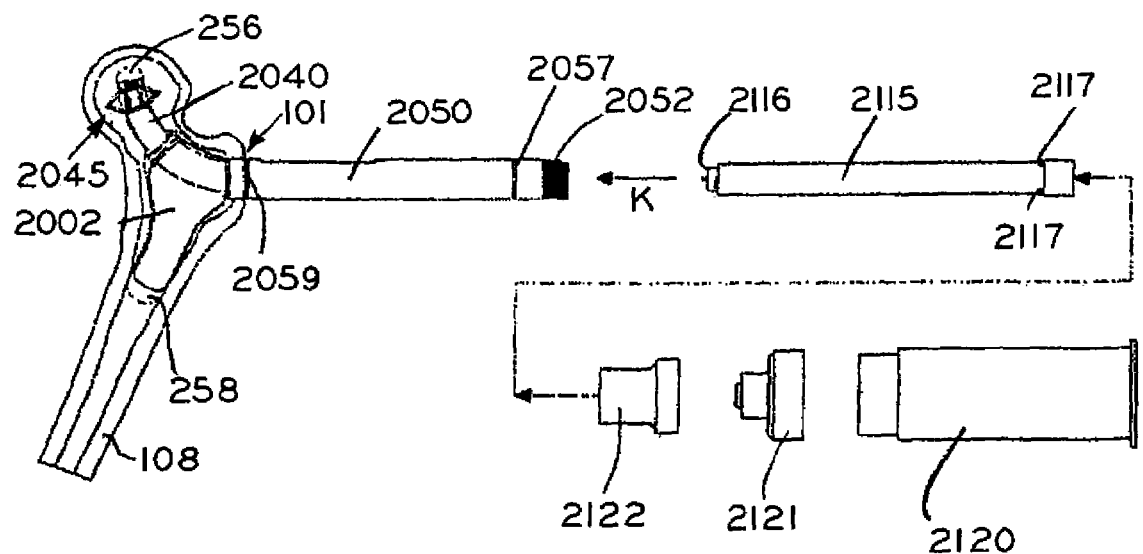
FIG. 92 is a plan view of an implant assembly inserted into a femur with a cement injection means coupled thereto.
Figure 93:
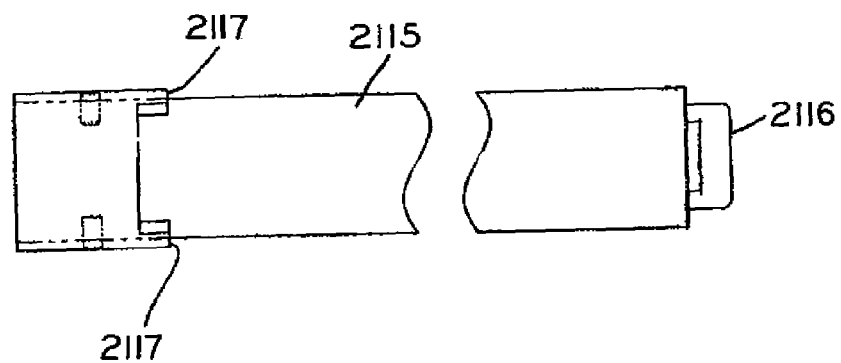
FIG. 93 is a plan view of a filler tube of the cement injection means of FIG. 92.

In an alternative embodiment shown in FIGS. 92-93, filler tube 2115 may be inserted in the general direction of arrow K and into implant utility tube 2050 to fill implant bag 2002. Medial tip 2116 of filler tube 2115 is engaged such that lateral tabs 2117 on filler tube 2115 seat in grooves 2055 (FIG. 72) of implant utility tube 2050. Medial tip 2116 is shaped to mate with and plug entry into implant tube 2012. In this way, filler material injected into filler tube 2115 enters implant bag 2002 via the fill ports and does not contact the interior of implant tube 2012 or lag 2040. The filler material may be placed into cartridge 2120 after which cap 2121 is threaded into filler nut 2122 and onto cartridge 2120. Filler nut 2122 is then threaded onto threads 2052 of implant utility tube 2050. A pump, such as pump P shown in FIG. 91, or a cement gun may then be assembled onto cartridge 2120 to provide a means for forcing filler material into implant bag 2002. After filling implant bag 2002, the cement gun or pump, cartridge 2120, filler nut 2122, and cap 2121 are removed from implant utility tube 2050. Implant utility tube 2050 should be left in place for several minutes to allow the filler material to harden and avoid disruption of the construct. To remove implant utility tube 2050 after this time period has elapsed, implant utility tube 2050 is rotated counterclockwise 45 degrees and pulled out of access 101.

L. Wound Closure

Incision 106 may now be closed and a soft compression dressing may be applied.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An orthopedic implant for implantation into a cavity formed within an anatomical structure, comprising:
    a bag including a fill access providing access to an interior of said bag;
    a structural support disposed at least partially within said bag, said structural support defining an outer periphery transverse to a longitudinal axis of said structural support; and
    a lag cooperating with said structural support, said lag including a head, said head including a thread extending radially outwardly from said lag, said thread having an outer diameter extending beyond said outer periphery of said structural support, said structural support comprising a tube having an exterior wall and an interior wall defining a hollow interior; and
    a retaining ring circumferentially capturing said bag against said tube.

2. The orthopedic implant of claim 1, wherein said bag is fixedly secured to at least one end of said tube.

3. The orthopedic implant of claim 1, wherein said tube includes insertion tool engagement structure.

4. The orthopedic implant of claim 1, further comprising a lag, said lag cooperating with said structural support.

5. The orthopedic implant of claim 1, wherein said bag comprises at least one material selected from the group consisting of biocompatible acrylic material, polymer material, glass fiber material, ceramic fiber material, stainless steel fiber material, titanium fiber material, titanium alloy fiber material, tantalum fiber material, shape-memory material, and hydrogel materials.

6. An orthopedic implant for implantation into a cavity formed within an anatomical structure, comprising:
    a bag including a fill access providing access to an interior of said bag;
    a structural support disposed at least partially within said bag, said structural support comprising a tube having an exterior wall and an interior wall defining a hollow interior;
    a retaining ring circumferentially capturing said bag against said tube; and
    a lag, said lag cooperating with said structural support;
    wherein said lag comprises at least one radially expandable finger.

7. The orthopedic implant of claim 6, wherein said lag comprises a plurality of
radially expandable fingers.

8. The orthopedic implant of claim 7, wherein said lag has a central axis and upon axial compression of said lag along said central axis, said radially expandable fingers are deformable to radially expand.

9. An orthopedic implant assembly for implanting an orthopedic implant into a cavity formed within an anatomical structure, comprising:
    an orthopedic implant, said orthopedic implant comprising:
        a bag including a fill access providing access to an interior of said bag;
        a structural support disposed at least partially within said bag, said structural support including first engagement structure, said structural support comprising a tube having an exterior wall and an interior wall defining a hollow interior;
        a retaining ring circumferentially capturing said bag against said tube; and
        a lag, said lag cooperating with said structural support;
    an implant insertion tool including second engagement structure engageable with said first engagement structure, said implant insertion tool including at least one passage which is placed in fluid communication with said fill access of said bag upon engagement of said first engagement structure with said second engagement structure.

10. The orthopedic implant assembly of claim 9, wherein said bag is fixedly secured to at least one end of said tube.

11. The orthopedic implant assembly of claim 9, wherein said first engagement structure comprises one of a projection and a recess, and said second engagement structure comprises the other of a projection and a recess.

12. The orthopedic implant assembly of claim 9, wherein said bag comprises at least one material selected from the group consisting of biocompatible acrylic material, polymer material, glass fiber material, ceramic fiber material, stainless steel fiber material, titanium fiber material, titanium alloy fiber material, tantalum fiber material, shape-memory material, and hydrogel materials.

13. An orthopedic implant assembly for implanting an orthopedic implant into a cavity formed within an anatomical structure, comprising:
    an orthopedic implant, said orthopedic implant comprising:
        a bag including a fill access providing access to an interior of said bag;
        a structural support disposed at least partially within said bag, said structural support including first engagement structure; and
        a lag, said lag cooperating with said structural support, said lag comprising at least one radially expandable finger;
    an implant insertion tool including second engagement structure engageable with said first engagement structure, said implant insertion tool including at least one passage which is placed in fluid communication with said fill access of said bag upon engagement of said first engagement structure with said second engagement structure.

14. An orthopedic implant assembly for implanting an orthopedic implant into a cavity formed within an anatomical structure, comprising:
    an orthopedic implant, said orthopedic implant comprising:
        a bag including a fill access providing access to an interior of said bag;
        a structural support disposed at least partially within said bag, said structural support including first engagement structure; and
        a lag, said lag cooperating with said structural support, said lag comprising a plurality of radially expandable fingers;
    an implant insertion tool including second engagement structure engageable with said first engagement structure, said implant insertion tool including at least one passage which is placed in fluid communication with said fill access of said bag upon engagement of said first engagement structure with said second engagement structure.

15. An orthopedic implant assembly for implanting an orthopedic implant into a cavity formed within an anatomical structure, comprising:
    an orthopedic implant, said orthopedic implant comprising:
        a bag including a fill access providing access to an interior of said bag;
        a structural support disposed at least partially within said bag, said structural support including first engagement structure; and
        a lag, said lag cooperating with said structural support, said lag has a central axis and upon axial compression of said lag along said central axis, said radially expandable fingers are deformable to radially expand;
    an implant insertion tool including second engagement structure engageable with said first engagement structure, said implant insertion tool including at least one passage which is placed in fluid communication with said fill access of said bag upon engagement of said first engagement structure with said second engagement structure.

* * * * *